United States Patent [19]

Ishikura et al.

[11] Patent Number: 5,580,904

[45] Date of Patent: Dec. 3, 1996

[54] FORMAMIDO AND CARBOXYAMIDO COMPOUNDS WHICH CAN BE RETAINED IN BRAIN

[75] Inventors: Toyoaki Ishikura, Nagareyama; Teruomi Ito, Matsudo; Takashi Kato, Tsukuba; Kazutoshi Horie, Nagareyama; Hiroshi Ishihara, Kashiwa; Takashi Senou, Adachi-ku, all of Japan

[73] Assignee: Drug Delivery System Institute, Ltd., Tokyo, Japan

[21] Appl. No.: 211,304

[22] PCT Filed: Jul. 30, 1993

[86] PCT No.: PCT/JP93/01075

§ 371 Date: Jun. 24, 1994

§ 102(e) Date: Jun. 24, 1994

[87] PCT Pub. No.: WO94/03424

PCT Pub. Date: Feb. 17, 1994

[30] Foreign Application Priority Data

Jul. 30, 1992 [JP] Japan .................................. 4-203897
Jul. 30, 1992 [JP] Japan .................................. 4-203994

[51] Int. Cl.[6] .......................... A61K 31/16; C07C 233/01
[52] U.S. Cl. .......................... 514/616; 514/629; 564/154; 564/215; 564/224; 568/22
[58] Field of Search .................................. 514/616, 629; 564/154, 215, 224; 568/22

[56] References Cited

U.S. PATENT DOCUMENTS 5,212,056  5/1993  Beltramini et al. ................... 430/572

FOREIGN PATENT DOCUMENTS 1-319466  12/1989  Japan .
2-19365   1/1990   Japan .
5-134347  5/1993   Japan .

OTHER PUBLICATIONS

Miyauchi et al., "Studies on orally active cephalosporin esters V. A prodrug approach for oral delivery of 3–thiazoliomethyl cephalosporin," *Chemical and Pharmaceutical Bulletin*, vol. 38, No. 7, pp. 1906–1910 (1990).

*Patent Abstracts of Japan*, vol. 11, No. 282 (C–446), Sep. 11, 1987.

Zoltewicz et al., "Preparation and reactivity of model compounds related to oligomers from thiamin. A mechanism of oligomerisation," *Journal of the American Chemical Society*, vol. 103, No. 16, pp. 4900–4904 (1981).

Ostrovskii et al., "Transketolase inhibitors based on disulphide derivatives of oxythiamin with branched hydrocarbon chains," *Chemical Abstracts*, vol. 102, No. 9, abstract No. 77601d (1985).

Zimatkina et al., "Synthesis and study of some new disulphide derivatives of oxythiamine," *Chemical Abstracts*, vol. 98, No. 11, abstract No. 89309b (1983).

Takamizawa et al., "Pyrimidine derivatives and their related compounds," *Chemical and Pharmaceutical Bulletin*, vol., 21, No. 4, pp. 785–790 (1973).

Morita et al., "Active groups in the structure of thiamine tetrahydrofurfuryl–disulphide in its antipotassium, antiquinidine, and antiacetylcholine effects on guinea pig atria," *Journal of Vitaminology*, vol. 18, No. 4, pp. 225–234 (1972).

*Primary Examiner*—Yogendra N. Gupta
*Attorney, Agent, or Firm*—Wenderoth, Lind & Ponack

[57] ABSTRACT

According to the present invention, a novel compound group which can pass through blood-brain barrier (BBB) with carrying a drug thereon and stay within brain to release the drug and a well-known compound group having the properties described above are provided.

The compound represented by the general formula

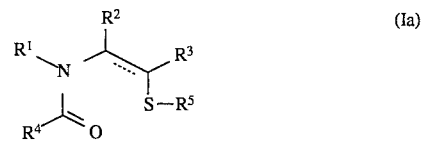

(Ia)

wherein, $R^1$ represents $C_{1-6}$ alkyl which may be substituted by a group selected from hydroxyl, carboxyl, amino group which may be substituted by $C_{1-6}$ alkyl, and a five- to seven-membered saturated heterocyclic ring, $R^2$ represents hydrogen or $C_{1-6}$ alkyl, $R^3$ represents hydrogen or $C_{1-6}$ alkyl which may be substituted by hydroxyl, $R^4$ represents hydrogen or $C_{1-6}$ alkyl, $R^5$ represents an amino acid residue, or —S—$R^6$ or —CO—$R^6$ wherein $R^6$ represents $C_{1-14}$ alkyl which may be substituted by a five- to seven-membered saturated ring; $C_{2-6}$ alkenyl; aryl; or a five- to seven-membered saturated ring; or the group represented by the general formula (IVa):

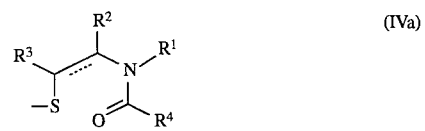

(IVa)

wherein $R^1$, $R^2$, $R^3$ and $R^4$ have the same meanings as defined above, and ╍╍╍ represents a single bond or a double bond provided that at least one of $R^1$, $R^3$ and $R^5$ contains hydroxyl, carboxyl or amino, and a salt thereof.

6 Claims, 5 Drawing Sheets

FORMAMIDO AND CARBOXYAMIDO COMPOUNDS WHICH CAN BE RETAINED IN BRAIN

BACKGROUND OF THE INVENTION

1. Field of the Invention

The present invention relates to a compound which can pass through the blood-brain barrier (BBB) carrying a drug and release the drug while being retained in brain, and to its use.

2. Background Art

Cerebral tissue or cells are separated from blood by very tightly combined cerebral capillary vessels (blood-brain barrier), that is, brain is protected by the strict limitation of the interchange of materials through the blood-brain barrier. Therefore, a drug administered systemically sometimes cannot successfully be delivered to brain being impeded by BBB.

In general, the permeability of materials through BBB is correlated with the lipophilicity of the materials. Thus, some lipophilic prodrugs have been synthesized for the purpose of facilitation of delivery to brain of a drug which is hard to permeate through BBB. On the other hand, brain also possesses a mechanism for active excretion of waste materials and drugs back to the periphery. Therefore, it is considered that the conventional prodrugs which only facilitate their distribution to brain by mainly an increase in the lipophilicity have limitations in maintaining the concentration and efficacy of the drug (Rahimy, M. H., et al., Pharm. Res., 10 (1990) 1061–1067). In other words, it is required to provide a means to enhance the transport of the drug across BBB and to prolong the residence in brain of the drug in order to maintain its efficacy following intravenous administration of a drug.

In order to solve the problem, Bodor (Florida University) has proposed a dihydropyridine prodrug which utilizes the NAD+-NADH redox system (Bodor, N., et. al., Science, 214 (1981) 1370–1372). The lipophilic derivative, when incorporated into cells, is oxidized mainly by the NAD$^+$ oxidation system into a pyridinium cation and retained in brain due to the decrease of its permeability through biological membrane. This method is believed an excellent system for delivering drugs to brain, since the pyridinium cation carrying the drug releases it in a sustained manner. Bodor and his co-workers have already demonstrated the excellence of the method in more than twenty compounds (drugs). However, the dihydropyridine derivative is easily oxidized per se and thus is likely to lead to the deterioration of the quality for example by air oxidation after its synthesis.

The present inventors have examined further possibilities for obtaining the compounds which can pass through BBB and deliver a drug into brain. As a result, we have found that certain kinds of compounds have an excellent property as a carrier for delivering drugs into brain. Thus we have accomplished the present invention.

SUMMARY OF THE INVENTION

The object of the present invention is to provide novel compounds which can pass through the blood-brain barrier (BBB) with a drug carried thereon and release the drug while staying in brain as well as well-known compound groups which possess the above properties.

According to the present invention, there provides the compound represented by the formula (IA):

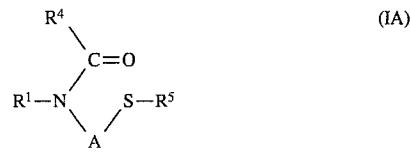

and a salt thereof,
wherein
$R^1$ represents an alkyl group or an alkenyl group, in which one or more hydrogen atoms in the alkyl group or the alkenyl group may be substituted by a group selected from the group consisting of a hydroxyl group which may be esterified, etherified or carbamated, a carboxyl group which may be esterified or amidated, an amino group which may be acylated and a residue of cyclic compounds except 4-amino-2-methyl-5-pyridyl group, A represents the following group:

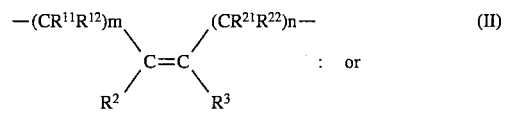

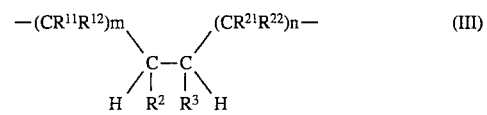

wherein,
$R^2$ and $R^3$ represent independently a hydrogen atom, an alkyl group or an alkenyl group, in which one or more hydrogen atoms in the alkyl group or the alkenyl group may be substituted by a group selected from the group consisting of a hydroxyl group which may be esterified, etherified or carbamated, a carboxyl group which may be esterified or amidated, an amino group which may be acylated and a residue of cyclic compounds, in which $R^2$ and $R^3$ in the formula (II) has a cis-configuration, m and n represent 0 or 1, provided that m and n do not simultaneously represent 1, $R^{11}$, $R^{12}$, $R^{21}$ and $R^{22}$ independently represent a hydrogen atom, an alkyl group or an alkenyl group, in which one or more hydrogen atoms in the alkyl group or the alkenyl group may be substituted by a group selected from the group consisting of a hydroxyl group which may be esterified, etherified or carbamated, a carboxyl group which may be esterified or amidated, an amino group which may be acylated and a residue of a cyclic compound, $R^4$ represents a hydrogen atom or an alkyl group, and $R^5$ represents an amino acid residue or a group —X—Y, in which X represents a sulfur atom or a carbonyl group, and Y represents an alkyl group which may be substituted or an alkenyl group which may be substituted or an alkoxy group which may be substituted or a cyclic compound residue, or the following group (IVA):

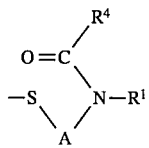

(IVA)

wherein $R^1$, $R^4$ and A have the same meanings as defined above.

According to the present invention, compounds including some known compounds represented by the general formula (IB) which can pass through BBB with a drug supported thereon and release the drug while staying in brain are also provided in addition to the above novel compounds,

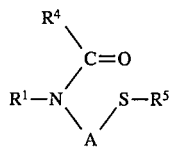

(IB)

wherein, $R^1$ represents an alkyl group or an alkenyl group, in which one or more hydrogen atoms in the alkyl group or the alkenyl group may be substituted by a group selected from the group consisting of a hydroxyl group which may be esterified, etherified or carbamated, a carboxyl group which may be esterified or amidated, an amino group which may be acylated and a residue of cyclic compounds, A has the same meaning as defined in the general formula (IA), $R^4$ represents a hydrogen atom or an alkyl group, and $R^5$ represents an amino acid residue or a group —X—Y, in which X represents a sulfur atom or a carbonyl group, and Y represents an alkyl group which may be substituted, an alkenyl group which may be substituted or an alkoxy group which may be substituted or a cyclic compound residue, or the following group (IVB):

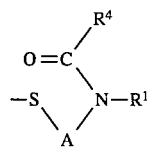

(IVB)

wherein $R^1$, $R^4$ and A have the same meanings as defined above.

DETAILED DESCRIPTION OF THE INVENTION

Novel compounds

Figure 1:
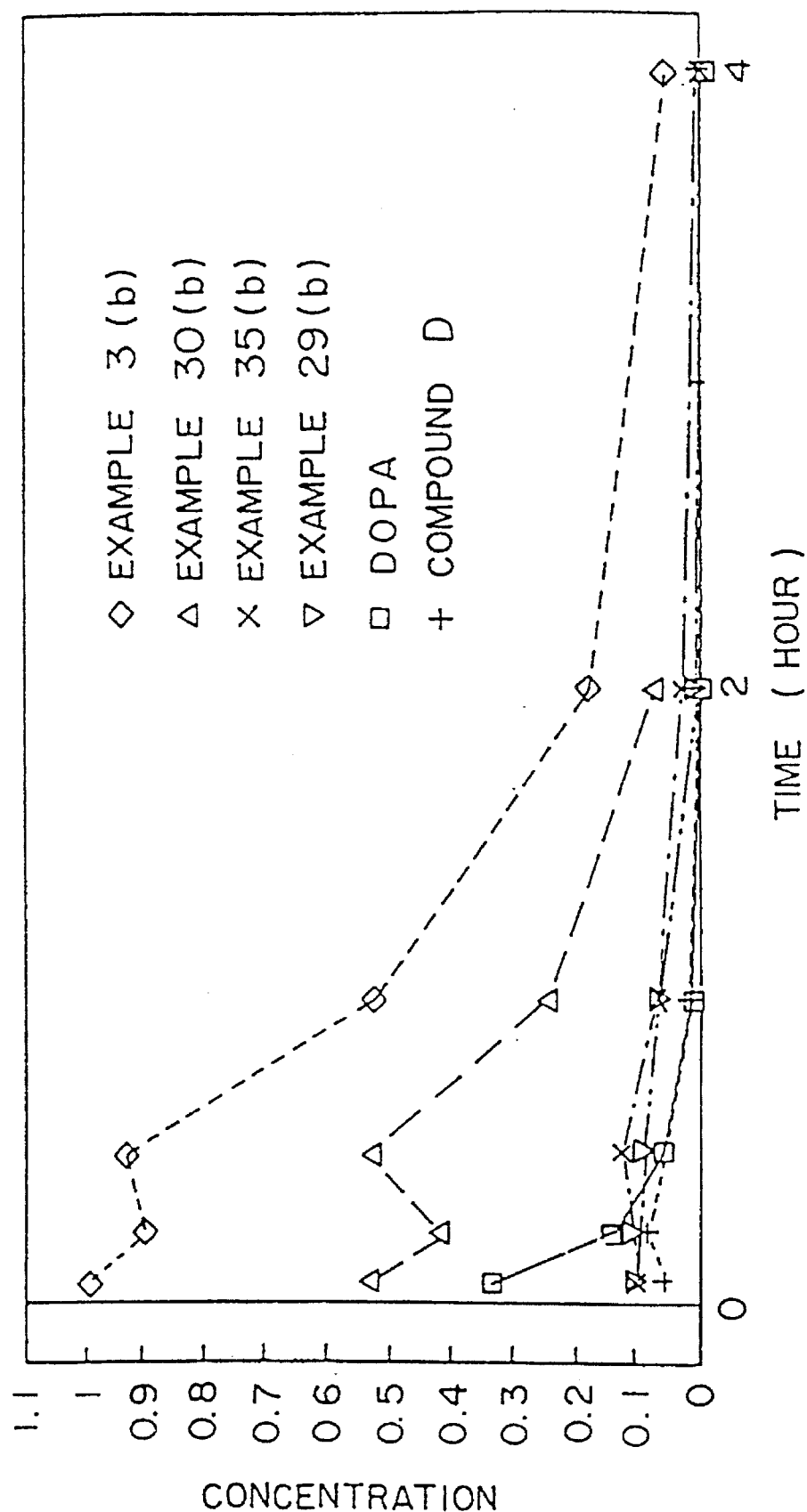

In the present specification, alkyl or alkenyl as a group or a part of a group may be either a straight or branched chain.

In the formula (IA), $R^1$ represents an alkyl group or an alkenyl group, and $R^2$ and $R^3$ independently represent a hydrogen atom, an alkyl group or an alkenyl group, in which the total carbon atoms of the alkyl group or the alkenyl group, which may be appropriately determined in consideration of the liposolubility of the compound, is preferably not more than 20. Individual alkyl group or alkenyl group is preferably a $C_{1-10}$ alkyl group or a $C_{2-10}$ alkenyl group, more preferably a $C_{1-6}$ alkyl group or a $C_{2-6}$ alkenyl group.

One or more hydrogen atoms of the alkyl group and the alkenyl group may be substituted by a hydroxyl group, a carboxyl group, an amino group or a cyclic compound residue.

The hydroxyl group as the substituent may also be esterified or etherified.

Furthermore, the carboxyl group may also be esterified or amidated, more particularly an alkyloxycarbonyl group may be present in place of the carboxyl group.

The amino group may also be acylated, more particularly an alkyloxycarbonylamino group may be present in place of the amino group.

The cyclic compound residue for substituting the hydrogen atom of the alkyl group or the alkenyl group as $R^1$, $R^2$ and $R^3$ includes a phenyl group, a naphthyl group, a $C_{5-7}$ cycloalkyl group and a five- or six-membered heterocyclic ring which comprises up to 2 hetero atoms selected from an oxygen atom, a sulfur atom and nitrogen atom, may be fused together with another ring and may be substituted by a $C_{1-6}$ alkyl group and/or an amino group (e.g., a pyridyl group, a pyrimidyl group, a 4-amino-2-methylpyrimidin-5-yl group, an imidazolyl group, an indolyl group, a furyl group and a tetrahydrofuryl group), except the case that the alkyl group in $R^1$ is replaced by the 4-amino-2-methyl-5-pyrimidyl group.

$R^{11}$ $R^{12}$, $R^{21}$ and $R^{22}$ are the groups which are present when m or n is 1, and specific examples of these groups include preferably the same ones as $R^2$ and $R^3$.

The amino acid residue represented by $R^5$ preferably bonds as an amino acid thioester. The amino acid preferably includes alanine, valine, leucine, isoleucine, phenylalanine, tyrosine, serine, threonine, cysteine, methionine, aspartic acid, asparagine, glutamic acid, glutamine, tryptophane and proline.

In the group —X—Y represented by $R^5$, X represents a sulfur atom or a carbonyl group, Y represents an alkyl group, preferably a $C_{1-18}$ alkyl group, an alkenyl group, preferably a $C_{2-8}$ alkenyl group, an alkoxy group, preferably $C_{1-8}$ alkoxy group, or a cyclic compound residue.

The alkyl group, the alkenyl group and alkoxy group as Y may be substituted by a substituent. The examples of the substituent include an amino group, a $C_{1-7}$ alkyloxycarbonylamino group, a five- or six-membered saturated heterocyclic ring containing one of an oxygen atom or a sulfur atom and a $C_{5-7}$ cycloalkyl group.

Moreover, the examples of the cyclic compound residue as Y include a phenyl group, a naphthyl group, a five- or six-membered heteroaromatic ring containing a nitrogen atom and a five- or six-membered saturated heterocyclic ring containing a nitrogen atom.

When $R^5$ is the group represented by the general formula (IVA), the compound may be symmetrical at the center of the disulfide bond. $R^1$ and $R^4$ present in the right and the left side, respectively, may be the same or different.

When the group A represents the group (II), the stereochemistry of $R^2$ and $R^3$ is of the cis-configuration.

The preferred groups of the compound of the present invention include the compound in which both m and n are 0.

More preferred groups of the novel compounds according to the present invention comprise the compound represented by the following formula (Ia):

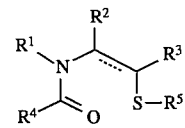

(Ia)

wherein, $R^1$ represents a $C_{1-6}$ alkyl group which may be substituted by a group selected from a hydroxyl group, a carboxyl group, an amino group which may be substituted by a $C_{1-6}$ alkyl group, and a five- to seven-membered saturated heterocyclic ring, $R^2$ represents a hydrogen atom or a $C_{1-6}$ alkyl group, $R^3$ represents a hydrogen atom or a $C_{1-6}$ alkyl group which may be substituted by a hydroxyl group, $R^4$ represents a hydrogen atom or a $C_{1-6}$ alkyl group, $R^5$ represents an amino acid residue, the groups —S—$R^6$ or —CO—$R^6$ in which $R^6$ represents a $C_{1-14}$ alkyl group which may be substituted by a five- to seven-membered saturated ring; a $C_{2-6}$ alkenyl group; an aryl group; a $C_{1-8}$ alkoxy group; or a five- to seven-membered saturated ring; or the group represented by the general formula (IVa):

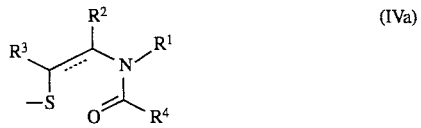

(IVa)

wherein $R^1$, $R^2$, $R^3$ and $R^4$ have the same meanings as defined above, and ......... represents a single bond or a double bond, with the proviso that at least one of $R^1$, $R^3$ and $R^5$ contains a hydroxyl group, a carboxyl group or an amino group.

In the formula (Ia), the $C_{1-6}$ alkyl as $R^1$ is preferably a $C_{1-4}$ alkyl group, more preferably a $C_1$ or $C_2$ alkyl group. The alkyl group may be substituted by a hydroxyl group, a carboxyl group, an amino group which may be substituted by a $C_{1-6}$ alkyl group, preferably a $C_{1-4}$ alkyl, more preferably a $C_1$ or $C_2$ alkyl; or a five-to seven-membered saturated heterocyclic ring which preferably includes a saturated heterocyclic ring comprising a nitrogen atom, more preferably 1-pyrrolidino, 2-pyrrolidinyl, 3-pyrrolidinyl, piperidino, 2-piperidyl. These substituents are preferably present at the end of an alkyl group bonded with N.

In the formula (Ia), the $C_{1-6}$ alkyl as $R^2$ is preferably a $C_{1-4}$ alkyl group, more preferably a $C_1$ or $C_2$ alkyl group.

In the formula (Ia), the $C_{1-6}$ alkyl as $R^3$ is preferably a $C_{1-4}$ alkyl group, more preferably a $C_1$ or $C_2$ alkyl group. The alkyl group may be substituted by a hydroxyl group, and the preferred example of the substituted alkyl group is a 2-hydroxyethyl group.

The $C_{1-6}$ alkyl as $R^4$ is preferably a $C_{1-4}$ alkyl group, more preferably a $C_1$ or $C_2$ alkyl group.

The amino acid residue as $R^5$ preferably bonds as an amino acid thioester. The amino acid preferably includes alanine, valine, leucine, isoleucine, phenylalanine, tyrosine, serine, threonine, cysteine, methionine, aspartic acid, asparagine, glutamic acid, glutamine, tryptophane and proline.

The $C_{1-14}$ alkyl group as $R^6$ in the groups —S—$R^6$ or —CO—$R^6$ represented by $R^5$ may be either a straight or branched chain. When the $C_{1-14}$ alkyl group is a branched chain, the carbon atom bonded to —S— or —CO— is preferably a secondary or tertiary carbon atom. The alkyl group may be substituted by a five- to seven-membered saturated heterocyclic ring which includes preferably a saturated heterocyclic ring including an oxygen atom or a nitrogen atom, for example tetrahydrofuranyl, tetrahydropyranyl, pyrrolidinyl, piperidino and piperidyl. The $C_{2-6}$ alkenyl group as $R^6$ is preferably a $C_{2-4}$ alkenyl group. The aryl group as $R^6$ is preferably a phenyl or naphthyl group. The five- to seven-membered saturated ring as $R^6$ is specifically a cyclopentyl, cyclohexyl or cycloheptyl ring.

When $R^6$ represents the group represented by the formula (IVa), the compound can be symmetrical at the center of the disulfide bond (dimer) $R^1$, $R^2$, $R^3$ and $R^4$ present in each group may be the same or different.

In the general formula (Ia) described above,

......... represents a single bond or a double bond.

In the compound according to the present invention, at least one of the groups $R^1$, $R^3$ and $R^5$ contains a hydroxyl group, a carboxyl group or an amino group. When the compound is used as a drug carrier, the drug is introduced into these functional groups.

Drug Carrier

The compound according to the present invention which can pass through BBB with a drug carried thereon and release the drug while being retained in brain is represented by the general formula (IB). Specifically, the compound group represented by the general formula (IB) comprises the compounds of the general formula (IA) and compounds of the general formula (IA) in which $R^1$ represents an alkyl group substituted by 4-amino-2-methyl-5-pyrimidyl.

A more preferable group of the compound group represented by the general formula (IB) is a compound represented by the general formula (Ib):

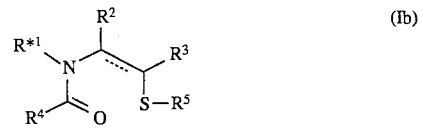

(Ib)

and a salt thereof, wherein, $R^{*1}$ has the same meaning as R1 in claim 1 or represents a $C_{1-6}$ alkyl group substituted by a five- or six-membered hetero aromatic ring which may be substituted by a $C_{1-4}$ alkyl or an amino group and includes one or two nitrogen atoms, $R^2$, $R^3$, $R^4$ and $R^5$ have the same meanings as defined in formula (IB), and at least one of $R^3$ and $R^5$ contains a hydroxyl group, a carboxyl group or an amino group.

As is apparent from the above definitions, the compound group represented by the general formula (Ib) is the compound group represented by the general formula (Ia) to which a compound group in which $R^1$ represents a $C_{1-6}$ alkyl group substituted by a five- or six-membered hetero aromatic ring containing one or two nitrogen atoms is added. Preferred examples of the five- or six-membered hetero aromatic ring containing one or two nitrogen atoms include pyrrolyl, pyridyl, imidazolyl, pyrazolyl, pyridazinyl, pyrimidyl and pyradinyl. These rings may be substituted by a $C_{1-6}$ alkyl group, preferably a $C_{1-4}$ alkyl group, more preferably a $C_1$ or $C_2$ alkyl group and/or an amino group. A preferable example of $R^{*1}$ includes a $C_{1-4}$ alkyl group substituted by 4-amino-2-methyl-5-pyrimidyl.

The derivative according to the present invention can be present as a salt thereof. Examples of the appropriate salts include alkali metal or alkaline earth metal salts such as a sodium salt, a potassium salt and a calcium salt, organic ammoniumn salts such as an ammonium salt and a triethylammonium salt, amino acid salts such as arginine and lysine, a hydrochloride, a sulfate, a nitrate, a perchlorate, organic sulfonic acid salts such as a methanesulfonic acid salt, or organic acid salts such as a succinate, a tartrate and an acetate.

The compound of the formula (I) has a property of passing through BBB with a drug carried thereon and releasing the drug while being retained in brain. Without intending to be bound by theory, it is considered that the compound of the formula (I), after passing through BBB, is cyclized to be formed as a cation after reduced in the case of the disulfide derivative or hydrolyzed in the case of the thioester derivative. As a result, the compound is retained in brain because of decrease in the permeability through BBB.

Therefore, the compound according to the present invention can be used as a drug delivery carrier for carrying a drug thereon, permeating through BBB and delivering the drug into brain.

The drug can be introduced by taking advantage of a variety of functional groups present in $R^1$–$R^5$ as well as $R^{11}$, $R^{12}$, $R^{21}$ and $R^{22}$ of the compound according to the present invention. The drug is preferably introduced in the form of an acid amide bond, an ester bond or an urethane bond with no limitation as far as the bond is cleaved and the drug is released.

The drug which can be introduced is not limited as far as it has a functional group which can be bonded with a functional group present in the compound of the formula (IB) in a bonding fashion cleavable in brain. Also, a drug having no functional groups described above can be modified by introducing appropriately a functional group so that the drug can form a bond with the compound of the formula (IB). The embodiment of a drug which can be introduced includes 3,4-dihydroxy phenylalanine.

It is also said that the lipophilicity and the permeability through BBB of a low-molecular weight compound are generally correlated with each other. The compound according to the present invention has also an advantage in that it has many parts into which a substituent can be introduced and the lipophilicity or the hydrophilicity of a complex having the drug introduced thereinto can be further adjusted by appropriately selecting the substituent.

Furthermore, it can be also said that the compound of the formula (IB) has a disulfide structure or a thioester structure and is hard to be oxidized.

Synthesis of the drug carrier and introduction of the drug

The compound according to the present invention can be produced by the following method in accordance with the reports by Matsukawa et al. ((1) Taizo Matsukawa, Takeo Iwatsu, Hajime Kawasaki, Study of Vitamin B1 and related compounds (No. 43), Synthesis of Allithiamine Homologues-2, Yakugaku Zasshi, 73 (1953) 497–501; or (2) Taizo Matsukawa and Hajime Kawasaki, Study of Vitamin B1 and related compounds (No. 45), Diol type Vitamin B1 derivatives-1, Yakugaku Zasshi, 73 (1953) 705–708)).

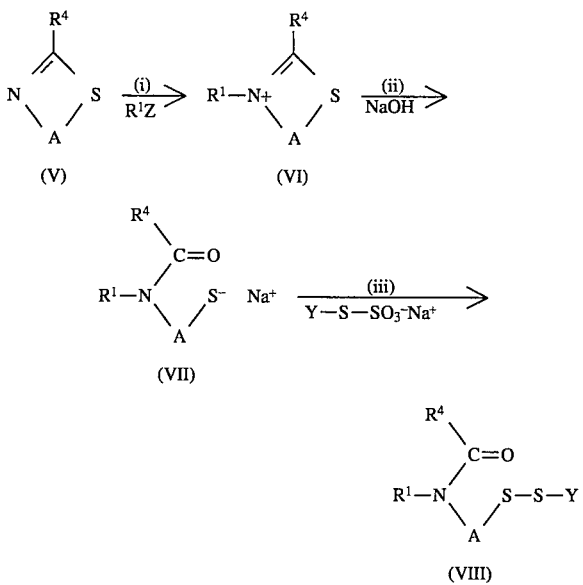

wherein $R^1$, $R^4$, A and Y have the same meanings as defined in the formulae (IA) and (IB), and Z represents a halogen atom such as chlorine, bromine or iodine or a leaving group such as a tosyl group or a mesyl group.

The reaction in the step (i) can be effected by mixing the compound of the formula (V) with $R^1Z$ in the presence or the absence of of a solvent such as ethanol or dioxane at room temperature or under heating.

The reaction in the step (ii) is the process for cleaving the cyclic structure of the formula (VI). The cleavage can be effected by mixing the compound of the formula (VI) with a sodium hydroxide solution at room temperature or under heating. The reaction in the subsequent step (iii) is usually effected without isolating the compound (VII) obtained in this step to give the compound (VIII).

Among the compounds according to the present invention, the compound (VIII) of the disulfide type, that is the one of the formula (IB) in which X represents a sulfur atom, can be obtained via the step (iii). The reaction can be effected by adding the compound of the formula Y—S—$SO_3Na$ to the compound of the formula (VII) with stirring at room temperature. The compound of the formula Y—S—$SO_3Na$ can be prepared by heating the mixture of an aqueous solution of sodium thiosulfate and an ethanolic solution of the equimolar Y—Z wherein Z represents halogen, under reflux for 1 to 10 hours.

The completely symmetrical compound of the disulfide type can be prepared by adding dropwise an aqueous solution of iodine-potassium iodide to the compound of the formula (VII) with stirring.

Furthermore, the compound of the formula (IB) in which X represents carbonyl can be prepared by reacting the compound of the formula (VII) with an acylating agent containing the group Y such as an acid chloride, an acid anhydride or a sodium acylthiosulfate in an organic solvent such as ethanol or acetone or in an aqueous solution containing or not containing inorganic salts such as sodium chloride or sodium sulfate at a temperature of room temperature to 50° C.

It is needless to say that the functional groups in the aforementioned synthesis reactions may be protected optionally by an appropriate protective group.

The drug can be introduced by an appropriate method corresponding to the functional groups and the functional groups present in the drug. For instance, in the case of the compound represented by the formula (I) and a drug containing a carboxyl group, the drug can be introduced by reacting the drug with the compound represented by the formula (I) under the ester forming condition. Also, in the case of the compound represented by the formula (I) and a drug containing an amino group, the drug can be introduced by reacting these compounds under the carbamate forming condition. In the case of the compound represented by the formula (I) containing an amino group and a drug containing a carboxyl group, the drug can be introduced by reacting these compounds under the amide bond forming condition. During the reaction of introducing a drug, it is preferred to protect the other functional groups with appropriate protective groups.

EXAMPLE

The present invention is further illustrated with reference to the following examples, but it is not limited thereto.

In this connection, the following abbreviations are used in the present specification:

Compound A: N-dansyl ethylenediamine,
Compound B: N-dansyl β-alanine,
Compound C: N-dansyl L-alanine,
Compound D: N-(tert-butoxycarbonyl)-L-3[3,4-di(pivaloyl-oxy)phenyl]alanine, and
Boc: tert-butyloxycarbonyl group.

In $^1$H-NMR spectrum of the formamide derivative, the compound wherein $R^4$ represents a hydrogen atom, the peaks which are probably attributed to the hydrogens of the N-formyl group are often observed in a split pattern. Although the ratio of the peaks depends on the compounds, it varies largely even in the same compound depending on solvents used and thus presumably is attributed to the rotational isomers of the N-formyl group. The ratio of the "isomeric mixture" described in the term of 1H-NMR in examples represents the abundance of the isomers approximately calculated under the experimental condition.

Intermediate 1:

N-4-Dimethyl-5-[(2-hydroxy)ethyl]thiazolium iodide

Methyl iodide (80 ml) was added to 4-methyl-5-thiazole ethanol (100 g), and the mixture was heated under reflux for 2 hours. The reaction was concentrated under reduced pressure to give a dark-brown amorphous residue. The residue was solidified by adding ether (400 ml) to the residue. The solid product was further washed twice with ether (500 ml). The powdery solid products were collected by filtration and dried under reduced pressure.

Yield: 202 g.

NMR (in $D_2O$): δ4.10 (3H, s), 3.86 (2H, m), 3.14 (2H, t), 2.48 (3H, s).

Intermediate 2:

N-[(2-hydroxy)ethyl]thiazolium bromide

Thiazole (4.3 g) and 2-bromoethanol (12.5 g) were mixed and heated under reflux for 5 hours. The reaction was left standing at room temperature to give white needles. The crystals were washed with acetone, collected by filtration and dried under reduced pressure.

Yield: 9.53 g.

NMR: (in DMSO-$d_6$): δ10.14 (1H, m), 8.54 & 8.34 (each 1H, dd), 4.62 (2H, t), 3.81 (2H, m).

Intermediate 3:

N-(carboxymethyl)thiazolium bromide

Thiazole (8.5 g), 2-bromoacetic acid (15.0 g) and acetone (20 ml) were mixed together and left standing at room temperature for 2 days. White crystals deposited were collected by filtration and washed with acetone.

Yield: 16.96 g.

NMR (in DMSO-$d_6$): δ10.22 (1H, d, J=1.5 Hz), 8.53 & 8.35 (each 1H, each dd), 5.51 (2H, s).

Intermediate 4:

N-[(2-hydroxy)ethyl]-4-methylthiazolium bromide

To the mixture of 4-methylthiazole (24 g) and dioxane (30 ml) was added 2-bromoethanol (40 g), and the resulting mixture was heated under reflux for 4 hours. To the reaction left standing at room temperature for about 0.5 hour was added acetone (100 ml) with stirring to give white to pale yellow solids, which were collected by filtration, washed with acetone and dried under reduced pressure.

Yield: 43.4 g.

NMR (in DMSO-$d_6$): δ10.4 (1H, d), 8.01 (1H, m), 4.53 (2H, t), 3.80 (2H, t), 2.56 (3H,d).

Intermediate 5:

N-[(2-hydroxy)ethyl]-5-methylthiazolium bromide

To the mixture of 5-methylthiazole (10 g) and dioxane (20 ml) was added 2-bromoethanol (15 g), and the resulting mixture was heated under reflux for 4 hours. To the mixture left standing at room temperature for about 0.5 hour was added acetone (100 ml) with stirring to crystallize pale yellow solids. The supernatant was discarded, and acetone (50 ml) and ether (150 ml) were added with stirring to give white to pale yellow solids, which were collected by filtration, washed with ether and dried under reduced pressure.

Yield: 19.3 g.

NMR (in DMSO-$d_6$): δ9.96 (1H, d, J=1.5 Hz), 8.32 (1H, t), 4.54 (2H, t), 3.79 (2H, t), 2.57 (3H, d, J=1.5 Hz).

Intermediate 6:

N-[(2-hydroxy)ethyl]-2,4-dimethylthiazolium bromide

To the mixture of 2.4-dimethylthiazole (26.0 g) and dioxane (30 ml) was added 2-bromoethanol (40 g), and the resulting mixture was heated under reflux for 5 hours. To the mixture left standing at room temperature for about 0.5 hour was added acetone (150 ml) with stirring to give pale yellowish white solids. To the mixture was further added ether (150 ml), and the resulting powdery crystals were collected by filtration, washed with acetone and dried under reduced pressure.

Yield: 37.52 g.

NMR (in DMSO-$d_6$): δ7.81 (1H, d), 4.46 (2H, t), 3.79 (2H, t), 3.00 (3H, s), 2.54 (3H, d).

Intermediate 7:

N-5-di-[(2,hydroxy)ethyl]-4-methylthiazolium bromide

To the mixture of 4-methyl-5-thiazole ethanol (29 g) and dioxane (30 ml) was added 2-bromoethanol (35 g), and the resulting mixture was heated under reflux for 1.5 hours. To the mixture left standing at room temperature for about 0.5 hour was added acetone (100 ml) with stirring to give white to pale yellow solids, which were collected by filtration, washed with acetone and dried under reduced pressure.

Yield: 42.8 g.

NMR (in DMSO-$d_6$): δ9.92 (1H, s), 4.54 (2H, t), 3.79 (2H, t), 3.65 (2H, t), 3.03 (2H, t).

Intermediate 8:

N-[[2-(tert-butyloxycarbonyl)amino]ethyl]-5-[(2-hydroxy)ethyl]-4-methylthiazolium bromide 2-Bromoethylammonium bromide (40.0 g) and 4-methyl-5-thiazole ethanol (29.0 g) were dissolved in a hot mixed solution of ethanol (50 ml) and dioxane (150 ml), and the mixture was heated under reflux for about 30 hours. Acetone (150 ml) was added to the reaction having been cooled. The mixture was left standing under ice-cooling for 1 hour to give powdery crystals, which were collected by filtration, washed with ethanol (150 ml) and dried under reduced pressure.

Yield: 42.2 g.

NMR (in $CD_3OD$): δ4.9–4.8 (2H, m), 3.84 (2H, t), 3.59 (2H, t), 3.14 (2H, t), 2.51 (3H, s).

NMR (in DMSO-$d_6$): δ10.04 (1H, s), 4.73 (2H, t), 3.66 (2H, t), 3.40 (2H, broad), 3.04 (2H, t).

The crystals thus obtained (3.5 g) were dissolved in water (50 ml) and adjusted to a pH of 7–8 with sodium hydrogen carbonate. To this solution was added with stirring a solution of di-tert-butyl dicarbonate (2.5 g) in dioxane (50 ml). The stirring was continued at room temperature for 1 hour. Insolubles were removed by filtration, and the filtrate was concentrated under reduced pressure, diluted with ethanol and concentrated again. Acetone (20 ml) was added to the residue, and insolubles were removed by filtration. The filtrate was concentrated under reduced pressure, and the solution of the residue in a minimum amount of ethanol/acetone and added dropwise with stirring to a mixed solution (100 ml) of ether: hexane=5:2. The solids crystallized were collected by filtration and dried under reduced pressure.

Yield: 2.64 g.

NMR (in $CD_3OD$): $\delta 4.56$ (2H, t), 3.81 (2H, t), 3.54 (2H, t), 3.11 (2H, t), 2.57 (3H, s), 1.36 (9H, s).

NMR (in DMSO-$d_6$): $\delta 9.89$ (1H, s), 4.50 (2H, t), 3.63 (2H, dd), 3.40 (2H, dd), 3.01 (2H, t), 2.47 (3H, s), 1.31 (9H, s).

Intermediate 9:

N-[2-(Dimethylamino)ethyl]-5-[(2-hydroxy)ethyl]-4-methylthiazolium chloride hydrochloride To a mixture of 4-methyl-5-thiazole ethanol (16.0 g) and dimethylaminoethyl chloride hydrochloride (14.4 g) was added ethanol (10 ml. The mixture was heated under reflux for about 20 hours. Ethanol (10 ml) and acetone (100 ml) were added, and the mixture was stirred to give pale yellow powdery crystals, which were collected by filtration, washed with acetone containing a small amount of ethanol and dried under reduced pressure.

Yield: 17.1 g.

NMR (in $D_2O$): $\delta 4.94$ (2H, t), 3.86 (2H, broad t), 3.72 (2H, t), 3.16 (3H, broad t), 3.02 (6H, s), 2.56 (3H, s).

Intermediate 10:

N-[2-(1-pyrrolidino)ethyl]-5-[(2-hydroxy)ethyl-4-methylthiazolium chloride hydrochloride To a mixture of 4-methyl-5-thiazole ethanol (14.3 g) and 2-(1-pyrrolidino)ethyl chloride hydrochloride (13.6 g) was added ethanol (10 ml). The mixture was heated under reflux for about 20 hours. After cooling, the mixture was added with ethanol (10 ml) and acetone (100 ml), and stirred to give pale yellow powdery crystals, which were collected by filtration, washed with acetone containing a small amount of ethanol and dried under reduced pressure.

Yield: 16.2 g.

NMR (in DMSO-$d_6$): $\delta 10.30$ (1H, s), 4.98 (2H, t), 3.71 (2H, m), 3.64 (2H, t), 3.57 (2H, m), 3.08 (2H, m), 3.03 (2H, t), 2.54 (3H, s), 2.02 & 1.89 (each 2H, each m).

Intermediate 11:

N-(2-hydroxypropyl)-4-methylthiazolium chloride hydrochloride

To a mixture of 4-methylthiazole (10.0 g) and dioxane (20ml) was further added 1-bromo-2-propanol (containing 20% of 2-bromo-1-propanol) (15.3 g), and the mixture was heated under reflux for about 6 hours. After cooling, the reaction was added with acetone (30 ml) and ether (130 ml) and left standing. After the pale brown supernatant was discarded, ether (150 ml) was further added to the amorphous precipitate to solidify it. Pale brown powder thus crystallized was collected by filtration and dried under reduced pressure.

Yield: 8.74 g.

NMR (in DMSO-$d_6$): $\delta 10.04$ (1H, d, J=3 Hz), 8.01 (1H, q), 4.52 (1H, dd), 4.28 (1H, dd), 4.00 (1H, m), 2.56 (3H, d, J=1 Hz), 1.19 (3H, d, J=6 Hz).

Intermediate 12:

N-(2-hydroxyethyl)-2-methylthiazolium bromide

To a solution of 2-methylthiazoline (10.1 g) in dioxane (20 ml) was added 2-bromoethanol (13.8 g), and the mixture was heated under reflux for about 6 hours. After cooling the reaction, acetone (30 ml) and ether (130 ml) were added with stirring, and the resulting mixture was left standing. After the pale brown supernatant was discarded, ether (150 ml) was further added to the amorphous precipitate thus obtained. The mixture was stirred and left standing. Supernatant obtained was discarded, and the viscous precipitates obtained was left standing at an ambient temperature under reduced pressure to give the title compound as the yellow amorphous residue.

Yield: 19.5 g.

NMR (in DMSO-$d_6$): $\delta 4.51$ (2H, t), 3.87 (2H, t), 3.72 (2H, t), 3.67 (2H, t), 2.61 (3H, s).

Example 1

N-methyl-N-[4-hydroxy-1-methyl-2-[(ethyl)dithio]-1-butenyl]formamide

To a solution of sodium hydroxide (8.0 g) in distilled water (50 ml) was added Intermediate 1 (28.6 g), and the mixture was left standing at room temperature for 10 minutes, during which sodium sulfate was added to saturate the reaction solution. To this aqueous solution was added sodium ethylthiosulfate (46 g) in the form of powder. After the mixture was stirred at room temperature for 10 minutes, it was extracted with ethyl acetate (100 ml). The ethyl acetate layer was dried over anhydrous sodium sulfate and concentrated under reduced pressure. The residue thus obtained was purified by silica gel column chromatography to give a colorless oil product (10.3 g).

1H-NMR (in $CDCl_3$): $\delta 7.98$ & 7.93 (1H, s), 3.82 (2H, m), 2.96 (3H, s), 2.88 (2H, t), 2.63 (2H, q), 2.01 (3H, s), 1.28 (3H, s).

Example 2

(a) N-methyl-N-[4-hydroxy-1-methyl-2-[(1-propyl)dithio]-1-butenyl]formamide

To a solution of sodium hydroxide (2.0 g) in distilled water (50 ml) was added Intermediate 1 (7.2 g), and the mixture was left standing for 10 minutes. To this aqueous solution was added sodium 1-propylthiosulfate (8 g) in the form of powder. A pale yellow oil product was deposited immediately after the addition of sodium 1-propylthiosulfate. The reaction mixture was extracted with ethyl acetate (200 ml). The ethyl acetate layer was dried over anhydrous sodium sulfate and concentrated under reduced pressure. The residue thus obtained was purified by silica gel column chromatography to give a colorless oil product (3.9 g).

1H-NMR (in $CD_3OD$): $\delta 7.98$ & 7.90 (1H, s), 3.72 (2H, t), 2.94 (3H, s), 2.87 (2H, t), 2.62 (2H, t), 2.03 (3H, s), 1.67 (2H, m), 0.98 (3H, t).

(b) N-methyl-N-[4-[2-[(5-dimethylaminonaphtylsulfonyl)amino]ethylaminocarbonyloxy]-1-methyl-2-[(1-propyl)dithio]-1-butenyl]formamide To a solution of the compound in the above step (a) (3.86 g) in tetrahydrofuran (70 ml) was added carbonyldiimidazole (2.6 g) in the form of powder to form a solution in a water bath at 40° C. (for about 10 minutes). To this solution were added Compound A (5.0 g), and the mixture was stirred at room temperature for 15 minutes. After insolubles was removed by filtration, the filtrate was evaporated under reduced pressure. The residue thus obtained was purified by silica gel column chromatography (CHC13:MeOH=80:1→50:1). To a solution of the fluorescent yellowish green solid residue (5.34 g) in ethanol (200 ml) was added 1N HCl (9.4 ml), and the mixture was evaporated under reduced pressure. Evaporation was repeated further twice by adding ethanol to the residue. A solution of the residue thus obtained in an ether containing a small amount of ethanol was added dropwise to ether (300 ml), and the fluorescent yellow solids crystallized was collected by filtration and dried under reduced pressure.

Yield: 3.7 g.

1H-NMR (in CD$_3$OD): δ8.76, 8.49 & 8.34 (each 1H, each d), 7.89 (1H, s), 7.85–7.79 (2H, m), 4.17 (2H, t), 3.35 (6H, s), 3.08–3.05 (3H, m), 2.98–2.91 (3H, m), 2.90 (3H, s), 2.61 (2H, t), 1.99 (3H, s), 1.65 (2H, m), 0.97 (3H, t).

Example 3

(a) N-methyl-N-[4-hydroxy-1-methyl-2-[(2-propyl)dithio]-1-butenyl]formamide

To a solution of sodium hydroxide (8.0 g) in water (50 ml) was added Intermediate 1 (28.6 g), and the mixture was left standing at room temperature for 10 minutes. To this aqueous solution was added sodium 2-propylthiosulfate (43 g) in the form of powder. A pale yellow oil product was deposited immediately after the addition of sodium 2-propylthiosulfate. After the reaction mixture was extracted with ethyl acetate (200 ml), the ethyl acetate layer was dried over anhydrous sodium sulfate and concentrated under reduced pressure.

Yield: 24.9 g.

1H-NMR (in CDCl$_3$): δ7.99 & 7.95 (0.33 & 0.67H, each s), 3.78 (2H, t), 2.97 (3H, s), 2.93–2.87 (3H, m), 2.00 (3H, s), 1.27 (6H, d).

(b) N-methyl-N-[[4-[2-amino-3-(3,4-dipivaloyloxyphenyl)propionyloxy]-1-methyl-2-[(2-propyl)dithio]-1-butenyl]formamide The compound in the above step (a) (3.72 g), Compound D (7.0 g) and dimethylaminopyridine (245 mg) were dissolved in acetonitrile (30 ml). The mixed solution was ice-cooled. Dicyclohexylcarbodiimide (3.2 g) was added to the mixed solution and left standing for 3 hours with ice-cooling. In TLC (CHCl$_3$:MeOH=10:1), the spot of the compound in the above-described step (a) disappeared and converged on the spot at the Rf value of 0.7. After deposited products were removed by filtration, the filtrate was concentrated under reduced pressure, and the residue was purified by silica gel column chromatography (CHC$_3$:MeOH=50:1→40:1) to give the protected product of the title compound.

Yield: 8.26 g.

1H-NMR (in CDCl$_3$): δ7.90 (1H, s), 7.06–6.91 (3H, m), 5.01 (1H, broad d), 4.54 (1H, broad m), 4.27 & 4.15 (each 1H, each m), 3.06 (2H, d), 2.94 (3H, s), 2.92–2.86 (3H, m), 1.93 (3H, s), 1.43 (9H, s), 1.330 & 1.328 (each 9H, each s), 1.26 (6H, d).

The protected product (4.60 g) was dissolved in trifluoroacetic acid under ice-cooling. After left standing at room temperature for 15 minutes, the solution was added dropwise to a sodium hydrogen carbonate suspension (200 ml) to give a white amorphous product. The mixture was extracted with chloroform. The chloroform layer was dried over anhydrous sodium sulfate and concentrated under reduced pressure. After the colorless residue thus obtained was dissolved in ether, n-hexane was added to the ethereal solution. The mixture was concentrated under reduced pressure in a low-temperature water bath to give white powder. The powder was collected by filtration and dried under reduced pressure to give the title compound.

Yield: 3.77 g.

1H-NMR (in CDCl$_3$): δ7.91 (1H, s), 7.06 (2H, s), 6.98 (1H, s), 4.28–4.18 (2H, m), 3.70 (1H, q), 3.10–3.02 (1H, m), 2.95 (3H, s), 2.94–2.82 (4H, m), 1.96 (3H, s), 1.334 & 1,332 (each 9H, each s), 1.26 (6H, d).

(c) N-methyl-N-[4-[2-[(5-dimethylaminonaphthylsulfonyl)amino]ethylaminocarbonyloxy]-1-methyl-2-[(2-propyl)dithio]-1-butenyl]formamide To the solution of compound in the above step (a) (2.5 g) in tetrahydrofuran (15 ml) was added carbodiimidazole (1.78 g, 11 mmole) in the form of powder, and the carbodiimidazole was dissolved in a water bath at 40° C. (5 minutes). To this solution were added Compound A (2.9 g) and tetrahydrofuran (30 ml), and the mixture was stirred at room temperature for about 2 hours. After insolubles were removed by filtration, the filtrate was concentrated under reduced pressure and purified by silica gel column chromatography (CHCl$_3$:MeOH=40:1). To a solution of the fluorescent yellowish green residue thus obtained (4.95 g) in ethanol (100 ml) was added 1N hydrochloric acid (8.7 ml), and the mixture was evaporated under reduced pressure. Dissolution in ethanol and evaporation was further repeated twice. Ether was added to the residue obtained, and the resulting white powdery solid was collected by filtration and dried under reduced pressure to give the title compound.

Yield: 4.63 g.

1H-NMR (in DMSO-d$_6$): δ8.53 & 8.37 (each 1H, each d), 8.12 (1H, m), 7.79 (1H, s), 7.68 & 7.66 (each 1H, each t), 7.44 (1H, d), 4.03 (2H, t), 2.99–2.90 (9H, m), 2.82 (3H, s), 2.82–2.78 (4H, m), 1.90 (3H, s), 1.19 (6H, d).

Example 4

N-Methyl-N-[4-hydroxy-1-methyl-2-[(2-butyl)dithio]-1-butenyl]formamide

To a solution of sodium hydroxide (3.2 g) in distilled water (10 ml) was added an aqueous solution of Intermediate 1 (11.4 g), and the mixture was left standing at room temperature for 30 minutes. Sodium 2-butylthiosulfate (15 g) in the form of powder was added to the aqueous solution. Immediately after the addition, a light brown oil product was deposited. The reaction mixture was extracted with ethyl acetate (200 ml). The ethyl acetate layer was dried over anhydrous sodium sulfate and concentrated under reduced pressure. The residue thus obtained was purified by silica gel column chromatography to give a colorless oil product (6.2 g).

$^1$H-NMR (in CD$_3$OD): 7.98 & 7.92 (1H, s), 3.71 (2H, t), 2.95 (3H, s), 2.88 (2H, t), 2.70 (1H, q), 2.02 (3H, s), 1.66 (1H, m), 1.51 (1H, m), 1.25 (3H, d), 0.97 (3H, d).

Example 5

(a) N-(2-hydrxyethyl)-N-[-2-[(1-methylbutyl)dithio]vinyl]-formamide

In a solution of sodium hydroxide (1.32 g) in water (50 ml) was dissolved Intermediate 2 (3.2 g). To this solution was added sodium 1-methylbutylthiosulfate (6 g) in the form of powder with stirring. After the mixture turned white turbid, a pale yellow oil product was deposited and sedimented. The reaction was extracted with chloroform. The chloroform layer was dried over anhydrous sodium sulfate. The solvent was evaporated under reduced pressure. The residue obtained was purified by silica gel column chromatography (CHCl$_3$:MeOH=40:1→30:1).

Yield: 2.33 g.

$^1$H-NMR (in CDCl$_3$, 3:1 isomeric mixture): δ8.33 & 8.09 (0.75 & 0.25H, each s), 6.47, 6.13, 5.91 & 5.82 (0.25, 0.75, 0.75 & 0.25H, each d, J=9, 8, 8, 9 Hz), 3.82–3.74 (4H, m), 2.92 (1H, m), 2.14 (1H, broad), 1.63(1H, m), 1.45 (3H, m), 1.33 & 1.32 (3H, each d, each J=7.0 Hz), 0.92 (3H, t).

(b) N-[2-3-[(5-dimethylaminonaphthylsulfonyl)amino]-propionyloxy]ethyl]-N-[2-[(s-butyl)dithio]vinyl]formamide The compound in the above step (a) (2.31 g), Compound B (3.10 g) and dimethylaminopyridine (250 mg) were dissolved in tetrahydrofuran (30 ml). Dicyclohexylcarbodiimide (2.02 g) was added to the solution. The mixture was then left standing for 15 hours at room temperature. After white deposits were removed by filtration, the filtrate was concentrated under reduced pressure. The residue obtained was purified by silica gel column chromatography (CHCl$_3$:MeOH=10:1→8:1).

Yield: 4.77 g.

$^1$H-NMR (in CDCl$_3$, 4:1 isomeric mixture): δ8.54 & 8.30 (each 1H, each d), 8.26 & 7.91 (0.8 & 0.2H, each s), 8.25 (1H, dd), 7.60–7.51 (2H, m), 7.19 (1H, d), 6.43, 6.02, 5.87 & 5.77 (0.2, 0.8, 0.8 & 0.2H, each d, J=9, 8, 8, 9 Hz), 5.60 & 5.31 (0.8 & 0.2H, broad t), 4.15 (2H, t), 3.79 (2H, t), 3.17 (2H, q), 2.90 (7H, m), 2.45 (2H, t), 1.62 (1H, m), 1.44 (3H, m), 1.31 & 1.30 (3H, each d, each J=7 Hz), 0.91 (3H, t).

Example 6

(a) N-(carboxymethyl)-N-[2-[(1-methylbutyl)dithio]vinyl]formamide

In a solution of sodium hydroxide (1.32 g) in water (40 ml) was dissolved Intermediate 3 (2.3 g), and the resulting solution was further saturated with sodium sulfate. To this solution was added sodium 1-methylbutylthiosulfate (6 g) in the form of powder. The mixture was then stirred at room temperature for 15 minutes. The reaction was adjusted to a pH of about 2 with 4N hydrochloric acid and extracted with ethyl acetate (150 ml). After the ethyl acetate layer was dried over anhydrous sodium sulfate, and the solvent was evaporated under reduced pressure to give pale yellow crystals.

Yield: 1.80 g.

$^1$H-NMR (in CDCl$_3$, 3:1 isomeric mixture): δ8.40 & 8.37 (0.25 & 0.75H, each s), 6.96, 6.22, 5.86 & 5.69 (0.25, 0.75, 0.75 & 0.25H, each d, J=13.5, 8.5, 8.5, 13.5 Hz), 4.49 & 4.39 (1.5 & 0.5H, each s), 2.91 (1H, m), 1.63(1H, m), 1.44 (3H, m), 1.32 (3H, d), 0.92 (3H, t).

(b) N-[[[12-[(5-dimethylaminonaphthylsulfonyl)amino]ethyl]-aminocarbonyl]methyl]-N-[2-[(1-methylbutyl)dithio]vinyl]formamide Compound A (1.7 g), the compound in the above step (a) (1.5 g) and dimethylaminopyridine (120 mg) were dissolved in tetrahydrofuran (30 ml). Dicyclohexylcarbodiimide (1.23 g) was added to the solution. The mixture was then stirred at room temperature for about 15 hours. After white deposits were removed by filtration, the filtrate was concentrated under reduced pressure. The residue obtained was purified by silica gel column chromatography (CHCl$_3$:acetone=10:1→10:2).

Yield: 1.10 g.

$^1$H-NMR (in CDCl$_3$, 2:1 isomeric mixture): δ8.56 (1H, m), 8.40 & 8.31 (0.33 & 0.67H, each s), 8.27–8.21 (2H, m), 7.61–7.51 (2H, m), 7.20 (1H, d), 6.46 & 6.37 (0.33 & 0.67H, each broad), 6.96, 6.08, 5.89 & 5.82 (0.33, 0.67, 0.67 & 0.33H, each d, J=13.5, 8.0, 8.0 & 13.5 Hz), 5.40 & 5.30 (0.67 & 0.33H, each broad), 4.17 & 4.11 (0.67 & 1.33H), 3.32 & 3.04 (each 2H, each m), 2.93 (1H, m), 2.90 (6H, s), 1.61 (1H, m), 1.43 (3H, m), 1.311 & 1.306 (3H, each d, each J=7 Hz), 0.91 (3H, m).

Example 7

(a) N-(2-hydroxyethyl)-N-[1-methyl-2-(2-propyldithio)vinyl]formamide In a solution of sodium hydroxide (1.32 g) in water (40 ml) was dissolved Intermediate 4 (3.4 g). To this solution was added sodium 2-propylthiosulfate (ca. 7 g) in the form of powder, and the mixture was stirred at room temperature for 15 minutes. The reaction was extracted with chloroform. After the chloroform layer was dried with anhydrous sodium sulfate, the solvent was evaporated under reduced pressure. The residue obtained was purified by silica gel column chromatography (CHCl$_3$:MeOH=40:1→35:1).

Yield: 2.41 g.

$^1$H-NMR (in CDCl$_3$, 4:1 isomeric mixture): 8.10 & 8.08 (0.8 & 0.2H, each s), 6.20 & 6.07 (0.2 & 0.8H, each d, each J=1.0 Hz), 3.79 & 3.68 (1.6 & 0.4H, each m), 3.65 & 3.54 (1.6 & 0.4H, each t), 06 (1H, m), 2.54 & 2.22 (0.7 & 0.1H, each t), 1.96 & 1.93 (2.4 & 0.6H, each d, each J=1.0 Hz), 1.33 & 1.32 (6H, each d, each J=7.0 Hz).

$^1$H-NMR (in DMSO-d$_6$, 7:3 isomeric mixture): 8.1 & 7.97 (0.3 & 0.7H, each s), 6.13 & 6.10 (0.7 & 0.3H, each d, each J=1.0 Hz), 4.78 & 4.73 (0.3 & 0.7H, each broad t), 3.48–3.42 (4H, m), 3.10 (1H, m), 1.96 & 1.89 (2.1 & 0.9H, each d, J=1.0 Hz), 1.25 & 1.24 (6H, each d, each J=6.5 Hz).

(b) N-[2-[2-[(5-dimethylaminonaphthylsulfonyl)amino]propionyloxy]ethyl-N-[1-methyl-2-(2-propyldithio)vinyl]formamide Compound C (2.58 g), the compound in the above step (a) (1.90 g) and dimethylaminopyridine (300 mg) were dissolved in tetrahydrofuran (30 ml). Dicyclohexylcarbodiimide (1.70 g) was added to the solution. The mixture was then stirred at room temperature for about 12 hours. After white deposits were removed by filtration, the filtrate was concentrated under reduced pressure. The residue obtained was purified by silica gel column chromatography (CHCl$_3$:acetone=10:1).

Yield: 3.51 g.

$^1$H-NMR (in CDCl$_3$, 7:1 isomeric mixture): δ8.54 & 8.30 (each 1H, each d), 8.24 (1H, dd), 8.03 & 7.87 (0.87 & 0.13H, each s), 7.61–7.50 (2H, m), 7.19 (1H, d), 6.10 & 6.02 (0.13 & 0.87H, each d, each J=1.0 Hz), 5.46 & 5.34 (0.87 & 0.13H, each d, each J=8.5 Hz), 3.98 (1H, m), 3.93 & 3.87 (each 1H, each m), 3.51 (2H, m), 3.04 (1H, m), 2.88 (6H, s), 1.85 & 1.84 (1.75 & 0.25H, each d, each J=1.0 Hz), 1.30 & 1.29 (9H, each d, J=6.5 & 7.0 Hz).

Example 8

(a) N-(2-hydroxyethyl)-N-2-(2-propyldithio)-1-propenyl]formamide

In a solution of sodium hydroxide (1.3 g) in water (50 ml) was dissolved Intermediate 5 (3.4 g). To this solution was added sodium 2-propylthiosulfate (ca. 7 g) in the form of powder, and the mixture was stirred at room temperature for 0.5 hour. The reaction was extracted with chloroform. After the chloroform layer was dried with anhydrous sodium sulfate, the solvent was evaporated under reduced pressure. The residue obtained was purified by silica gel column chromatography (CHCl$_3$:MeOH=50:1→35:1).

Yield: 1.63 g.

$^1$H-NMR (in CDCl$_3$, 6:1 isomeric mixture): δ8.18 & 8.10 (0.85 & 0.15H, each s), 6.05 & 5.99 (0.85 & 0.15H, each s), 3.79 & 3.70 (1.7 & 0.3H, each m), 3.62 (2H, t), 2.97 (1H, m), 2.35 (1H, broad), 2.19 & 2.17 (2.6 & 0.4H, each s), 1.30 & 1.29 (6H, each d).

(b) N-[2-[2-[(5-dimethylaminonaphthylsulfonyl)amino]propionyloxy]ethyl-N-[2-(2-propyldithio)-1-propenyl]formamide Compound C (2.2 g), the compound in the above step (a) (1.60 g) and dimethylaminopyridine (300 mg) were dissolved in tetrahydrofuran (30 ml). Dicyclohexylcarbodiimide (1.70 g) was added to the solution. The mixture was then stirred at room temperature for about 10 hours. After white deposits were removed by filtration, the filtrate was concentrated under reduced pressure. The residue obtained was purified by silica gel column chromatography (CHCl$_3$:acetone=10:1→10:1.5).

Yield: 2.19 g.

$^1$H-NMR (in CDCl$_3$, 6:1 isomeric mixture): δ8.54 & 8.29 (each 1H, each d), 8.24 (1H, dd), 8.06 & 7.87 (0.86 & 0.14H, each s), 7.62–7.50 (2H, m), 7.20 (1H, d), 5.97 & 5.90 (0.14 & 0.86H, each d, each J=1.5 Hz), 5.45 & 5.33 (0.86 & 0.14H, each d, each J=8.5 Hz), 4.00–3.94 (2H, m), 3.87 (1H, m), 3.49 (2H, m), 2.94 (1H, m), 2.89 (6H, s), 2.14 & 2.13 (3H, each d, each J=1.0 Hz), 1.30 & 1.29 (9H, each d, J=7.5 & 6.5 Hz).

Example 9

(a) N,N'-{dithiobis[2-methyl-2,1-ethenediyl]}bis{N-[(2-hydroxy)ethyl]formamide

In a solution of sodium hydroxide (1.68 g) in water (20 ml) was dissolved Intermediate 5 (4.5 g). To this solution was added portionwise an aqueous iodine-potassium iodide solution separately prepared (0.5M). While for some time from initiating the addition, the brown color of iodine immediately disappeared as soon as the aqueous iodine-potassium iodide solution was added. The color faded gradually and finally the solution remained pale brown. At this time, the addition of the aqueous iodine-potassium iodide solution was stopped (the reaction has a pH of about 7 at this time). The reaction was saturated with sodium sulfate and extracted with chloroform. After the chloroform layer was dried with anhydrous sodium sulfate, the solvent was evaporated under reduced pressure. The residue obtained was purified by silica gel column chromatography (CHCl$_3$:ethanol=40:1→15:1).

Yield: 2.17 g.

$^1$H-NMR (in CDCl$_3$, 4:1:1 isomeric mixture): δ 8.16, 8.15 & 8.09 (0.17, 0.66 & 0.17H, each s), 6.16, 6.14 & 6.07 (0.66 & 0.17 & 0.17H, each s), 3.78 & 3.71 (1.8 & 0.17H, each m), 3.62 (2H, m), 2.58 & 2.40 (0.17 & 0.83H, each t), 2.14 (3H, m).

$^1$H-NMR (in DMSO-d$_6$, 8:5:5:2 isomeric mixture): δ8.052, 8.046 & 8.039 & 8.032 (1H, each s), 6.43, 6.37, 6.19 & 6.16 (0.4, 0.25, 0.25 & 0.1H, each d, each J=1.5 Hz), 4.82 & 4.77 (0.33 & 0.67H, t & m), 3.53–3.42 (4H, m), 2.03 (3H, m).

(b) N,N'-{dithiobis[2-methyl-2,1-ethenediyl]}bis{N-[2-[3-[(5-dimethylaminonaphthylsulfonyl)amino]propionyloxy]ethyl]formamide Compound B (4.4 g), the compound in the above step (a) (2.12 g) and dimethylaminopyridine (300 mg) were dissolved in tetrahydrofuran (40 ml). Dicyclohexylcarbodiimide (1.70 g) was added to the solution. And then the mixture was stirred at room temperature for about 16 hours. After white deposits were removed by filtration, the filtrate was concentrated under reduced pressure. The residue obtained was purified by silica gel column chromatography (CHCl$_3$:acetone=10:1→10:3) to give the title compound.

Yield: 1.66 g.

$^1$H-NMR (in CDCl$_3$): δ8.54, 8.30 & 8.23 (each 1H, each d), 8.1 (1H, m), 7.58–7.50 (2H, m), 7.18 (1H, d), 6.33–6.08 (1H, m), 5.82 (1H, broad m), 4.12 (2H, m), 3.67 (2H, m), 3.14 (2H, m), 2.89 (6H, s), 2.50 (2H, m), 2.08 (3H, m).

Example 10

(a) N-(2-hydroxyethyl)-N-[1-methyl-2-(2-Propyldithio)vinyl]-acetamide

In a solution of sodium hydroxide (1.3 g) in water (50 ml) was dissolved Intermediate 6 (3.57 g). To this solution was added sodium 2-propylthiosulfate (ca. 6 g) in the form of powder, and the mixture was stirred at room temperature for about 0.5 hour. The reaction mixture was extracted with chloroform. After the chloroform layer was dried with anhydrous sodium sulfate, the solvent was evaporated under reduced pressure. The residue obtained was purified by silica gel column chromatography (CHCl$_3$:methanol=40:1→35:1).

Yield: 2.33 g.

$^1$H-NMR (in CDCl$_3$): δ6.08 (1H, d, J=1.0 Hz), 3.81 (2H, broad), 3.73 & 3.46 (each 1H, each broad), 3.30 (1H, t), 3.05 (1H, m), 2.10 (3H, s), 1.94 (3H, J=1.0 Hz), 1.32 (6H, d, J=6.5 Hz).

(b) N-[2-[2-[(5-dimethylaminonaphthylsulfonyl)amino]propionyloxy]ethyl]-N-[1-methyl-2-(2-propyldithio)vinyl]acetamide Compound C (3.0 g), the compound in the above step (a) (2.3 g) and dimethylaminopyridine (300 mg) were dissolved in tetrahydrofuran (30 ml). Dicyclohexylcarbodiimide (1.96 g) was added to the solution. And then the mixture was stirred at room temperature for about 18 hours. After white deposits were removed by filtration, the filtrate was concentrated under reduced pressure. The residue obtained was purified by silica gel column chromatography (CHCl$_3$:acetone=10:1→9:1) to give the title compound.

Yield: 3.85 g.

$^1$H-NMR (in CDCl$_3$): δ8.54 & 8.30 (each 1H, each d), 8.23 (1H, dd), 7.59 & 7.51 (each 1H, each dd), 7.19 (1H, d), 6.05 (1H, broad s), 5.50 (1H, broad d), 3.99 (2H, m), 3.90 (1H, broad), 3.60 & 3.31 (each 1H, each broad), 3.03 (1H,.m), 2.88 (6H, s), 2.03 (3H, s), 1.84 (3H, s), 1.30 & 1.29 (9H, each d).

Example 11

(a) N-(2-hydroxyethyl)-N-[4-hydroxy-1-methyl-2-(2-propyldithio)-1-butenyl]formamide In a solution of sodium hydroxide (1.3 g) in water (50 ml) was dissolved Intermediate 7 (4.02 g). After this solution was saturated with sodium sulfate, sodium 2-propylthiosulfate (ca. 7 g) was added in the form of powder. The mixture was then stirred at room temperature for about 15 minutes. The reaction mixture was extracted with chloroform. After the chloroform layer was dried with anhydrous sodium sulfate, the solvent was evaporated under reduced pressure. The residue obtained was purified by silica gel column chromatography (CHCl₃:methanol=40:1→20:1) to give the title compound.

Yield: 3.90 g.

¹H-NMR (in CDCl₃, 2:1 isomeric mixture): δ8.03 & 8.02 (1H, each s), 3.85–3.78 (4H, m), 3.72 & 3.65 (2H, each m), 3.00–2.98 (3H, m), 2.05 & 1.99 (2 & 1H, each s), 1.28 (6H, d, J=7.0 Hz).

¹H-NMR (in DMSO-d₆, 7:3 isomeric mixture): δ7.98 & 7.87 (0.3 & 0.7H, each s), 4.82, 4.74, 4.69 & 4.65 (0.3, 0.7, 0.7 & 0.3H, each t), 3.52–3.45 (4H, m), 3.42 (2H, t), 2.96 (1H, m), 2.73 (2H, t), 1.99 & 1.92 (0.9 & 2.1H, each s), 1.21 & 1.20 (6H, each d, J=6.5 & 5.0 Hz).

(b) N-[2-[3-[(5-dimethylaminonaphthylsulfonyl)amino]propionyl)oxy]ethyl-N-[4-[3-[(5-dimethylaminonaphthylsulfonyl)amino]propionyl]oxy-1-methyl-2-(2-propyldithio)-1-butenyl]formamide Compound B (4.28 g), the compound in the above step (a) (1.80 g) and dimethylaminopyridine (300 mg) were dissolved in tetrahydrofuran (30 ml). Dicyclohexylcarbodiimide (3.00 g) was added to the solution. And then the mixture was stirred at room temperature for about 12 hours. After white deposits were removed by filtration, the filtrate was concentrated under reduced pressure. The residue obtained was purified by silica gel column chromatography (CHCl₃:acetone=10:1→10:2) to give the title compound.

Yield: 3.96 g.

¹H-NMR (in CDCl₃, 4:1 isomeric mixture): δ8.54 (2H, dd), 8.30–8.22 (4H, m), 7.95 & 7.94 (0.8 & 0.2H, each s), 7.18 (2H, dd), 5.82, 5.68 5.47 & 5.40 (0.2, 0.8, 0.8 & 0.2H, each broad t), 4.15 & 4.07 (3.6 & 0.4H, each m), 3.66 & 3.59 (1.6 & 0.4H, each broad), 3.16 (4H, m), 2.94–2.88 (15H, m), 2.50 (4H, m), 1.98 & 1.94 (2.4 & 0.6H, each s), 1.25 (6H, d).

Example 12

(a) N-[2-(tert-butyloxycarbonylamino)ethyl]-N-[4-hydroxy-1-methyl-2-[(1-propyl)dithio]-1-butenyl]formamide In a solution of sodium hydroxide (2.0 g) in water (50 ml) was dissolved Intermediate 8 (9.2 g), and the mixture was left standing at room temperature for 5 minutes. Sodium 2-propylthiosulfate (8 g) in the form of powder was added to the aqueous solution. Immediately after the addition, a pale brown oil product was deposited. The reaction mixture was extracted with ethyl acetate (100 ml). The ethyl acetate layers were combined, dried over anhydrous sodium sulfate and evaporated under reduced pressure. The residue obtained was purified by silica gel column chromatography to give the title compound of which amino group was protected with Boc group.

Yield: 9.07 g.

¹H-NMR (in CD₃OD, 5:2 isomeric mixture): δ8.00 & 7.93 (0.29 & 0.71H, each s), 3.72 (2H, t), 3.53 (2H, broad m), 3.23 (2H, t), 2.89 (2H, t), 2.67 (2H, t), 2.06 & 2.01 (2.14 & 0.86H, each s), 1.67 (2H, m), 1.43 (9H, s), 0.99 (3H, m).

(b) N-(2-aminoethyl)-N-[4-[2-[(5-dimethylaminonaphthylsulfonyl)amino]ethylaminocarbonyloxy]-1-methyl-2-[(1-propyl)dithio)-1-butenyl]formamide hydrochloride In a solution of the compound in the above step (a) (9.07 g) in tetrahydrofuran (50 ml) was dissolved carbodiimidazole (4.05 g) in a water bath at 40° C. To this solution was added Compound A (7.6 g), and the mixture was stirred at room temperature for 24 hours. After insolubles were removed by filtration, the filtrate was evaporated under reduced pressure. The residue obtained was purified by silica gel column chromatography to give the title compound of which amino group was protected with Boc group.

Yield: 15.3 g.

¹H-NMR (in CD₃OD, 3:1 isomeric mixture): δ8.56, 8.33, 8.19 (each 1H, each d), 7.97 & 7.87 (0.25 & 0.75H, each s), 7.58 (2H, m), 7.29 (1H, d), 4.14 (2H, t), 3.49 & 3.19 (each 2H, each broad t), 3.10 (2H, t), 2.95–2.88 (4H, m), 2.89 (6H, s), 2.65 (2H, m), 2.00 & 1.95 (2.1 & 0.9H, each s), 1.64 (2H, m), 1.41 (9H, s), 0.97 (3H, m).

The Boc-protected derivative (15.3 g) was added with trifluoroacetic acid (40 ml) and dissolved under ice-cooling. And then the mixture was left standing at room temperature for about 10 minutes. The trifluoroacetic acid solution was slowly added dropwise to an aqueous sodium hydrogen carbonate suspension (200 ml). Yellow fluorescent viscous powder was deposited. The mixture was extracted with ethyl acetate (200 ml). The ethyl acetate layer was washed with water and dried over anhydrous sodium sulfate. The solvent was then evaporated under reduced pressure. The residue obtained was purified by silica gel column chromatography (CHCl₃:methanol=45:1→20:1) to give 11.12 g of a residue. It was dissolved in ethanol and concentrated after 1N hydrochloric acid (18.6 ml) was added. The residue having ethanol added thereto was concentrated again and added dropwise to a mixed solvent of ether:hexane=2:1 (400 ml). Pale yellow powdery solid obtained was collected by filtration and dried under reduced pressure to give the title compound.

Yield: 9.17 g.

¹H-NMR (in CD₃OD, 10:1 isomeric mixture): δ8.56 & 8.51 (each 1H, each d), 8.24 (1H, dd), 7.96 & 7.89 (0.9 & 0.1H, each s), 7.70–7.67 (2H, m), 7.56 (1H, broad d), 4.20 (2H, t), 3.71 (2H, t), 3.16 (2H, t), 3.12 (2H, t), 3.09 (6H, s), 2.98 (2H, t), 2.91 (2H, t), 2.70 (2H, t), 2.08 & 2.00 (2.7 & 0.3H, each s), 1.67 (2H, q), 0.99 (3H, t).

Example 13

(a) N-[2-(tert-butyloxycarbonylamino)ethyl]-N-[4-hydroxy-1-methyl-2-[(2-propyl)dithio]-1-butenyl]formamide In a solution of sodium hydroxide (2.0 g) in water (30 ml) was dissolved Intermediate 8 (9.4 g), and the mixture was left standing at room temperature for 5 minutes. Sodium 2-propylthiosulfate (9.0 g) in the form of powder was added to the aqueous solution. Immediately after the addition, a pale yellow oil product was deposited. The reaction mixture was extracted with chloroform (100 ml). The aqueous layer was further extracted with chloroform (100 ml). The chloroform layers were combined, dried with anhydrous sodium sulfate and evaporated under reduced pressure. The residue was purified by silica gel column chromatography to give the title compound of which amino group was protected with Boc group.

Yield: 6.81 g.

¹H-NMR (in CD₃OD, 5:2 isomeric mixture): δ8.00 & 7.96 (0.28 & 0.72H, each s), 3.70 (2H, t), 3.54 & 3.25 (each 2H, each broad t), 2.96 (1H, m), 2.89 (2H, t), 2.06 & 2.01 (2.1 & 0.9H, each s), 1.43 (9H, s), 1.28 (6H, d).

¹H-NMR (in CDCl₃, 3:1 isomeric mixture): δ8.05 & 7.97 (0.75 & 0.25H, each s), 3.80 (2H, t), 3.78 (2H, t), 3.57 (2H, broad), 3.31 (2H, broad t), 2.95 (1H, m), 2.88 (2H, t), 2.03 & 1.99 (2.25 & 0.75H, s), 1.45 & 1.43 (9H, each s), 1.28 (6H, d).

(b) N-(2-aminoethyl)-N-[4-[2-[(5-dimethylaminonaphthylsulfonyl)amino]ethylaminocarbonyloxy]-1-methyl-2-[(2-propyl)-dithio)-1-butenyl]formamide hydrochloride In a solution of the compound in the above step (a) (3.8 g) in tetrahydrofuran (20 ml) was dissolved carbonyldiimidazole (1.7 g) in the form of powder in a water bath at 40°

C. To this solution was added Compound A (2.95 g), and the mixture was stirred at room temperature for about 5 hours. After insolubles were removed by filtration, the filtrate was evaporated under reduced pressure. The residue obtained was purified by silica gel column chromatography to give the Boc-protected derivative of the title compound (CHCl$_3$:methanol=80:1→50:1).

Yield: 6.68 g.

$^1$H-NMR (in CD$_3$OD, 7:3 isomeric mixture): δ8.56, 8.32, 8.18 (each 1H, each d), 7.99 & 7.91 (0.3 & 0.7H, each s), 7.59 (2H, m), 7.27 (1H, d), 4.12 (2H, t), 3.51 (2H, broad), 3.21 (2H, broad), 3.10 (2H, t), 2.96–2.89 (5H, m), 2.88 (6H, s), 2.00 & 1.94 (2.1 & 0.9H, each s), 1.41 (9H, s), 1.26 (6H, d).

The Boc-protected derivative (3.3 g) was added with trifluoroacetic acid (15 ml) and dissolved under ice-cooling. The mixture was then left standing at room temperature for about 10 minutes. The trifluoroacetic acid solution was slowly added dropwise to an aqueous sodium hydrogen carbonate suspension (100 ml). Yellow fluorescent viscous powder was deposited. The mixture was extracted with ethyl acetate (100 ml). After the ethyl acetate layer was washed with water, it was partitioned with 1N hydrochloric acid (50 ml). The aqueous layer was adjusted to a pH of 9 with sodium sulfate and partitioned with chloroform (100 ml). After the chloroform layer was dried with anhydrous sodium sulfate, the solvent was evaporated under reduced pressure. The residue obtained was purified by silica gel column chromatography (CHCl$_3$:methanol=40:1→20:1) to give 2.39 g of a residue. It was dissolved in ethanol (150 ml) and concentrated after 1N hydrochloric acid (4.0 ml) was added. The residue having ethanol added thereto was concentrated again and added dropwise to ether (200 ml). Pale yellow powdery solid obtained was collected by filtration and dried under reduced pressure to give the title compound.

Yield: 2.24 g.

$^1$H-NMR (in CD$_3$OD, 10:1 isomeric mixture): δ8.57 (1H, d), 8.36 (1H, d), 8.20 (1H, d), 8.08 & 7.99 (0.1 & 0.9H, each s), 7.63–7.59 (2H, m), 4.18 (2H, t), 3.72 (2H, t), 3.18 (2H, t), 3.12 (2H, t), 3.02–2.96 (3H, m), 2.94 (6H, s), 2.90 (2H, t), 2.70 & 2.00 (3H, each s), 1.28 (6H, d).

Example 14

(a) N-[2-(tert-butyloxycarbonylamino)ethyl]-N-[4-hydroxy-1-methyl-2-[(2-butyl)dithio]-1-butenyl]formamide In a solution of sodium hydroxide (2.0 g) in water (50 ml) was dissolved Intermediate 8 (9.2 g). Sodium 2-butylthiosulfate (8 g) in the form of powder was added to the aqueous solution. Immediately after the addition, a pale brown oil product was deposited. After the reaction mixture was partitioned with ethyl acetate (200 ml), the ethyl acetate layer was dried over anhydrous sodium sulfate and evaporated under reduced pressure. The residue obtained was purified by silica gel column chromatography (only CHCl$_3$→CHCl$_3$:methanol=40:1) to give the title compound of which amino group was protected with Boc group.

Yield: 4.1 g.

$^1$H-NMR (in CD$_3$OD, 3:1 isomeric mixture): δ8.00 & 7.96 (0.25 & 0.75H, each s), 3.70 (2H, t), 3.53 (2H, broad t), 3.24 (2H, broad t), 2.90 (2H, t), 2.76 (1H, m), 2.06 & 2.01 (2.1 & 0.9H, each s), 1.67 & 1.52 (each 1H, each m), 1.43 (9H, s), 1.27 (3H, d), 0.98 (3H, d).

(b) N-(2-aminoethyl)-N[4-[2-[(5-dimethylaminonaphthylsulfonyl)amino]ethylaminocarbonyloxy]-2-[(2-butyl)dithio]-1-butenyl]formamide hydrochloride In a solution of the compound in the above step (a) (4.1 g) in tetrahydrofuran (30 ml) was dissolved carbonyldiimidazole (1.8 g) in the form of powder, and the mixture was left standing at room temperature for 1 hour. To this solution was added Compound A (2.95 g), and the mixture was stirred at room temperature for about hours. After insolubles were removed by filtration, the filtrate was evaporated under reduced pressure. The residue obtained was purified by silica gel column chromatography to give the Boc-protected derivative of the title compound (CHCl$_3$:methanol=80:1→50:1).

Yield: 2.92 g.

$^1$H-NMR (in DMSO-d$_6$, 4:1 isomeric mixture): δ8.46 (1H, d), 8.26 (1H, d), 8.09 (1H, d), 7.95 (1H, broad s), 7.79 (1H, s), 7.63–7.57 (2H, m), 7.26 (1H, d), 7.01 (1H, broad), 6.79 (1H, broad), 4.01 & 3.95 (1.5 & 0.5H, each t), 3.36 (2H, m), 3.04 (2H, q), 2.98 (2H, q), 2.83 (6H, s), 2.8–2.72 (5H, m), 1.92 & 1.87 (2.4 & 0.6H, s), 1.57 & 1.44 (each 1H, each m), 1.36 (9H, s), 1.18 (3H, d), 0.89 (3H, t).

The Boc-protected derivative (2.8 g) was ice-cooled, added with trifluoroacetic acid (30 ml) and dissolved under ice-cooling. And then the mixture was left standing at room temperature for about 15 minutes. The trifluoroacetic acid solution was slowly added dropwise to an aqueous sodium hydrogen carbonate suspension (150 ml). Yellow fluorescent viscous powder was deposited. The mixed solution was extracted with chlroform (100 ml). After the chloroform layer was washed with water and dried with anhydrous sodium sulfate, the solvent was evaporated under reduced pressure. The residue obtained was purified by silica gel column chromatography (CHCl$_3$:methanol=50:1→20:1) to give 2.15 g of a foam. After the foam was dissolved in ethanol (150 ml) and added with 1N hydrochloric acid (3.5 ml), the mixture was concentrated. The residue having ethanol added thereto was concentrated again and dissolved in chloroform (20 ml). The solution was added dropwise to ether (250 ml). Pale yellow powdery solid obtained was collected by filtration and dried under reduced pressure to give the title compound.

Yield: 1.82 g.

$^1$H-NMR (in DMSO-d$_6$, 6:1 isomeric mixture): δ8.49, 8.30 & 8.10 (each 1H, each d), 8.05–7.97 (4H, broad), 7.85 (1H, s), 7.61 (2H, m), 7.29 (1H, d), 7.11 (1H, broad), 4.02 (2H, t), 3.61 (2H, t), 2.99 (2H, q), 2.88 (2H, broad), 2.85 (6H, s), 2.85–2.74 (5H, m), 1.96 & 1.89 (2.6 & 0.4H, each s), 1.55 & 1.46 (each 1H, each m), 1.19 (3H, d), 0.90 (3H, t).

Example 15

(a) N-[2-(tert-butyloxycarbonylamino)ethyl]-N-[4-hydroxy-1-methyl-2-[(1-pentyl)dithio]-1-butenyl]formamide In a solution of sodium hydroxide (4.0 g) in water (50 ml) was dissolved Intermediate 8 (18.4 g), and the mixture was left standing at room temperature for 5 minutes. Sodium 1-pentylthiosulfate (20 g) in the form of powder was added to the aqueous solution. Immediately after the addition, a pale brown oil product was deposited. The reaction mixture was partitioned with chloroform (100 ml). Then the aqueous layer was further partitioned with chloroform (100 ml). These chloroform layers were combined, dried with anhydrous sodium sulfate and evaporated under reduced pressure. The residue obtained was purified by silica gel column chromatography to give the title compound of which amino group was protected with Boc group.

Yield: 18.22 g.

$^1$H-NMR (in DMSO-d$_6$, 3:1 isomeric mixture): δ7.94 & 7.83 (0.25 & 0.75H, each s), 6.92 & 6.83 (0.25 & 0.75H, each broad), 4.71 & 4.68 (0.75 & 0.25H, each t), 3.52 & 3.47

(1.5 & 0.5H, q & m), 3.36 (2H, broad), 3.04 (2H, t), 2.74 (2H, t), 2.65 (2H, t), 1.98 & 1.91 (2.25 & 0.75H, each s), 1.57 (2H, m), 1.37 (9H, s), 1.28 (4H, m), 0.85 (3H, m).

(b) N-(2-aminoethyl)-N-[4-[2-[(5-dimethylaminonaphthyl-sulfonyl)amino]ethylaminocarbonyloxy]-1-methyl-2-[(1-pentyl)dithio)-1-butenyl]formamide hydrochloride In a solution of the compound in the above step (a) (6.1 g) in tetrahydrofuran (25 ml) was dissolved carbonyldiimidazole (2.56 g) in the form of powder in a water bath at 40° C. To this solution was added Compound A (4.7 g), and the mixture was stirred at room temperature for about 10 hours. After insolubles were removed by filtration, the filtrate was evaporated under reduced pressure. The residue obtained was purified by silica gel column chromatography to give the Boc-protected derivative of the title compound ($CHCl_3$:methanol=80:1→40:1).

Yield: 5.75 g.

$^1$H-NMR (in $CD_3OD$, 3:1 isomeric mixture): δ8.56, 8.31, 8.18 (each 1H, each d), 7.89 & 7.87 (0.25 & 0.75H, each s), 7.58 (2H,q), 7.28 (1H, d), 4.14 (2H, t), 3.49 (2H, broad), 3.19 (2H, t), 3.10 (2H, t), 2.95–2.88 (4H, m), 2.88 (6H, s), 2.67 (2H, t), 2.00 & 1.95 (2.25 & 0.75H, t), 1.62 (2H, m), 1.41 (9H, s), 1.33 (4H, m), 0.90 (3H, t).

The Boc-protected derivative (5.66 g) was ice-cooled, added with trifluoroacetic acid (30 ml) and dissolved under ice-cooling. And then the mixture was left standing at room temperature for about 40 minutes. The trifluoroacetic acid solution was slowly added dropwise to an aqueous sodium hydrogen carbonate suspension (150 ml). Yellow fluorescent viscous powder was then deposited. The mixed solution was partitioned with chlroform (100 ml). After the chloroform layer was washed with water and dried with anhydrous sodium sulfate, the solvent was evaporated under reduced pressure. The residue obtained was purified by silica gel column chromatography to give 4.54 g of a residue. After the residue was dissolved in ethanol (150 ml) and added with 1N hydrochloric acid (7.3 ml), the mixture was concentrated. The residue having ethanol added thereto was concentrated again and dissolved in trichloromethane (15 ml). The solution was added dropwise to ether (150 ml). Pale yellow viscous solid obtained was solidified in hexane. The powdery solid obtained was collected by filtration and dried under reduced pressure to give the title compound.

Yield: 4.55 g.

$^1$H-NMR (in DMSO-$d_6$, 10:1 isomeric mixture): δ8.48, 8.28 & 8.09 (each 1H, each d), 8.04–7.96 (3H, broad), 7.82 (1H, s), 7.61 (2H, m), 7.28 (1H, d), 7.14 (1H, t), 4.03 (2H, t), 3.59 (2H, broad), 2.99 (2H, q), 2.90–2.78 (12H, m), 2.67 (2H, t), 1.97 & 1.90 (2.7 & 0.3H, s), 1.55 (1H, m), 1.32 –1.24 (4H, m), 0.85 (3H, m).

Example 16

(a) N-[2-(tert-butyloxycarbonylamino)ethyl]-N-[4-hydroxy-1-methyl-2-[(1-methylbutyl)dithio]-1-butenyl]formamide In a solution of sodium hydroxide (4.0 g) in water (120 ml) was dissolved Intermediate 8 (18.4 g), and the mixture was left standing at room temperature for 5 minutes. Sodium 1-methylbutylthiosulfate (20 g) in the form of powder was added to the aqueous solution. Immediately after the addition, a yellowish brown viscous oil product was floated. After the reaction mixture was partitioned with chloroform, the oily components were extracted and washed with water. The combined chloroform layers were dried with anhydrous sodium sulfate and evaporated under reduced pressure. The residue obtained was purified by silica gel column chromatography ($CHCl_3$:MeOH=40:1→30:1) to give the title compound of which amino group was protected with Boc group.

Yield: 18.92 g.

$^1$H-NMR (in DMSO-$d_6$, 4:1 isomeric mixture): δ7.95 & 7.86 (0.2 & 0.8H, each s), 6.92 & 6.83 (0.2 & 0.8H, each broad), 4.71 & 4.66 (0.8 & 0.2H, each t), 3.51 & 3.46 (1.6 & 0.4H, each q), 3.37 (2H, broad), 3.06 (2H, q), 2.81 (1H, m), 2.74 (2H, t), 1.98 & 1.90 (2.4 & 0.6H, each s), 1.54 (1H, m), 1.37 (10H, m & s), 1.20 (3H, d), 0.87 (3H, t).

(b) N-(2-aminoethyl)-N-[4-[2-[(5-dimethylaminonaphthyl-sulfonyl)amino]ethylaminocarbonyloxy]-1-methyl-2-[(1-methylbutyl)dithio)-1-butenyl]formamide hydrochloride In a solution of the compound in the above step (a) (4.3 g) in tetrahydrofuran (15 ml) was dissolved carbonyldiimidazole (1.8 g) in the form of powder, and the mixture was heated in a water bath at 50° C. for about 20 minutes. To this solution was added Compound A (3.3 g), and the mixture was stirred at room temperature for about 12 hours. After insolubles and deposits were removed by filtration, the filtrate was evaporated under reduced pressure. The residue obtained was purified by silica gel column chromatography to give the Boc-protected derivative of the title compound ($CHCl_3$:methanol=80:1→60:1).

Yield: 3.40 g.

$^1$H-NMR (in $CD_3OD$, 5:2 isomeric mixture): δ8.56, 8.31, 8.18 (each 1H, each d), 7.98 & 7.90 (0.29 & 0.71H, each d), 7.58 (2H, q), 7.27 (1H, d), 4.12 (2H, t), 3.50 (2H, m), 3.20 (2H, t), 3.10 (2H, t), 2.95 & 2.91 (4H, m), 2.88 (6H, s), 2.80 (1H, m), 2.00 & 1.94 (1.14 & 0.86H, each s), 1.58 (1H, m), 1.48–1.38 (12H, m), 1.25 (3H, d), 0.91 (3H, t).

The Boc-protected derivative (3.22 g) was ice-cooled, added with trifluoroacetic acid (20 ml) and dissolved under ice-cooling, and the mixture was left standing at room temperature for about 40 minutes. The trifluoroacetic acid solution was slowly added dropwise to an aqueous sodium hydrogen carbonate suspension (150 ml). A yellow fluorescent viscous product was then deposited. This mixed solution was partitioned with chloroform (100 ml). After the chloroform layer was washed with water and dried with anhydrous sodium sulfate, the solvent was evaporated under reduced pressure. The residue obtained was purified by silica gel column chromatography to give 2.70 g of a residue. After the residue was dissolved in ethanol (150 ml) and added with 1N hydrochloric acid (7.3 ml), the mixture was concentrated. The residue having ethanol added thereto was concentrated again and dissolved in chloroform (15 ml). The solution was added dropwise to ether (150 ml). Pale yellow powdery solid obtained was collected by filtration and dried under reduced pressure to give the title compound.

Yield: 2.48 g.

$^1$H-NMR (in $CD_3OD$, 9:1 isomeric mixture): δ8.57, 8.31 & 8.18 (each 1H, each d), 8.07 & 7.99 (0.1 & 0.9H, each s), 7.58 (2H, q), 7.28 (1H, d), 4.18 (2H, t), 3.71 (2H, t), 3.18 (2H, t), 3.12 (2H, t), 2.98 (2H, t), 2.92–2.84 (9H, m), 2.08 & 2.00 (2.7 & 0.3H, each s), 1.58 (1H, m), 1.50–1.40 (3H, m), 1.28 (3H, d), 0.92 (3H, t).

Example 17

(a) N-[2-(tert-butyloxycarbonylamino)ethyl]-N-[4-hydroxy-2-[(3-pentyl)dithio]-1-butenyl]formamide In a solution of sodium hydroxide (4.0 g) in water (100 ml) was dissolved Intermediate 8 (18.4 g), and the mixture was left standing at room temperature for 5 minutes. Sodium 3-pentylthiosulfate (20 g) in the form of powder was added to the aqueous solution. Immediately after the addition, a yellowish brown viscous oil product was deposited. After the reaction mixture was partitioned with chloroform, the oily components were extracted and washed with water. The combined chloroform layers were dried with anhydrous sodium sulfate and evaporated under reduced pressure. The residue obtained was purified by silica gel column chromatography (CHCl$_3$:methanol=80:1→30:1) to give the title compound of which amino group was protected with Boc group.

Yield: 15.3 g.

$^1$H-NMR (in DMSO-d$_6$, 4:1 isomeric mixture): δ7.95 & 7.85 (0.2 & 0.8H, each s), 6.86 & 6.82 (0.2 & 0.8H, each broad), 4.71 & 4.67 (0.8 & 0.2H, each t), 3.52 & 3.47 (1.6 & 0.4H, each q), 3.37 (2H, broad), 3.05 (2H, q), 2.75 (2H, t), 2.58 (1H, m), 1.98 & 1.90 (2.4 & 0.6H, each s), 1.54 (4H, m), 1.37 (9H, s), 0.91 (6H, m).

(b) N-(2-aminoethyl)-N-[4-[2-[(5-dimethylaminonaphthylsulfonyl)amino]ethylaminocarbonyloxy]-1-methyl-2-[(3-pentyl)dithio)-1-butenyl]formamide hydrochloride In a solution of the compound in the above step (a) (6.1 g) in tetrahydrofuran (25 ml) was dissolved carbonyldiimidazole (2.6 g) in the form of powder in a water bath at 40° C. To this solution was added Compound A (4.7 g), and the mixture was stirred at room temperature for about 13 hours. After insolubles and deposits were removed by filtration, the filtrate was evaporated under reduced pressure. The residue obtained was purified by silica gel column chromatography to give the Boc-protected derivative of the title compound (CHCl$_3$:methanol=80:1→40:1).

Yield: 6.54 g.

$^1$H-NMR (in CD$_3$OD, 4:1 isomeric mixture): δ8.56, 8.32, 8.18 (each 1H, each d), 7.90 & 7.89 (0.2 & 0.8H, each s), 7.58 (2H, q), 7.28 (1H, d), 4.13 (2H, t), 3.49 (2H, broad), 3.20 (2H, t), 3.10 (2H, t), 2.95 & 2.91 (4H, m), 2.88 (6H, s), 2.57 (1H, m), 2.00 & 1.94 (2.4 & 0.6H, each s), 1.61 (4H, m), 1.43 & 1.41 (9H, s), 0.96 (6H, t).

The Boc-protected derivative (6.0 g) was ice-cooled, added with trifluoroacetic acid (30 ml) and dissolved under ice-cooling. And then the mixture was left standing at room temperature for about 15 minutes. The trifluoroacetic acid solution was slowly added dropwise to an aqueous sodium hydrogen carbonate suspension (200 ml). A yellow fluorescent viscous product was then deposited. This mixed solution was partitioned with chloroform. After the chloroform layer was washed with water and dried with anhydrous sodium sulfate, the solvent was evaporated under reduced pressure. The residue obtained was purified by silica gel column chromatography (CHCl$_3$+CHCl$_3$:MeOH=30:1→ 15:1) to give 7.20 g of a residue. After the residue was dissolved in 2-propanol (200 ml) and added with 1N hydrochloric acid (11.5 ml), the mixture was concentrated. After the residue was dissolved in chloroform, the solution was added dropwise to ether (150 ml). As the deposit was viscous, the ether layer was discarded, and then the residue was solidified by the addition of hexane. Pale yellow powdery solids obtained were collected by filtration and dried under reduced pressure to give the title compound.

Yield: 7.02 g.

$^1$H-NMR (in DMSO-d$_6$, 9:1 isomeric mixture): δ8.47, 8.27 & 8.09 (each 1H, each d), 8.04–7.97 (4H, broad), 7.86 & 7.83 (0.1 & 0.9H), 7.61 (2H, m), 7.27 (1H, d), 7.12 (1H, broad), 4.04 (2H, t), 3.59 (2H, broad t), 2.99 (2H, broad q), 2.92–2.78 (12H, m), 2.60 (1H, m), 1.96 (3H, s), 1.53 (4H, m), 0.90 (6H, t).

Example 18

(a) N-[2-(tert-butyloxycarbonylamino)ethyl]-N-[4-hydroxy-2-cyclohexyldithio-1-methyl-1-butenyl]formamide To a solution of sodium hydroxide (2.0 g) in water (80 ml) was added Intermediate 8 (9.2 g), and the mixture was left standing at room temperature for 5 minutes. Sodium cyclohexylthiosulfate (10 g) in the form of powder was added to the aqueous solution. Immediately after the addition, a pale yellow oil product was deposited. After the reaction mixture was partitioned with chloroform (100 ml), the aqueous layer was further partitioned with chloroform (100 ml). The combined chloroform layers were dried with anhydrous sodium sulfate and evaporated under reduced pressure. The residue obtained was purified by silica gel column chromatography to give the title compound of which amino group was protected with the Boc group.

Yield: 1.81 g.

$^1$H-NMR (in DMSO-d$_6$, 3:1 isomeric mixture): δ7.95 & 7.85 (0.25 & 0.75H, each s), 6.92 & 6.82 (0.25 & 0.75H, each broad), 4.68 & 4.65 (0.75 & 0.25H, each broad t), 3.51 & 3.46 (1.5 & 0.5H, each q), 3.38 (2H, broad), 3.07 (2H, broad q), 2.76–2.68 (3H, m), 1.98 (3H, s), 1.90, 1.68 & 1.53 (5H, m), 1.37 (9H, s), 1.28–1.14 (5H, m).

(b) N-(2-aminoethyl)-N-[4-[2-[(5-dimethylaminonaphthylsulfonyl)amino]ethylaminocarbonyloxy]-1-methyl-2-cyclohexyldithio-1-butenyl]formamide hydrochloride In a solution of the compound prepared in the above step (a) (1.77 g) in tetrahydrofuran (15 ml) was dissolved carbonyldiimidazole (0.72 g) in the form of powder in a water bath at 40° C. To this solution was added Compound A (1.5 g), and the mixture was stirred at room temperature for about 15 hours. After insolubles and deposits were removed by filtration, the filtrate was evaporated under reduced pressure. The residue obtained was purified by silica gel column chromatography to give the Boc-protected derivative of the title compound (CHCl$_3$:MeOH=80:1→30:1).

Yield: 2.71 g.

$^1$H-NMR (in CD$_3$OD): δ8.56, 8.32 & 8.19 (each 1H, each d), 7.88 (1H, d), 7.58 (2H, q), 7.27 (1H, d), 4.12 (2H, t), 3.30 (2H, broad), 3.22 (2H, t), 3.10 (2H, t), 2.96 & 2.90 (4H, m), 2.88 (6H, s), 2.70 (1H, m), 1.99 (3H, s), 1.98–1.94 (2H, m), 1.75 (2H, m), 1.60 (1H, m), 1.41 (9H, s), 1.34–1.28 (5H, m).

The Boc-protected derivative (2.64 g) was ice-cooled, added with trifluoroacetic acid (30 ml) and dissolved under ice-cooling. And then the mixture was left standing in a water bath at 50° C. for about 15 minutes. The trifluoroacetic acid solution was slowly added dropwise to an aqueous sodium hydrogen carbonate suspension (150 ml). A yellow fluorescent viscous product was then deposited. This mixed solution was partitioned with chlroform (100 ml). After the chloroform layer was washed with water and dried with anhydrous sodium sulfate, the solvent was evaporated under reduced pressure. The residue obtained was purified by silica gel column chromatography (CHCl$_3$:methanol=60:1→15:1) to give 1.76 g of a residue. After the residue was dissolved in ethanol (150 ml) and added with 1N hydrochloric acid (2.8 ml), the mixture was concentrated. The residue was added with ethanol and concentrated again. The residue was dissolved in chloroform (10 ml) and added dropwise to ether (150 ml). The pale yellow powdery product was collected by filtration and dried under reduced pressure to give the title compound.

Yield: 1.24 g.

$^1$H-NMR (in CD$_3$OD, 12:1 isomeric mixture): δ8.57, 8.39 & 8.21 (each 1H, each d), 8.07 & 7.99 (0.08 & 0.92H, each s), 7.62 (2H, q), 7.38 (1H, d), 4.17 (2H, t), 3.72 (2H, t), 3.19 (2H, t), 3.12 (2H, t), 2.98 (2H, t), 2.96 (6H, s), 2.92 (2H, t), 2.76 (1H, m), 2.07 (3H, s), 1.98 (2H, m), 1.77 (2H, m), 1.62 (1H, m), 1.38–1.24 (5H, m).

$^1$H-NMR (in DMSO-d$_6$): δ8.48, 8.28 & 8.09 (each 1H, each d), 7.99 (4H, broad), 7.85 (1H, s), 7.61 (2H, m), 7.28 (1H, d), 7.10 (1H, broad), 4.02 (2H, t), 3.60 (2H, t), 2.99

(2H, q), 2.89 (2H, t), 2.85 (6H, s), 2.84–2.79 (4H,m), 2.74 (1H, m), 1.96 (3H, s), 1.89 (2H, m), 1.67 (2H, m), 1.53 (1H, m), 1.30–1.15 (5H, m).

Example 19

(a) N-[2-(tert-butyloxycarbonylamino)ethyl]-N-[4-hydroxy-1-methyl-2-[(1-dodecyl)dithio]-1-butenyl]formamide To a solution of sodium hydroxide (2.0 g) in water (70 ml) was added Intermediate 8 (9.2 g), and the mixture was left standing at room temperature for 5 minutes. Sodium 1-dodecyl-thiosulfate (6 g) in the form of powder was added to the aqueous solution. Sonication was conducted because of the low dissolution rate of the powder. Along with the dissolution of it, a yellowish brown amorphous product was deposited. After the reaction was partitioned with chloroform (100 ml), the aqueous layer was further partitioned with chloroform (100 ml). The combined chloroform layers were dried with anhydrous sodium sulfate and evaporated under reduced pressure. The residue obtained was purified by silica gel column chromatography to give the title compound of which amino group was protected with Boc group.

Yield: 4.11 g.

$^1$H-NMR (in DMSO-$d_6$, 4:1 isomeric mixture): 7.95 & 7.83 (0.2 & 0.8H, each s), 6.88 & 6.79 (0.2 & 0.8H, each broad), 4.68 (1H, broad t), 3.53 & 3.48 (1.6 & 0.4H, each q), 3.36 (2H, broad), 3.05 (2H, broad), 2.74 (2H, t), 2.65 (2H, t), 1.98 & 1.91 (2.4 & 0.63H, each s), 1.98 & 1.91 (2.4 & 0.63H, each s), 1.56 (2H, m), 1.37 (9H, s), 1.32–1.24 (18H, m), 0.86 (3H, t).

(b) N-(2-aminoethyl)-N-[4-[2-[(5-dimethylaminonaphthylsulfonyl)amino]ethylaminocarbonyloxy]-1-methyl-2-dodecyldithio-1-butenyl]formamide hydrochloride In a solution of the compound prepared in the above step (a) (4.07 g) in tetrahydrofuran (30 ml) was dissolved carbonyldiimidazole (1.4 g) in the form of powder, and the mixture was left standing at room temperature for about 4 hours. To this solution was added Compound A (2.6 g), and the mixture was stirred at room temperature for about 16 hours. After insolubles and deposits were removed by filtration, the filtrate was evaporated under reduced pressure. The residue obtained was purified by silica gel column chromatography to give the Boc-protected derivative of the title compound (CHCl$_3$:methanol=80:1→50:1).

Yield: 5.20 g.

$^1$H-NMR (in CD$_3$OD, 5:2 isomeric mixture): δ8.56, 8.31 & 8.18 (each 1H, each d), 7.97 & 7.87 (0.29 & 0.71H, each s), 7.58 (2H, q), 7.27 (1H, d), 4.14 (2H, t), 3.49 (2H, broad), 3.19 (2H, t), 3.10 (2H, t), 2.95–2.88 (4H, m), 2.88 (6H, s), 2.67 (2H, t), 2.00 & 1.95 (2.14 & 0.86H, each s), 1.61 (2H, m), 1.41 (9H, s), 1.38–1.24 (18H, m), 0.90 (3H, t).

The Boc-protected derivative (5.25 g) was ice-cooled, added with trifluoroacetic acid (30 ml) and dissolved under ice-cooling. And then the mixture was left standing at room temperature for 0.5 hour. The trifluoroacetic acid solution was slowly added dropwise to an aqueous sodium hydrogen carbonate suspension (150 ml). A yellow fluorescent viscous product was then deposited. The mixed solution was partitioned with chloroform (100 ml). After the chloroform layer was washed with water and dried with anhydrous sodium sulfate, the solvent was evaporated under reduced pressure. The residue obtained was purified by silica gel column chromatography (CHCl$_3$:methanol=50:1→20:1) to give 3.56 g of a residue. After the residue was dissolved in ethanol (150 ml) and added with 1N hydrochloric acid (4.9 ml), the mixture was concentrated. The residue was added with ethanol and concentrated again. The residue was dissolved in chloroform (10 ml) and added dropwise to ether (150 ml). A pale yellow amorphous deposit was deposited. After the ethereal layer was discarded, the deposit was solidified with hexane. The powdery solid obtained was collected by filtration and dried under reduced pressure to give the title compound.

Yield: 3.30 g.

$^1$H-NMR (in CD$_3$OD, 10:1 isomeric mixture): δ8.57, 8.36 & 8.19 (each 1H, each d), 8.06 & 7.96 (0.1 & 0.9H, each s), 7.60 (2H, q), 7.34 (1H, d), 4.19 & 4.15 (1.8 & 0.2H, each t), 3.76 & 3.71 (0.2 & 1.8H, each t), 3.17 (2H, t), 3.12 (2H, t), 2.97 (2H, t), 2.93 (6H, s), 2.91 (2H, t), 2.72 (2H, m), 2.07 & 2.00 (2.7 & 0.3H, each s), 1.63 (2H, m), 1.39 (2H, m), 1.38–1.26 (18H, m), 0.89 (3H, t).

Example 20

(a) N-[2-(dimethylamino)ethyl]-N-[4-hydroxy-1-methyl-2-[(1-methylbutyl)dithio]-1-butenyl]formamide In a solution of sodium hydroxide (1.0 g) in water (50 ml) was dissolved Intermediate 9 (2.4 g), and the resulting solution was saturated with sodium chloride. Sodium 1-methyl-butylthiosulfate (ca. 8 g) in the form of powder was added to the aqueous solution. With stirring at room temperature for about 15 minutes, no oily products were deposited. After the reaction was partitioned with chloroform, the chloroform layer was dried with anhydrous sodium sulfate and evaporated under reduced pressure to give the title compound.

$^1$H-NMR (in CDCl$_3$, 4:1 isomeric mixture): δ8.03 & 8.02 (0.2 & 0.8H, each s), 3.79 (2H, t), 3.6–3.4 (2H, broad), 2.87 (2H, t), 2.78 (1H, m), 2.53 (2H, broad), 2.23 & 2.20 (4.8 & 1.2H, each s), 2.04 & 2.02 (2.4 & 0.6H, each s), 1.59 (1H, m), 1.48–1.36 (3H, m), 1.27 (3H, d), 0.91 (3H, m).

(b) N-[2-(dimethylamino)ethyl]-N-[4-[2-[(5-dimethylaminonaphthylsulfonyl)amino]propionyloxy]-1-methyl-2-[(1-methylbutyl)dithio]-1-butenyl]formamide hydrochloride In a solution of the residue obtained in the above step (a), Compound C (2.0 g) and dimethylaminopyridine (300 mg) in tetrahydrofuran (30 ml) was dissolved dicyclohexylcarbodiimide (1.34 g), and the mixture was stirred at room temperature for about 3 hours. After white deposits were removed by filtration, the filtrate was concentrated under reduced pressure. The residue obtained was purified by silica gel column chromatography (CHCl$_3$:MeOH=40:1→20:1) to give 2.95 g of a fluorescent yellow amorphous product. After the product was dissolved in ethanol and added with 1N hydrochloric acid (4.6 ml), the solvent was evaporated under reduced pressure. This procedure was repeated twice. The residue was next dissolved in chloroform and concentrated again to give the title compound as a fluorescent solid.

Yield: 2.70 g.

$^1$H-NMR (in DMSO-$d_6$, 6:1 isomeric mixture): δ8.62 (1H, d), 8.47, 8.28 & 8.11 (each 1H, each d), 8.06 & 7.85 (0.14 & 0.86H, each s), 7.61 (2H, q), 7.27 (1H, d), 3.9–3.8 (3H, m), 3.72 (2H, broad t), 3.15 (2H, broad t), 2.84 (6H, s), 2.81 & 2.80 (5.14 & 0.86H, each s), 2.79 (1H, m), 2.65 (2H, broad t), 1.94 & 1.83 (2.57 & 0.43H, each s), 1.49 (1H, m), 1.44–1.3 (3H, m), 1.20 (3H, d), 1.13 (3H, d), 0.87 (3H, t).

Example 21

(a) N-[2-(1-pyrrolidino)ethyl]-N-[4-hydroxy-1-methyl-2-[(1-methylbutyl)dithio]-1-butenyl]formamide In a solution of sodium hydroxide (1.32 g) in water (50 ml) was dissolved Intermediate 10 (3.2 g), and the resulting solution was saturated with sodium chloride. Sodium 1-methyl-butylthiosulfate (ca. 8 g) in the form of powder was added to the aqueous solution. On stirring the mixture at room temperature, oily products were deposited. After 15 minutes, the reaction was partitioned with chloroform. After the chloroform layer was washed with water and dried with anhydrous sodium sulfate, the solvent was evaporated under reduced pressure to give the title compound.

(b) N-[2-(1-pyrrolidino)ethyl]-N-[4-[2-[(5-dimethylaminonaphthylsulfonyl)amino]propionyloxy]-1-methyl-2-[(1-methylbutyl)dithio]-1-butenyl]formamide hydrochloride The amorphous residue (3.4 g) obtained in the above step (a), Compound C (3.03 g) and dimethylaminopyridine (300 mg) were dissolved in tetrahydrofuran (30 ml). In this solution was dissolved dicyclohexylcarbodiimide (1.98 g), and the mixture was stirred at room temperature for about 3 hours. After white deposits were removed by filtration, the filtrate was concentrated under reduced pressure. The residue obtained was purified by silica gel column chromatography ($CHCl_3$:methanol=30:1→20:1) to give 3.10 g of a fluorescent yellow amorphous product. After the product was dissolved in ethanol and added with 1N hydrochloric acid (4.7 ml), the solvent was evaporated under reduced pressure. This procedure was repeated twice. The residue obtained was next dissolved in chloroform and concentrated again to give a fluorescent solid as the title compound.

Yield: 2.95 g.

$^1$H-NMR (in DMSO-$d_6$, 5:1 isomeric mixture): δ8.62 (1H, d), 8.48, 8.30 & 8.11 (each 1H, each d), 8.07 & 7.84 (0.17 & 0.83H, each s), 7.61 (2H, q), 7.28 (1H, d), 3.9–3.8 (3H, m), 3.72 (2H, broad t), 3.56 (2H, broad), 3.22 (2H, broad), 3.00 (2H, broad), 2.84 (7H, m), 2.64 (2H, broad), 1.99 (2H, broad), 1.95 (3H, s), 1.85 (2H, m), 1.49 (1H, m), 1.44–1.3 (3H, m), 1.19 (3H, d), 1.14 (3H, d), 0.87 (3H, t).

Example 22

N,N'-{dithiobis[2-[(2-hydroxy)ethyl]-1-methy-2,1-ethenediyl]}bis{N-[2-(tertbutyloxycarbonylaminoethyl]formamide An aqueous iodine-potassium iodide solution was prepared by adding iodine (1.3 g) to a solution of potassium iodide (3.4 g) in distilled water (100 ml). At the same time, Intermediate 8 (3.7 g) was dissolved in distilled water (350 ml) and added with 1N hydrochloric acid (21 ml). To this solution was slowly added dropwise the aqueous iodine-potassium iodide solution at room temperature. After the addition of the aqueous iodine-potassium iodide solution was completed, the mixture was stirred for 15 minutes and then partitioned with ethyl acetate (50 ml). The ethyl acetate layer was further washed with an aqueous potassium iodide solution and dried over anhydrous sodium sulfate. And then the solvent was evaporated under reduced pressure. The residue obtained was purified by silica gel column chromatography to give the title compound as a colorless solid (1.95 g).

$^1$H-NMR (in $CD_3OD$): δ8.02 & 7.92 (1H, s), 3.72 (2H, m), 3.51 (2H, broad m), 3.20 (2H, broad t), 2.78 (2H, broad t), 2.07–2.03 (3H, m), 1.43 (9H, s).

Example 23

N[(2-hydroxy)ethyl]-N-[2-[(2-propyl)dithio]ethenyl]formamide

To a solution of sodium hydroxide (3.2 g) in distilled water (50 ml) was added Intermediate 2 (8.2 g), and the mixture was left standing at room temperature for 10 minutes. Sodium 2-propylthiosulfate (22 g) in the form of powder was added to the aqueous solution. Immediately after the addition, a pale yellow oily product was deposited. The reaction was partitioned with chloroform (100 ml). After the chloroform layer was dried with anhydrous sodium sulfate, the solvent was evaporated under reduced pressure. The residue obtained was purified by silica gel column chromatography to give 75 g of the title compound.

$^1$H-NMR (in $CDCl_3$): δ8.33 (1H, s), 6.14 (1H, d), 5.91 (1H, d), 3.75 (2H, t), 3.09 (1H, m), 1.33 (3H, s), 1.32 (3H, s).

Example 24

(a) N-(2-hydroxyethyl)-N-[2-(isobutyrylthio)vinyl]formamide

In a solution of sodium hydroxide (1.32 g) in water (30 ml) was dissolved Intermediate 2 (3.2 g). To the mixed solution ice-cooled, dioxane (20 ml) was added. And then the mixed solution of isobutyryl chloride (1.60 g) and dioxane (10 ml) was added in one portion. The reaction mixture immediately after the addition had a pH of about 7. The reaction was extracted with chloroform (200 ml). After the chloroform layer was washed twice with water and dried with anhydrous sodium sulfate, the solvent was evaporated under reduced pressure. The residue obtained was purified by silica gel column chromatography ($CHCl_3$:methanol= 60:1→40:1) to give the title compound.

Yield: 2.59 g.

$^1$H-NMR (in $CDCl_3$, 4:1 isomeric mixture): δ8.34 & 8.12 (0.8 & 0.2H, each s), 6.81, 6.42, 6.33 & 6.30 (0.2, 0.8, 0.8 & 0.2H, each d, J=9, 8.5, 8.5 & 9 Hz), 3.79 (2H, t), 3.75 (2H, m), 2.78 (1H, m), 2.13 & 1.75 (0.8 & 0.2H, each broad t), 1.24 & 1.23 (6H, each d).

(b) N [2-[[3-[(5-dimethylaminonaphthylsulfonyl)amino] propionyloxy]ethyl]-N-[2-(isobutyrylthio)vinyl]formamide The compound (2.59 g) obtained in the above step (a), Compound B (3.23 g) and dimethylaminopyridine (250 mg) were dissolved in tetrahydrofuran (30 ml). In this solution was dissolved dicyclohexylcarbodiimide (2.3 g), and the mixture was left standing at room temperature for about 13 hours. After white deposits were removed by filtration, the filtrate was concentrated under reduced pressure. The residue obtained was purified by silica gel column chromatography ($CHCl_3$:acetone=10:1) to give the title compound.

Yield: 1.72 g.

$^1$H-NMR (in $CDCl_3$, 5:1 isomeric mixture): δ8.55 & 8.30 (each 1H, each d), 8.25 (1H, s), 8.24 (1H, m), 7.60–7.51 (2H, m), 7.19 (1H, d), 6.72 & 6.30 (0.17 & 1.83H, d & m), 5.58 & 5.29 (0.87 & 0.17H, broad t), 4.13 & 4.09 (1.83 & 0.17H, each t), 3.78 (2H, t), 3.15 (2H, q), 2.89 (6H, s), 2.77 (1H, m), 2.44 (2H, t.), 1.23 & 1.22 (6H, each d).

Example 25

(a) N-(2-hydroxyethyl)-N-[2-(pivaloylthio)vinyl]formamide

In a solution of sodium hydroxide (1.32 g) in water (30 ml) was dissolved Intermediate 2 (3.2 g). To the mixed solution ice-cooled, dioxane (20 ml) was added. And then the mixed solution of pivaloyl chloride (1.81 g) and dioxane (10 ml) was added in one portion. The reaction mixture immediately after the addition had a pH of about 7. The reaction was extracted with chloroform (150 ml). After the chloroform layer was washed twice with water and dried with anhydrous sodium sulfate, the solvent was evaporated under reduced pressure. The residue obtained was purified by silica gel column chromatography ($CHCl_3$:methanol= 60:1→40:1) to give the title compound.

Yield: 3.04 g.

$^1$H-NMR (in CDCl$_3$, 4:1 isomeric mixture): δ8.36 & 8.12 (0.8 & 0.2H, each s), 6.82, 6.42, 6.34 & 6.31 (0.2, 0.8, 0.8 & 0.2H, each d, J=9, 8.5, 8.5 & 9 Hz), 3.79 (2H, q), 3.75 (2H, m), 2.13 & 1.71 (0.8 & 0.2H, each broad t), 1.27 (9H, s).

$^1$H-NMR (in DMSO-d$_6$, 6:5 isomeric mixture): δ8.33 & 8.07 (0.55 & 0.45H, each s, —N—CHO), 6.88, 6.77, 6.03 & 5.97 (0.45, 0.55, 0.45 & 0.55H, each d, J=9, 8.5, 9 & 8.5 Hz, —CH=CH—), 3.67 & 3.60 (each 1H, each t, —O—CH$_2$CH2—), 3.45 (2H, m, —O—CH$_2$CH$_2$—), 1.22 (9H, s, —C(CH$_3$)$_3$).

(b) N-[2-[[3-[(5-dimethylaminonaphthylsulfonyl)amino]propionyl]oxy]ethyl]-N-[2-(pivaloylthio)vinyl]formamide The compound (2.31 g) obtained in the above step (a), Compound B (2.65 g) and dimethylaminopyridine (250 mg) were dissolved in tetrahydrofuran (30 ml). In this solution was dissolved dicyclohexylcarbodiimide (2.0 g), and the mixture was left standing at room temperature for about 12 hours. After white deposits were removed by filtration, the filtrate was concentrated under reduced pressure. The residue obtained was purified by silica gel column chromatography (CHCl$_3$:acetone=10:1) to give the title compound.

Yield: 2.11 g.

$^1$H-NMR (in CDCl$_3$, 5:1 isomeric mixture): δ8.55 & 8.30 (each 1H, each d), 8.26 (1H, s), 8.24 (1H, m), 7.60–7.51 (2H, m), 7.19 (1H, d), 6.74 & 6.31 (0.4 & 1.6H, d & m), 5.58 & 5.28 (0.8 & 0.2H, broad t), 4.13 & 4.09 (1.6 & 0.4H, each t), 3.78 (2H, t), 3.14 (2H, q), 2.89 (6H, s), 2.46 & 2.43 (0.4 & 1.6H, each t), 1.26 & 1.25 (9H, each s).

Example 26

(a) N-(2-hydroxyethyl)-N-[2-(benzoylthio)vinyl]formamide

In a solution of sodium hydroxide (1.76 g) in water (30 ml) was dissolved Intermediate 2 (4.2 g). To the mixed solution ice-cooled, dioxane (20 ml) was added. And then the mixed solution of benzoyl chloride (2.81 g) and dioxane (10 ml) was added in one portion. The reaction mixture immediately after the addition had a pH of about 7. The reaction was extracted with chloroform. After the chloroform layer was washed twice with water and dried with anhydrous sodium sulfate, the solvent was evaporated under reduced pressure. The residue obtained was purified by silica gel column chromatography (CHCl$_3$:methanol=60:1→40:1) to give the title compound.

Yield: 4.14 g.

$^1$H-NMR (in CDCl$_3$, 3:1 isomeric mixture): δ8.43 & 8.16 (0.75 & 0.25H, each s), 7.77, 7.63 & 7.50 (2, 1 & 2H, each m), 6.92, 6.58, 6.54 & 6.52 (0.25, 0.75, 0.25 & 0.75H, each d, J=9, 8.5, 8.5 & 9 Hz), 3.81 (4H, m), 2.18 & 1.87 (0.75 & 0.25H, each broad t).

$^1$H-NMR (in DMSO-d$_6$, 10:9 isomeric mixture): δ8.43 & 8.12 (0.53 & 0.47H, each s), 7.97, 7.74 & 7.60 (2, 1 & 2H, each m), 7.00, 6.91, 6.29 & 6.18 (0.47, 0.53, 0.47 & 0.53H, each d, each J=9 Hz), 4.93 & 4.86 (0.47 & 0.53H, each broad t), 3.74 & 3.69 (each 1H, each t), 3.52 & 3.48 (each 1H, each q).

(b) N-[2-[[3-[(5-dimethylaminonaphthylsulfonyl)amino]propionyl]oxy]ethyl]-N-[2-(benzoylthio)vinyl]formamide The compound (2.5 g) obtained in the above step (a), Compound B (2.92 g) and dimethylaminopyridine (250 mg) were dissolved in tetrahydrofuran (20 ml). In this solution was dissolved dicyclohexylcarbodiimide (2.2 g), and the mixture was left standing at room temperature for about 14 hours. After white deposits were removed by filtration, the filtrate was concentrated under reduced pressure. The residue obtained was purified by silica gel column chromatography (CHCl$_3$:acetone=50:3→10:1) to give the title compound.

Yield: 3.70 g.

$^1$H-NMR (in CDCl$_3$, 3:1 isomeric mixture): δ8.54 (1H, d), 8.34 & 7.99 (0.75 & 0.25H, each s), 8.29 (1H, d), 8.23 (1H, dd), 7.95 (2H, m), 7.65–7.47 (5H, m), 7.18 (1H, d), 6.83, 6.55, 6.53 & 6.39 (0.25, 0.75, 0.25 & 0.75H, each d, J=9, 8, 9 & 8 Hz), 5.57 & 5.27 (0.75 & 0.25H, broad t), 4.16 & 4.12 (1.5 & 0.5H, each t), 3.83 (2H, t), 3.14 (2H, q), 2.89 (6H, s), 2.46 & 2.43 (0.5 & 1.5H, each t).

Example 27

(a) N-(2-hydroxy-1-propyl)-N-[1-methyl-2-(pivaloylthio)vinyl]formamide

In a solution of sodium hydroxide (1.6 g) in water (30 ml) was dissolved Intermediate 11 (4.3 g). To the mixed solution ice-cooled, dioxane (20 ml) was added. And then the mixed solution of pivaloyl chloride (2.0 g) and dioxane (10 ml) was added in one portion (the reaction mixture immediately after the addition had a pH of 7). After the reaction was extracted with chloroform. The chloroform layer was washed with water and dried with anhydrous sodium sulfate, the solvent was evaporated under reduced pressure. The residue obtained was purified by silica gel column chromatography (CHCl$_3$:methanol=50:1→40:1) to give the title compound.

Yield: 2.47 g.

$^1$H-NMR (in CDCl$_3$, 7:1 isomeric mixture): δ8.10 & 8.04 (0.87 & 0.13H, each s), 6.45 (1H, d, J=1 Hz), 3.98 (1H, broad), 3.54, 3.42 & 3.31 (0.87, 0.87 & 0.26H, dd, dd & m), 2.66 (1H, broad), 2.08 & 2.04 (2.62 & 0.38H, d, J=1.5 Hz), 1.24 (9H, s), 1.21 (3H, d).

(b) N-[2-[[3-[(5-dimethylaminonaphthylsulfonyl)amino]propionyl]oxy]1-propyl]-N-[1-methyl-2-(pivaloylthio)vinyl]formamide Compound B (2.6 g), the compound (2.1 g) obtained in the above step (a) and dimethylaminopyridine (300 mg) were dissolved in tetrahydrofuran (30 ml). In this solution was dissolved dicyclohexylcarbodiimide (1.68 g), and the mixture was left standing at room temperature for about 12 hours. After white deposits were removed by filtration, the filtrate was concentrated under reduced pressure. The residue obtained was purified by silica gel column chromatography (CHCl$_3$:acetone=10:1) to give the title compound.

Yield: 3.51 g.

$^1$H-NMR (in CDCl$_3$, 4:1 isomeric mixture): δ8.55, 8.33 & 8.29 (each 1H, each d), 8.04 & 7.93 (0.8 & 0.2H, each s), 7.58 & 7.53 (each 1H, each 7.20 (1H, d), 6.63 & 6.38 (0.2 & 0.8H, each s), 5.71 & 5.65 (0.8 & 0.2H, each broad t), 4.91 & 4.84 (0.8 & 0.2H, each m), 3.67 & 3.52 (each 1H, each dd), 3.12 (2H, m), 2.90 (6H, s), 2.46 & 2.41 (0.4 & 1.6H, each m), 2.03 & 2.02 (0.6 & 2.4H, each s), 1.23, 1.19 & 1.17 (12H, s, s & d).

Example 28

(a) N-[2-(dimethylamino)ethyl]-N-[4-hydroxy-1-methyl-2-(pivaloylthio)-1-butenyl]formamide In a solution of sodium hydroxide (1.86 g) in water (20 ml) was dissolved Intermediate 9 (4.31 g). To the mixed solution ice-cooled, dioxane (20 ml) was added. And then the mixed solution of pivaloyl chloride (1.80 g) and dioxane (10 ml) was added in one portion (the reaction mixture immediately after the addition had a pH of 9). The reaction was partitioned with chloroform (150 ml). After the chloroform layer was washed with water and dried with anhydrous sodium sulfate, the solvent was evaporated under reduced pressure to give the title compound.

(b) N-[2-(dimethylamino)ethyl]-N-[4-[2-[(5-dimethylaminonaphthylsulfonyl)amino]propionyl]-1-methyl-2-(pivaloylthio)-1-butenyl]formamide hydrochloride The compound (2.3 g) obtained in the above step (a), Compound C (2.3 g) and dimethylaminopyridine (300 mg) were dissolved in tetrahydrofuran (30 ml). In this solution was dissolved dicyclohexylcarbodiimide (1.50 g), and the mixture was stirred at room temperature for about 3 hours. After white deposits were removed by filtration, the filtrate was concentrated under reduced pressure. The residue obtained was purified by silica gel column chromatography ($CHCl_3$:acetone=10:2→10:3). The purified product (1.24 g) was dissolved in ethanol and added with 1N hydrochloric acid (2.0 ml), and the mixture was concentrated udder reduced pressure. This procedure was repeated twice. The residue was next dissolved in chloroform and concentrated under reduced pressure again to give a fluorescent amorphous solid as the title compound.

Yield: 1.10 g.

$^1$H-NMR (in DMSO-$d_6$, 9:1 isomeric mixture): δ10.12 (1H, broad), 8.60 (1H, d), 8.48 & 8.28 (each 1H, each d), 8.10 (1H, dd), 8.02 & 7.67 (0.1 & 0.9H, s), 7.60 (2H, q), 7.28 (1H, d), 3.89–3.78 (3H, m), 3.68 (2H, broad t), 2.99 (2H, broad), 2.84 (6H, s), 2.78 & 2.77 (each 3H, each s), 2.42 (2H, broad t), 2.04 & 2.00 (2.7 & 0.3H, each s), 1.17 (9H, s), 1.12 (3H, d).

Example 29

(a) N-[(4-amino-2-methyl-5-pyrimidyl)methyl]-N-[4-hydroxy-1-methyl-2-[(tetrahydrofurfuryl)dithio]-1-butenyl]formamide This compound was synthesized in accordance with the report (1) by Matsukawa et al. (supra). In brief, sodium tetrahydrofurfurylthiosulfate (22 g) in the form of powder was added to an aqueous yellow solution obtained by adding a suspension of thiamine hydrochloride (23.6 g) in water (20 ml) to an aqueous solution (20 ml) of sodium hydroxide (8.4 g). Pale yellow amorphous product thus deposited was washed with water, dissolved in ethyl acetate and partitioned with a saturated aqueous sodium sulfate solution containing sodium hydrogen carbonate. The ethyl acetate layer was concentrated under reduced pressure, And then white solids deposited were collected by filtration and dried under reduced pressure to give the title compound.

$^1$H-NMR (in $CDCl_3$): δ8.0 (1H, s), 7.8 (1H, s), 3.88 (1H, m), 3.81 (1H, m), 3.70 (1H, m), 3.63 (2H, t), 2.85 (2H, m), 2.57 (2H, d), 2.39 (3H, s), 2.09 (3H, s), 2.01 (1H, m), 1.90 (2H, m), 1.56 (1H, m).

(b) N-[(4-amino-2-methyl-5-pyrimidyl)methyl]-N-[4-[2-amino-3-(3,4-dipivaloyloxyphenyl)propionyl]oxy-1-methyl-2-[(tetrahydrofurfuryl)dithio]-1-butenyl]formamide Compound D (3.5 g), the compound (3.0 g) obtained in the above step (a) and dimethylaminopyridine (97 mg) were dissolved in a mixture of acetonitrile:tetrahydrofuran=30:20 ml. In this solution was dissolved dicyclohexylcarbodiimide (1.50 g) under ice-cooling, and the mixture was stirred for about 3 hours. After white deposits were removed by filtration, the filtrate was concentrated under reduced pressure. Pale yellow amorphous product as the residue obtained was purified by silica gel column chromatography ($CHCl_3$:methanol=40:1) to give the Boc-protected derivative of the title compound.

Yield: 4.07 g.

The Boc-protected derivative (3.80 g) was added with trifluoroacetic acid (30 ml) and dissolved under ice-cooling. After the derivative was dissolved, the solution was left standing at room temperature for about 15 minutes and added dropwise to a saturated suspension of sodium hydrogen carbonate prepared separately (250 ml). After the mixture was partitioned with ethyl acetate (ca. 100 ml), the ethyl acetate layer was washed with an aqueous sodium sulfate solution and dried over anhydrous sodium sulfate. The solvent was evaporated under reduced pressure to give a white solid residue (3.13 g). After the residue was dissolved in ethanol (ca. 50 ml) and added with 1N hydrochloric acid (4.2 ml), the solvent was removed under reduced pressure. To the amorphous product thus obtained was added ethanol (100 ml) again, and the solvent was evaporated again under reduced pressure to give amorphous product. Ether and hexane were added to the residue, and white powder obtained was collected by filtration and dried under reduced pressure to give the title compound.

Yield: 2.94 g.

$^1$H-NMR (in $CD_3OD$): δ7.96 (1H, s), 7.85 (1H, s), 7.23–7.13 (3H, m), 4.33 (1H, m), 4.29 (1H, m), 4.15 (1H, m), 3.88 (1H, m), 3.81 (1H, m), 3.70 (1H, m), 3.21 (2H, m), 2.93 (2H, m), 2.63 (2H, m), 2.41 (3H, s), 2.04 (3H, s), 2.00 (1H, m), 1.90 (2H, m), 1.57 (1H, m), 1.34 & 1.33 (18H, each s).

Example 30

(a) N-[(4-amino-2-methyl-5-pyrimidyl)methyl]-N-[4-hydroxy-1-methyl-2-[(2-propyl)dithio]-1-butenyl]formamide Sodium isopropylthiosulfate (22 g) in the form of powder was added to an aqueous yellow solution obtained by adding a suspension of thiamine hydrochloride (23.6 g) in water (20 ml) to an aqueous solution (20 ml) of sodium hydroxide (8.4 g). Pale yellow amorphous product deposited was washed with water, dissolved in ethyl acetate and partitioned with a saturated aqueous sodium sulfate solution containing sodium hydrogen carbonate. The ethyl acetate layer was concentrated under reduced pressure, and white solids deposited were collected by filtration and dried under reduced pressure to give 12.5 g of the title compound.

$^1$H-NMR (in $CDCl_3$): δ8.02 (1H, s), 7.84 (1H, s), 3.61 (2H, t), 2.84 (2H, t), 2.61 (1H, m), 2.38 (3H, s), 2.10 (3H, s), 1.10 (6H, d).

(b) N-[(4-amino-2-methyl-5-pyrimidyl)methyl]-N-[4-[2-amino-3-(3,4-dipivaloyloxyphenyl)propionyl]oxy-1-methyl-2-[(2-propyl)dithio]-1-butenyl]formamide hydrochloride The compound (2.3 g) obtained in the above step (a), Compound D (2.8 g), and dimethylaminopyridine (100 mg) were dissolved in acetonitrile and ice-cooled. In this solution was dissolved dicyclohexylcarbodiimide (1.30 g), and the mixture was left standing under ice-cooling for 3 hours. After white deposits were removed by filtration, the filtrate was concentrated under reduced pressure. The residue obtained was purified by silica gel column chromatography ($CHCl_3$:methanol=60:1→40:1) to give the Boc-protected derivative of the title compound.

Yield: 4.50 g.

$^1$H-NMR (in $CDCl_3$): δ7.93 & 7.81 (each 1H, each s), 7.06–6.92 (3H, m), 4.52 (1H, broad d), 4.15 (2H, broad d), 3.16 (2H, broad t), 2.88 (2H, broad), 2.59 (1H, m), 2.44 (3H, s), 1.96 (3H, s), 1.42 (6H, s), 1.33 (9H, s), 1.10 (6H,d).

The Boc-protected derivative (3.61 g) was dissolved in trifluoroacetic acid (20 ml) under ice-cooling. After the solution was left standing at room temperature for about 15 minutes, it was added to a sodium hydrogen carbonate suspension (200 ml). White amorphous product was deposited. The mixture was partitioned with ethyl acetate. The aqueous layer was partitioned with ethyl acetate. The combined ethyl acetate layers were further partitioned with 0.5N hydrochloric acid. The aqueous layer obtained was adjusted to a pH of 8–9 with aqueous sodium hydrogen carbonate and partitioned with ethyl acetate. The ethyl acetate layer was dried over anhydrous sodium sulfate and evaporated under reduced pressure (3.04 g). The residue was dissolved in ethanol (150 ml) and added with 1N hydrochloric acid (4.3 ml), and the solvent was removed under reduced pressure. To the residue obtained was added the same amount of ethanol, and the mixture was concentrated again to amorphous product. To the product was added a small amount of ether, and the mixture was added dropwise to hexane (200 ml). White powder deposited was collected by filtration and dried under reduced pressure to give the title compound.

Yield: 3.09 g.

$^1$H-NMR (in CD$_3$OD): δ7.99 & 7.87 (each 1H, each s), 7.23–7.13 (3H, m), 4.3 (1H, t), 4.3 & 4.2 (each 1H, each m), 3.22 & 3.21 (each 1H, each d), 2.93 (1H, m), 2.70 (1H, m), 2.41 (3H, s), 2.05 (3H, s), 1.34 (18H, s), 1.12 (6H, d)

(c) N-[(4-amino-2-methyl-5-pyrimidyl)methyl]-N-[4-[2-[(5-dimethylaminonaphthyl)amino]ethylaminocarbonyl]oxy-1-methyl-2-[(2-propyl)dithio]-1-butenyl]formamide In a solution of the compound obtained in the above step (a) (3.57 g) in tetrahydrofuran (30 ml) was dissolved carbonyldiimidazole (1.63 g) in the form of powder, and the mixture was left standing at room temperature for about 15 minutes. To this solution was added Compound A (2.95 g) in the form of powder, and the mixture was stirred at room temperature for 13 hours. After insolubles were removed by filtration, and the filtrate was evaporated under reduced pressure. The residue obtained was purified by silica gel column chromatography (CHCl$_3$:methanol=80:1→30:1) to give the title compound.

Yield: 6.17 g.

$^1$H-NMR (in DMSO-d$_6$): δ8.46 & 8.26 (each 1H, each d), 8.12 (1H, broad), 8.09 (1H, dd), 7.91 & 7.85 (each 1H, each s), 7.62 & 7.58 (each 1H, each dd), 7.25 (1H, d), 7.09 (1H, broad t), 6.79 (2H, broad), 4.37 (2H, broad), 3.91 (2H, t), 3.00 (2H, q), 2.83 (8H, m), 2.78 (2H, t), 2.61 (1H, m), 2.24 & 1.99 (each 3H, each s), 1.02 (6H, d, J=6.5 Hz).

Example 31

(a) N-methyl-N-[[4-[2-amino-3-(3,4-di-O-pivaloylphenyl) propionyl]oxy-1-methyl-2-[(1-propyl)dithio]-1-butenyl]formamidehydrochloride This compound was synthesized by the same method as described in Example 29.

(b) N-[(4-amino-2-methyl-5-pyrimidyl)methyl]-N-[4-[2-[(5-dimethylaminonaphthyl)amino]ethylaminocarbonyl]oxy-1-methyl-2-[(1-propyl)dithio]-1-butenyl]formamide In a solution of the compound obtained in the above step (a) (3.57 g) in tetrahydrofuran (20 ml) was dissolved carbonyldiimidazole (1.63 g) in the form of powder, and the mixture was left standing at room temperature for about 15 minutes. To this solution was added Compound A (2.95 g) in the form of powder, and the mixture was stirred at room temperature for 15 hours. After insolubles were removed by filtration, the filtrate was evaporated under reduced pressure. The residue obtained was purified by silica gel column chromatography (CHCl$_3$:methanol=60:1→40:1) to give the title compound.

Yield: 5.73 g.

$^1$H-NMR (in DMSO-d$_6$): δ8.46 & 8.26 (each 1H, each d), 8.14 (1H, broad), 8.09 (1H, dd), 7.88 & 7.84 (each 1H, each s), 7.62 & 7.58 (each 1H, each dd), 7.25 (1H, d), 7.10 (1H, broad t), 6.77 (2H, broad), 4.37 (2H, broad), 3.93 (2H, t), 3.00 (2H, q), 2.83 (8H, m), 2.77 (2H, t), 2.33 (2H, t), 2.24 & 1.99 (each 3H, each s), 1.40 (2H, m), 0.84 (3H, t).

Example 32

(a) N-methyl-N-[[4-[2-amino-3-(3,4-di-O-pivaloylphenyl) propionyl]oxy-1-methyl-2-[(1-methylbutyl)dithio]-1-butenyl]formamide hydrochloride This compound was synthesized by the same method as described in Example 29.

(b) N-[(4-amino-2-methyl-5-pyrimidyl)methyl]-N-[4-[2-[(5-dimethylaminonaphthyl)amino]ethylaminocarbonyl]oxy-1-methyl-2-[(1-methylbutyl)dithio]-1-butenyl]formamide hydrochloride In a suspension of the compound obtained in the above step (a) (2.5 g) in tetrahydrofuran (15 ml) was dissolved carbonyldiimidazole (1.17 g), and the mixture was left standing at room temperature for 1 hour. To this solution was added Compound A (2.2 g), and the mixture was stirred at room temperature for about 16 hours. After insolubles and deposits were removed by filtration, the filtrate was evaporated under reduced pressure. The residue obtained was purified by silica gel column chromatography (CHCl$_3$:methanol=60:1→40:1). The residue (4.37 g) obtained was dissolved in chloroform and added with a solution of 4N hydrochloric acid in dioxane (1.6 ml). The mixture was concentrated under reduced pressure. The residue was dissolved in chloroform and added dropwise to ether. White to greenish white fluorescent powder obtained was collected by filtration and dried under reduced pressure to give the title compound.

Yield: 3.93 g.

$^1$H-NMR (in DMSO-d$_6$): δ9.29 (1H, broad), 8.48 & 8.29 (each 1H, each d), 8.25 (2H, broad), 8.23 (1H, s), 8.09 (1H, dd), 8.03 (1H, broad t), 7.97 (1H, s), 7.62 (2H, m), 7.29 (1H, d), 7.16 (1H, broad t), 4.48 (2H, broad), 3.96 (2H, t), 3.01 (2H, q), 2.85 (6H, s), 2.81 (4H, m), 2.65 (1H, m), 2.02 (3H, s), 1.36–1.24 (4H, m), 1.05 (3H, d), 0.83 (3H, t).

(c) N-[(4-amino-2-methyl-5-pyrimidyl)methyl]-N-[4-[3-[(5-dimethylaminonaphthylsulfonyl)amino]propionyl]oxy-1-methyl-2-[(1-methylbutyl)dithio]-1-butenyl]formamide hydrochloride The solution of the sodium salt of Compound B (4.0 g) in water (40 ml) was saturated with sodium sulfate. This aqueous solution was adjusted to a pH of ca. 3 with 4N hydrochloric acid, partitioned with chloroform to extract a fluorescent substance. After the chloroform layer was dried with anhydrous sodium sulfate, the solvent was evaporated under reduced pressure. The fluorescent residue obtained (2.73 g), dimethylaminopyridine (250 mg) and the compound prepared in the above step (a) (3.26 g) were dissolved in the mixture of tetrahydrofuran (15 ml) and acetonitrile (10 ml). Dicyclohexylcarbodiimide (1.86 g) was added, and the resulting solution was left standing at room temperature for about 15 hours. After white insolubles were removed by filtration, the filtrate was evaporated under reduced pressure. The residue obtained was dissolved in chloroform and purified by silica gel column chromatography (CHCl$_3$:methanol=60:1→40:1). The purified product (4.00 g) obtained was dissolved in chloroform and added with a solution of 4N hydrochloric acid in dioxane (1.45 ml), and the mixture was concentrated under reduced pressure. The residue obtained was dissolved in chloroform and added dropwise to ether. Pale green powdery crystals were collected by filtration and dried under reduced pressure to give the title compound.

Yield: 3.91 g.

¹H-NMR (in DMSO-d₆, 9:1 isomeric mixture): δ9.30 (1H, broad), 8.48 (1H, d), 8.27 (3H, broad), 8.22 (1H, s), 8.11 (1H, dd), 8.06 (1H, broad t), 7.96 (1H, s), 7.63 & 7.59 (each 1H, each dd), 7.28 (1H, d), 4.47 (2H, broad), 3.98 (2H, t), 3.02 (2H, q), 2.84 (6H, s), 2.80 (2H, t), 2.64 (1H, m), 2.44 (2H, t), 2.02 & 1.82 (2.7 & 0.3H, each s), 1.36–1.24 (4H, m), 1.05 (3H, d), 0.83 (3H, t).

(d) N-[(4-amino-2-methyl-5-pyrimidyl)methyl]-N-[4-[2-[(5-dimethylaminonaphthylsulfonyl)amino]propionyl]oxy-1-methyl-2-[(1-methylbutyl)dithio]-1-butenyl]formamide hydrochloride The compound prepared in the above step (a) (2.0 g), Compound C (1.8 g) and dimethylaminopyridine (250 mg) were suspended in the mixture of tetrahydrofuran (20 ml) and dichloromethane (20 ml). In this suspension was dissolved dicyclohexylcarbodiimide (1.24 g), and the mixture was left standing at room temperature for about hours. After white insolubles were removed by filtration, the filtrate was concentrated under reduced pressure. The residue obtained was purified by silica gel column chromatography (developed with CHCl₃:acetone=10:1, then eluted with CHCl₃:methanol=45:1→35:1) to give a purified product (3.53 g). The product was dissolved in ethanol and added with 1N hydrochloric acid, and the mixture was concentrated under reduced pressure. The residue was taken in ethanol and concentrated again to give a yellowish white amorphous product. The product was dissolved in chloroform and added dropwise to ether. Greenish white powder crystallized was collected by filtration and dried under reduced pressure to give the title compound.

Yield: 2.25 g.

¹H-NMR (in DMSO-d₆, 10: 1 isomeric mixture): δ9.29 (1H, broad), 8.63 (1H, d), 8.48 (1H, d), 8.29 (3H, broad d), 8.23 (1H, s), 8.11 (1H, dd), 7.95 (1H, s), 7.61 (2H, q), 7.28 (1H, d), 4.47 (2H, broad), 3.86 (2H, m), 3.77 (1H, m), 2.84 (6H, s), 2.62 (4H, m), 2.00 & 1.79 (2.7 & 0.3H, each s), 1.34–1.24 (4H, m), 1.13 (3H, d), 1.04 (3H, d), 0.84 (3H, t).

Example 33

(a) N-methyl-N-[[4-hydroxy-1-methyl-2-[1-(ethyl)propyl]dithio]-1-butenyl]formamide hydrochloride This compound was synthesized in the same manner as described in Example 29.

(b) N-[(4-amino-2-methyl-5-pyrimidyl)methyl]-N-[4-[2-[(5-dimethylaminonaphthyl)amino]ethylaminocarbonyloxy-1-methyl-2-[(1-ethylpropyl)dithio]-1butenyl]formamide hydrochloride In a suspension of the compound obtained in the above step (a) (2.0 g) in tetrahydrofuran (15 ml) was dissolved carbonyldiimidazole (0.90 g). After 0.5 hour, complete consumption of the compound of the above step (a) was confirmed by TLC. Compound A (1.76 g) was added to the reaction. The mixture was stirred at room temperature for about 13 hours. After insolubles were removed by filtration, the filtrate was concentrated under reduced pressure. The residue obtained was purified by silica gel column chromatography (CHCl₃:methanol=60:1→40:1). The purified product (2.97 g) was dissolved in chloroform and added with a solution of 4N hydrochloric acid in dioxane (1.05 ml), and the mixture was concentrated under reduced pressure. The residue obtained was dissolved in chloroform and added dropwise to ether. White to greenish white fluorescent powder obtained was collected by filtration and dried under reduced pressure to give the title compound.

Yield: 2.12 g.

¹H-NMR (in DMSO-d₆, 10:1 isomeric mixture): δ9.31 (1H, broad), 8.50 & 8.28 (each 1H, each d), 8.26 (2H, broad), 8.23 (1H, s), 8.10 (1H, dd), 8.05 (1H, broad t), 7.96 (1H, s), 7.63 (2H, m), 7.31 (1H, broad d), 7.19 (1H, broad t), 4.47 (2H, broad), 3.97 (2H, t), 3.01 (3H, q), 2.86 (6H, s), 2.81 (4H, m), 2.42 (1H, m), 2.02 & 1.82 (0.9 & 0.1H, each s), 1.38 (4H, m), 0.83 (6H, t).

(c) N-[(4-amino-2-methyl-5-pyrimidyl)methyl]-N-[4-[3-[(5-dimethylaminonaphthylsulphonyl)amino]propionyl]oxy-1-methyl-2-[(1-ethylpropyl)dithio]-1-butenyl]formamide hydrochloride The solution of the sodium salt of Compound B (3.0 g) in water (40 ml) was saturated with sodium sulfate. This aqueous solution was adjusted to a pH of ca. 3 with 4N hydrochloric acid, partitioned with chloroform to extract a fluorescent substance. After the chloroform layer was dried with anhydrous sodium sulfate, the solvent was evaporated under reduced pressure. The residue obtained (1.67 g), dimethylaminopyridine (200 mg) and the compound prepared in the above step (a) (2.0 g) were dissolved in the mixture of tetrahydrofuran (15 ml) and acetonitrile (10 ml). Dicyclohexylcarbodiimide (1.24 g) was added, and the resulting solution was left standing at room temperature for about 12 hours. After white insolubles were removed by filtration, the filtrate was evaporated under reduced pressure. The residue obtained was dissolved in chloroform and purified by silica gel column chromatography (CHCl₃:methanol=60:1→40:1). The purified product (2.14 g) was dissolved in chloroform and added with a solution of 4N hydrochloric acid in dioxane (0.77 ml). The mixture was concentrated under reduced pressure. The residue obtained was dissolved in chloroform and added dropwise to ether. Pale green powdery crystals were collected by filtration and dried under reduced pressure to give the title compound.

Yield: 2.06 g.

¹H-NMR (in DMSO-d₆, 9:1 isomeric mixture): δ9.30 (1H, broad), 8.49 (1H, d), 8.28 (3H, broad), 8.21 (1H, s), 8.11 (1H, dd), 8.06 (1H, broad t), 7.95 (1H, s), 7.63 & 7.59 (each 1H, t), 7.29 (1H, broad), 4.47 (2H, broad), 4.00 (2H, t), 3.02 (2H, q), 2.85 (6H, s), 2.81 (2H, t), 2.44 (3H, m), 2.01 & 1.82 (0.9 & 0.1H, each s), 1.38 (4H, m), 0.84 (6H, t).

Example 34

(a) N-[(4-amino-2-methyl-5-pyrimidyl)methyl]-N-[4-hydroxy-1-methyl-2-[(1-pentyl)dithio]-1-butenyl]formamide This compound was synthesized in the same manner as described in Example 29.

(b) N-[(4-amino-2-methyl-5-pyrimidyl)methyl]-N-[4-[3-[(5-dimethylaminonaphthylsulfonyl)amino]propionyl]oxy-1-methyl-2-[(1-pentyl)dithio]-1-butenyl]formamide hydrochloride A solution of the sodium salt of Compound B (4.0 g) in water (40 ml) was saturated with sodium slufate. To this solution was added 4N hydrochloric acid to adjust the pH to about 3, and the mixture was partitioned with chloroform to extract a fluorescent substance. After the chloroform layer was dried with anhydrous sodium sulfate, the solvent was evaporated under reduced pressure. The fluorescent residue obtained (2.80 g), dimethylaminopyridine (250 mg) and the compound obtained in the above step (a) (3.34 g) were dissolved in the mixture of tetrahydrofuran (15 ml) and acetonitrile (10 ml). After dicyclohexylcarbodiimide (1.86 g) was added, the mixture was left standing at room temperature for about 12 hours. White insolubles were removed by filtration, and the filtrate was concentrated under reduced pressure. The residue was dissolved in chloroform and purified by silica gel column chromatography (CHCl$_3$:methanol=60:1→40:1). The purified product obtained (4.19 g) was dissolved in chloroform and added with a solution of 4N hydrochloric acid in dioxane (1.5 ml). The mixture was concentrated under reduced pressure. The residue was dissolved in chloroform and added dropwise to ether. Pale green powdery crystals obtained was collected by filtration and dried under reduced pressure to give the title compound.

Yield: 4.13 g.

$^1$H-NMR (in DMSO-d$_6$, 9:1 isomeric mixture): δ9.27 (1H, broad), 8.49 & 8.28 (each 1H, each d), 8.24 (2H, broad), 8.20 (1H, s), 8.12 (1H, d), 8.07 (1H, broad), 7.94 (1H, s), 7.64 & 7.60 (each 1H, each t), 7.29 (1H, d), 4.47 (2H, broad), 4.01 (2H, t), 3.03 (2H, q), 2.85 (6H, s), 2.79 (2H, t), 2.45 (2H, t), 2.01 & 1.82 (2.7 & 0.3H, each s), 1.43 (2H, m), 1.24 (4H, m), 0.84 (3H, m).

Example 35

(a) N.[(4-amino-2-methyl-5-pyrimidyl)methyl]-N-[4-hydroxy-1-methyl-2-[(2-propenyl)dithio]-1-butenyl]formamide This compound was synthesized in the same manner as described in Example 29.

(b) N-[(4-amino-2-methyl-5-pyrimidyl)methyl]-N-[4-[2-amino-3-(3,4-dipivaloyloxyphenyl)propionyl]oxy-1-methyl-2-[(2-propenyl)dithio]-1-butenyl]formamide This compound was synthesized with the compound prepared in the above step (a) in the same manner as described in Example 30 (b).

$^1$H-NMR (in CDCl$_3$): δ7.97 (1H, s), 7.86 (1H, s), 7.23–7.12 (3H, m), 5.72–5.64 (1H, m), 5.16–5.10 (2H, m), 4.34 (1H, t), 4.29 (1H, m), 4.16 (1H, m), 3.22 (2H, t), 3.11 (32H, d), 2.91 (2H, m), 2.40 (3H, s), 2.04 (3H, s), 1.34 (18H, s).

Example 36

(a) N-[(4-amino-2-methyl-5-pyrimidyl)methyl]-N-[4-hydroxy-1-methyl-2-[(1-butyryl)thio]-1-butenyl]formamide This compound was synthesized in accordance with the report (2) by Matsukawa et at. (supra).

(b) N-[(4-amino-2-methyl-5-pyrimidyl)methyl]-N-[4-[3-[(5-dimethylaminonaphthylsulfonyl)amino]propionyl]oxy-1-methyl-2-[(1-butyryl)thio]-1-butenyl]formamide The sodium salt of Compound B (5.2 g) was dissolved in water (100 ml). To this solution was added 4N hydrochloric acid to adjust the pH to 2–3, and the yellowish green insolubles were extracted with chloroform. After the chloroform layer was dried with anhydrous sodium sulfate, the solvent was evaporated under reduced pressure. The residue obtained, the compound obtained in the above step (a) (3.53 g) and dimethylaminopyridine (250 mg) were dissolved in the mixed solvent of tetrahydrofuran (25 ml), acetonitrile (10 ml) and dichloromethane (20 ml). To the mixed solution was added dicyclohexylcarbodiimide (2.1 g), and the mixture was stirred at room temperature for about 16 hours. After insolubles were removed by filtration, the filtrate was concentrated under reduced pressure. The residue was purified by silica gel column chromatography (CHCl$_3$:methanol=70:1→40:1) to give the title compound.

Yield: 2.86 g.

$^1$H-NMR (in DMSO-d$_6$, 9:1 isomeric mixture): δ8.47, 8.25 & 8.11 (each 1H, each d), 8.08 (1H, t), 7.79 & 7.74 (0.1 & 0.9H, each s), 7.73 & 7.71 (0.1 & 0.9H, each s), 7.63 & 7.58 (each 1H, each t), 7.25 (1H, d), 6.68 (2H, broad), 4.36 (2H, broad), 3.88 (2H, t), 3.01 (2H, q), 2.83 (6H, s), 2.53 (2H, t), 2.42–2.36 (4H, m), 2.24 & 2.01 (each 3H, s), 1.45 (2H, m), 0.82 (3H, t).

Example 37

(a) N-[(4-amino-2-methyl-5-pyrimidyl)methyl]-N-[4-hydroxy-1-methyl-2-[(iso-butyryl)thio]-1-butenyl]formamide This compound was synthesized in the same manner as described in Example 36.

(b) N-[(4-amino-2-methyl-5-pyrimidyl)methyl]-N-[4-[3-[(5-dimethylaminonaphthylsulfonyl)amino]propionyl]oxy-1-methyl-2-[(isobutyryl)thio]-1-butenyl]formamide hydrochloride The solution of the sodium salt of Compound B (5.2 g) in water (100 ml) was saturated with sodium sulfate. N hydrochloric acid was added dropwise to the solution to adjust the pH to 3, and the mixture was partitioned with chloroform to extract fluorescent substances. The chloroform layer was dried with anhydrous sodium sulfate and concentrated under reduced pressure. The residue obtained (3.5 g), dimethylaminopyridine (250 mg) and the compound prepared in the above step (a) (3.84 g) were dissolved in the mixed solvent of dichloromethane (20 ml), tetrahydrofuran (10 ml) and acetonitrile (10 ml). After dicyclohexylcarbodiimide (2.28 g) was added to the solution, the mixture was stirred at room temperature for about 16 hours. Crystalline solids deposited were removed by filtration, and the filtrate was evaporated under reduced pressure. The residue obtained was purified by silica gel column chromatography (CHCl$_3$:methanol= 80:1→40:1). The purified product (3.98 g) was dissolved in ethanol and added with a solution of 4N hydrochloric acid in dioxane (3.0 ml), and the mixture was concentrated under reduced pressure. The residue obtained was dissolved in chloroform and added dropwise to ether. Pale green fluorescent powder obtained was collected by filtration and dried under reduced pressure to give the title compound.

Yield: 4.79 g.

$^1$H-NMR (in DMSO-d$_6$): δ9.23 (1H, broad), 8.59 & 8.36 (each 1H, each broad), 8.20 (1H, s), 8.13 (3H, m), 8.05 (1H, broad s), 7.80 (1H, s), 7.66 (2H, m), 7.44 (1H, broad), 4.50 (2H, broad s), 3.97 (2H, t), 3.01 (2H, q), 2.93 (6H, s), 2.56 (1H, m), 2.53 (2H, broad), 2.48 (3H, s), 2.11 (3H, s), 1.01 (6H, d).

(c) N-[(4-amino-2-methyl-5-pyrimidyl)methyl]-N-[4-[2-[(5-dimethylaminonaphthylsulfonyl)amino]propionyl]oxy-1-methyl-2-[(isobutyryl)thio]-1-butenyl]formamide hydrochloride Compound C (2.7 g), the compound prepared in the above step (a) (2.8 g) and dimethylaminopyridine (250 mg) were suspended in tetrahydrofuran (20 ml) and dichloromethane (20 ml). Dicyclohexylcarbodiimide (1.77 g) was dissolved in this solution, and left standing at room temperature for about 12 hours. After white insolubles were removed by filtration, the filtate was concentrated under reduced pressure. The residue obtained was purified by silica gel column chromatography (developed with CHCl$_3$:acetone=10:1, then eluted with CHCl$_3$:methanol=40:1→35:1). The purified product (2.78 g) was dissolved in ethanol (50 ml) and added with 1N hydrochloric acid (4.0 ml), and the mixture was concentrated under reduced pressure. Ethanol was added again to the residue obtained. And then the mixture was concentrated under reduced pressure to give a yellowish white amorphous product. The product was dissolved in chloroform and added dropwise to ether. Greenish white powder deposited was collected by filtration and dried under reduced pressure to give the title compound.

Yield: 2.60 g.

¹H-NMR (in DMSO-d₆): δ9.20 (1H, broad), 8.57 (1H, d), 8.46 & 8.27 (each 1H, each d), 8.17 (1H, s), 8.09 (1H, d), 8.04 (2H, broad), 7.81 (1H, s), 7.60 (2H, m), 7.26 (1H, d), 4.49 (2H, broad), 3.88–3.80 (3H, m), 3.76 (1H, m), 2.83 (6H, s), 2.58 (1H, m), 2.46 (3H, s), 2.37 (2H, broad), 2.10 (3H, s), 1.11 (3H, d), 1.02 (6H, d).

Example 38

(a) N-[(4-amino-2-methyl-5-pyrimidyl)methyl]-N-[4-hydroxy-1-methyl-2-[(pivaloyl)thio]-1-butenyl]formamide This compound was synthesized in the same manner as described in Example 36.

(b) N-[(4-amino-2-methyl-5-pyrimidyl)methyl]-N-[4-[3-[(5-dimethylaminonaphthylsulfonyl)amino]propionyl]oxy-1-methyl-2-[(pivaloyl)thio]-1-butenyl]formamide hydrochloride The solution of the sodium salt of Compound B (5.2 g) in water (100 ml) was saturated with sodium sulfate. 4N hydrochloric acid was added dropwise to the solution to adjust the pH to 3. The mixture was then partitioned with chloroform to extract fluorescent substances. The chloroform layer was dried with anhydrous sodium sulfate and concentrated under reduced pressure. The residue obtained (3.60 g), dimethylaminopyridine (250 mg) and the compound prepared in the above step (a) (4.03 g) were dissolved in the mixed solvent of dichloromethane (30 ml) and tetrahydrofuran (15 ml). Dicyclohexylcarbodiimide (2.4 g) was added to the solution, and the mixture was stirred at room temperature for about 14 hours. After crystalline solids deposited were removed by filtration, the filtrate was evaporated under reduced pressure. The residue obtained was purified by silica gel column chromatography (CHCl₃:methanol=70:1→40:1). The purified product (5.08 g) was dissolved in ethanol and added with a solution of 4N hydrochloric acid in dioxane (1.9 ml), and then the mixture was concentrated under reduced pressure. The residue obtained was dissolved in chloroform and added dropwise to ether. Pale green fluorescent powder obtained was collected by filtration and dried under reduced pressure to give the title compound.

Yield: 4.67 g.

¹H-NMR (in DMSO-d₆): δ9.27 (1H, broad), 8.48 & 8.26 (each 1H, each d), 8.19 (1H, s), 8.10 (1H, dd), 8.06 (3H, broad m), 7.79 (1H, s), 7.63 & 7.59 (each 1H, each t), 7.28 (1H, d), 4.50 (2H, broad), 3.96 (2H,.t), 3.01 (2H, q), 2.84 (6H, s), 2.46 (3H, s), 2.41 (2H, t), 2.12 (3H, s), 1.06 (9H, s).

(c) N-[(4-amino-2-methyl-5-pyrimidyl)methyl]-N-[4-[3-[(5-dimethylaminonaphthylsulfonyl)amino]propionyl]oxy-1-methyl-2-[(pivaloyl) thio]-1-butenyl]formamide hydrochloride The compound prepared in the above step (a) (3.8 g), Compound C (3.4 g) and dimethylaminopyridine (250 mg) were suspended in a mixed solvent of tetrahydrofuran (20 ml) and dichloromethane (20 ml). Dicyclohexylcarbodiimide (2.3 g) was dissolved in this solution and left standing at room temperature for about 11 hours. After white insolubles were removed by filtration, the filtrate was concentrated under reduced pressure. The residue obtained was purified by silica gel column chromatography (CHCl₃:methanol= 50:1→40:1). The purified product (4.65 g) was dissolved in ethanol (100 ml) and added with 1N hydrochloric acid (6.9 ml), and then the mixture was concentrated under reduced pressure. Ethanol was added to the residue obtained. The mixture was concentrated again under reduced pressure to give a yellowish white amorphous product. The product was dissolved in chloroform and added dropwise to ether. Greenish white powder deposited was collected by filtration and dried under reduced pressure to give the title compound.

Yield: 4.07 g.

¹H-NMR (in DMSO-d₆): δ9.24 (1H, broad), 8.58 (1H, d), 8.47 & 8.28 (each 1H, each d), 8.19 (1H, s), 8.09 (1H, dd), 8.06 (2H, broad), 7.81 (1H, s), 7.60 (2H, q), 7.28 (1H, d), 4.49 (2H, broad), 3.83 (2H, m), 3.75 (1H, m), 2.84 (6H, s), 2.46 (3H, s), 2.34 (2H, broad), 2.11 (3H, s), 1.10 (3H, d), 1.07 (9H, s).

Example 39

(a) N-[(4-amino-2-methyl-5-pyrimidyl)methyl]-N-[4-hydroxy-1-methyl-2-[(benzoyl)thio]-1-butenyl]formamide This compound was synthesized in the same manner as described in Example 36.

(b) N-[(4-amino-2-methyl-5-pyrimidyl)methyl]-N-[4-[3-[(5-dimethylaminonaphthylsulfonyl)amino]propionyl]oxy-1-methyl-2-[(benzoyl)thio]-1-butenyl]formamide hydrochloride The solution of the sodium salt of Compound B (5.0 g) in water (80 ml) was saturated with sodium sulfate. 4N hydrochloricacid was added dropwise to the solution to adjust the pH to 3, and the mixture was partitioned with chloroform to extract fluorescent substances. The chloroform layer was dried with anhydrous sodium sulfate and concentrated under reduced pressure. The residue obtained (3.5 g), dimethylaminopyridine (250 mg) and the compound prepared in the above step (a) (4.3 g) were dissolved in the mixed solvent of dichloromethane (15 ml) and tetrahydrofuran (15 ml). After dicyclohexylcarbodiimide (2.27 g) was added to the solution, and the mixture was stirred at room temperature for about 16 hours. Crystalline solids deposited were removed by filtration, and the filtrate was evaporated under reduced pressure. The residue obtained was purified by silica gel column chromatography (CHCl₃:methanol=60:1→40:1). The purified product (2.82 g) was dissolved in ethanol and added with a solution of 4N hydrochloric acid in dioxane (1.1 ml). And then the mixture was concentrated under reduced pressure. The residue obtained was dissolved in chloroform and added dropwise to ether. Pale green fluorescent powder obtained was collected by filtration and dried under reduced pressure to give the title compound.

Yield: 2.70 g.

¹H-NMR (in DMSO-d₆): δ9.14 (1H, broad), 8.48 & 8.27 (each 1H, each d), 8.20 (1H, s), 8.10 (1H, dd), 8.06 (3H, broad m), 7.92 (1H, s), 7.74–7.50 (7H, m), 7.28 (1H, d), 4.52 (2H, broad), 4.01 (2H, t), 3.01 (2H, q), 2.84 (6H, s), 2.66 (2H, broad), 2.40 (2H, t), 2.22 & 2.18 (each 3H, each s).

Example 40

(a) N-(2-hydroxyethyl)-N-[2-(2-propyl)dithio]ethyl]acetamide

In the solution of Intermediate 12 (8.0 g) in distilled water (50 ml) was dissolved Sodium hydroxide (2.8 g). Sodium 2-propylthiosulfate (10 g) in the form of powder was dissolved in the solution. The oily product deposited was extracted with ethyl acetate and dried over anhydrous sodium sulfate. The solvent was then evaporated under reduced pressure. The residue obtained was purified by silica gel column chromatography (CHCl₃:methanol=50:1→30:1) to give the title compound.

Yield: 4.2 g.

¹H-NMR (in CDCl₃, 2:1 isomeric mixture): δ3.78 (2H, m), 3.62 (2H, m), 3.54 & 3.50 (1.33 & 0.67H, each t), 3.21 (1H, t), 3.03 (1H, m), 2.91 & 2.81 (0.67 & 1.33H, each t), 2.18 & 2.15 (2 & 1H, each s), 1.33 (6H, d).

(b) N-[2-[2-[(5-dimethylaminonaphthylsulfonyl)amino]ethylaminocarbonyloxy]ethyl]-N-[2-[(2-propyl)dithio]ethyl]acetamide hydrochloride In the solution of the compound prepared in the above step (a) (2.0 g) in tetrahydrofuran (15 ml) was dissolved carbodiimidazole (1.54 g) in the form of powder in a water bath at 40—C. (about 5 minutes). Compound A (2.9 g) was added to the solution, and the mixture was stirred at room temperature for about 15 minutes. After insolubles were removed by filtration, the filtrate was evaporated under reduced pressure. The residue obtained was purified by silica gel column chromatography ($CHCl_3$:methanol=60:1→40:1). The fluorescent yellowish green residue (3.76 g) thus obtained was dissolved in chloroform (50 ml), added with a solution of 4N hydrochloric acid in dioxane (1.7 ml) and concentrated under reduced pressure. The residue obtained was dissolved in chloroform and added dropwise to ether (200 ml). The white powdery solids obtained were collected by filtration and dried under reduced pressure to give the title compound.

Yield: 3.64 g.

$^1$H-NMR (in DMSO-$d_6$, 1:1 isomeric mixture): δ8.47, 8.27 & 8.09 (each 1H, each d), 7.98 (1H, broad t), 7.61 (2H, m), 7.26 (1H, d), 7.16 & 7.09 (each 0.5H, each broad t), 4.01 & 3.95 (each 1H, each t), -3.53–3.37 (4H, m), 3.04 (1H, m), 2.97 (2H, m), 2.87–2.76 (10H, m), 2.01 & 1.96 (each 1.5H, each s), 1.22 (6H, dd).

Example 41

(a) N-(2-hydroxyethyl)-N-[2-[2-(tert-butyloxycarbonylamino)propionylthio]vinyl]formamide In the solution of sodium hydroxide (2.4 g) in distilled water (60 ml) was dissolved Intermediate 2 (6.3 g). An active ester obtained from N-Boc-L-alanine and N-hydroxysuccinimide (6.3 g, Novabiochem. Code No. 04-12-0003) was dissolved in a mixed solvent of acetone (15 ml) and methanol (15 ml). The solution was added to the ice-cooled intermediate solution described above. The solution obtained by mixing these solutions exhibited a pH of about 7. After the solution was partitioned with chloroform, the chloroform layer obtained was dried with anhydrous sodium sulfate. The chloroform layer was concentrated under reduced pressure and purified by silica gel column chromatography to give the title compound.

Yield: 6.72 g $^1$H-NMR (in $CDCl_3$, 3:1 isomeric mixture): δ8.33 (0.75H, s), 8.11 (0.25H, s), 6.29 (0.25 H, d), 6.49 (0.75H, d), 6.21 (0.75H, d), 6.25 (0.25H, d), 4.91 (1H, broad), 4.39 (1H, m), 3.76 (4H, m), 1.47 (9H, s), 1.41 (3H, d).

Example 42

(a) N-(2-hydroxyethyl)-N-[2-[(N-(tert-butyloxycarbonyl-2-pyrrolidyl)carbonylthio]vinyl]formamide In the solution of sodium hydroxide (3.2 g) in distilled water (60 ml) was dissolved Intermediate 2 (8.4 g). An active ester obtained from N-Boc-L-proline and N-hydroxysuccinimide (12.5 g, Novabiochem. Code No. 04-12-0076) was dissolved in a mixed solvent of acetonitrile (40 ml) and methanol (35 ml). The solution was added to the ice-cooled above intermediate solution in methanol (20 ml) and acetonitrile (20 ml). The solution obtained by mixing these solutions exhibited a pH of about 7. After the solution was partitioned with chloroform, the chloroform layer obtained was dried with anhydrous sodium sulfate. The chloroform layer was concentrated under reduced pressure and purified by silica gel column chromatography ($CHCl_3$:methanol=80:1→40:1) to give the title compound.

Yield: 8.47 g.

$^1$H-NMR (in $CDCl_3$, 3:1 isomeric mixture): δ8.33 (0.75H, d), 8.10 (0.25H, d), 6.94 (0.25H, q), 6.48 (0.75H, t), 6.27 (0.5H, d), 6.16 (0.38H, d), 6.02 (0.12H, d), 4.46 (1H, m), 3.76 (4H, m), 3.56 (2H, m), 2.24 (1H, m), 2.06 (1H, m), 1.94 (2H, m), 1.46 (9H, d).

(b) N-[2-[2-[(5-dimethylaminonaphthylsulfonyl)amino]propionyloxy]ethyl]-N-[2-[(N-tert-butyloxycarbonyl-2-pyrrolidyl)carbonylthio]vinyl]formamide In the solution of Compound C (2.6 g), the compound prepared in the above step (a) (2.8 g) and dimethylaminopyridine (300 mg) in tetrahydrofuran (40 ml) was dissolved dicyclohexylcarbodiimide (1.8 g), and the mixture was stirred at room temperature for about 15 hours. After white insolubles were removed by filtration, the filtrate was concentrated under reduced pressure. The residue obtained was purified by silica gel column chromatography ($CHCl_3$:acetone=10:1→10:1.5).

Yield: 2.60 g.

$^1$H-NMR (in $CDCl_3$, 5:1 isomeric mixture): δ8.55 (1H, d), 8.29 (1H, d), 8.18 (0.83H, d), 7.90 (0.17H, broad), 7.58 (1H, m), 7.52 (1H, m), 7.19 (1H, d), 6.77 (0.17H, t), 6.24 (1.7H, m), 6.18 (0.17H, d), 5.55 (1H, m), 4.45 (1H, m), 4.03–3.86 (3H, m), 3.7–3.4 (4H, m), 2.89 (6H, s), 2.23 (1H, m), 2.03 (1H, m), 1.93 (2H, m), 1.44 (9H, d), 1.25 (3H, d).

The structures of the compounds in Examples 1–42 are shown in Tables 1 and 2. In the tables, the term "dimer" means a compound which is symmetrical with respect to the disulfide bond.

TABLE 1

| Example | R1 | R2 | R3 | R4 | R5 |
|---|---|---|---|---|---|
| 1(a) | —$CH_3$ | —$CH_3$ | —$CH_2CH_2$—OH | —H | —$SCH_2CH_3$ |
| 2 | —$CH_3$ | —$CH_3$ | —$CH_2CH_2$—OH | —H | —$SCH_2CH_2CH_3$ |
| 3 | —$CH_3$ | —$CH_3$ | —$CH_2CH_2$—OH | —H | —$SCH(CH_3)_2$ |
| 4 | —$CH_3$ | —$CH_3$ | —$CH_2CH_2$—OH | —H | —$SCH(CH_3)CH_2CH_3$ |
| 5 | —$CH_2CH_2$—OH | —H | —H | —H | —$SCH(CH_3)CH_2CH_2CH_3$ |
| 6 | —$CH_2$—COOH | —H | —H | —H | —$SCH(CH_3)CH_2CH_2CH_3$ |
| 7 | —$CH_2CH_2$—OH | —$CH_3$ | —H | —H | —$SCH(CH_3)_2$ |
| 8 | —$CH_2CH_2$—OH | —H | —$CH_3$ | —H | —$SCH(CH_3)_2$ |
| 9 | —$CH_2CH_2$—OH | —H | —$CH_3$ | —H | dimer |
| 10 | —$CH_2CH_2$—OH | —$CH_3$ | —H | —$CH_3$ | —$SCH(CH_3)_2$ |
| 11 | —$CH_2CH_2$—OH | —$CH_3$ | —$CH_2CH_2$—OH | —H | —$SCH(CH_3)_2$ |
| 12 | —$CH_2CH_2$NHBoc | —$CH_3$ | —$CH_2CH_2OH$ | —H | —$SCH_2CH_2CH_3$ |
| 13 | —$CH_2CH_2$NHBoc | —$CH_3$ | —$CH_2CH_2OH$ | —H | —$SCH(CH_3)_2$ |
| 14 | —$CH_2CH_2$NHBoc | —$CH_3$ | —$CH_2CH_2OH$ | —H | —$SCH(CH_3)CH_2CH_3$ |
| 15 | —$CH_2CH_2$NHBoc | —$CH_3$ | —$CH_2CH_2OH$ | —H | —$S(CH_2)_4CH_3$ |

TABLE 1-continued

| Example | R1 | R2 | R3 | R4 | R5 |
|---|---|---|---|---|---|
| 16 | —CH$_2$CH$_2$NHBoc | —CH$_3$ | —CH$_2$CH$_2$OH | —H | —SCH(CH$_3$)CH$_2$CH$_2$CH$_3$ |
| 17 | —CH$_2$CH$_2$NHBoc | —CH$_3$ | —CH$_2$CH$_2$OH | —H | —SCH(CH$_2$CH$_3$)$_2$ |
| 18 | —CH$_2$CH$_2$NHBoc | —CH$_3$ | —CH$_2$CH$_2$OH | —H | —SC$_6$H$_{11}$ |
| 19 | —CH$_2$CH$_2$NHBoc | —CH$_3$ | —CH$_2$CH$_2$OH | —H | —SC$_{12}$H$_{25}$ |
| 20 | —CH$_2$CH$_2$N(CH$_3$)$_2$ | —CH$_3$ | —CH$_2$CH$_2$OH | —H | —SCH(CH$_3$)CH$_2$CH$_2$CH$_3$ |

TABLE 2

| Example | R1 | R2 | R3 | R4 | R5 |
|---|---|---|---|---|---|
| 21 | —CH$_2$CH$_2$NC$_4$H$_8$ | —CH$_3$ | —CH$_2$CH$_2$—OH | —H | —SCH(CH$_3$)CH$_2$CH$_2$CH$_3$ |
| 22 | —CH$_2$CH$_2$NHBoc | —CH$_3$ | —CH$_2$CH$_2$—OH | —H | dimer |
| 23 | —CH$_2$CH$_2$—OH | —H | —H | —H | —SCH(CH$_3$)$_2$ |
| 24 | —CH$_2$CH$_2$—OH | —H | —H | —H | —COCH(CH$_3$)$_2$ |
| 25 | —CH$_2$CH$_2$—OH | —H | —H | —H | —COC(CH$_3$)$_3$ |
| 26 | —CH$_2$CH$_2$—OH | —H | —H | —H | —CO—C$_6$H$_5$ |
| 27 | —CH$_2$CH(CH$_3$)OH | —CH$_3$ | —H | —H | —COC(CH$_3$)$_3$ |
| 28 | —CH$_2$CH$_2$N(CH$_3$)$_2$ | —CH$_3$ | —CH$_2$CH$_2$—OH | —H | —COC(CH$_3$)$_3$ |
| 29 | —CH$_2$—C$_5$H$_6$N$_3$ | —CH$_3$ | —CH$_2$CH$_2$—OH | —H | —S—CH$_2$—C$_4$H$_7$O |
| 30 | —CH$_2$—C$_5$H$_6$N$_3$ | —CH$_3$ | —CH$_2$CH$_2$—OH | —H | —SCH(CH$_3$)$_2$ |
| 31 | —CH$_2$—C$_5$H$_6$N$_3$ | —CH$_3$ | —CH$_2$CH$_2$—OH | —H | —SCH$_2$CH$_2$CH$_3$ |
| 32 | —CH$_2$—C$_5$H$_6$N$_3$ | —CH$_3$ | —CH$_2$CH$_2$—OH | —H | —SCH(CH$_3$)CH$_2$CH$_2$CH$_3$ |
| 33 | —CH$_2$—C$_5$H$_6$N$_3$ | —CH$_3$ | —CH$_2$CH$_2$—OH | —H | —SCH(CH$_2$CH$_3$)$_2$ |
| 34 | —CH$_2$—C$_5$H$_6$N$_3$ | —CH$_3$ | —CH$_2$CH$_2$—OH | —H | —S(CH$_2$)$_4$CH$_3$ |
| 35 | —CH$_2$—C$_5$H$_6$N$_3$ | —CH$_3$ | —CH$_2$CH$_2$—OH | —H | —S—CH$_2$—CH=CH$_2$ |
| 36 | —CH$_2$—C$_5$H$_6$N$_3$ | —CH$_3$ | —CH$_2$CH$_2$—OH | —H | —CO—CH$_2$CH$_2$CH$_3$ |
| 37 | —CH$_2$—C$_5$H$_6$N$_3$ | —CH$_3$ | —CH$_2$CH$_2$—OH | —H | —CO—CH(CH$_3$)$_2$ |
| 38 | —CH$_2$—C$_5$H$_6$N$_3$ | —CH$_3$ | —CH$_2$CH$_2$—OH | —H | —CO—C(CH$_3$)$_3$ |
| 39 | —CH$_2$—C$_5$H$_6$N$_3$ | —CH$_3$ | —CH$_2$CH$_2$—OH | —H | —CO—C$_6$H$_5$ |
| 40* | —CH$_2$CH$_2$—OH | —H | —H | —H | —SCH(CH$_3$)CH$_2$CH$_2$CH$_3$ |
| 41 | —CH$_2$CH$_2$—OH | —H | —H | —H | —CO—CH(CH$_3$)—NH-Boc |
| 42 | —CH$_2$CH$_2$—OH | —H | —H | —H | —CO—C$_4$H$_7$N-Boc |

*In the compound of Example 40, the bond between carbon atoms to which R$^2$ and R$^3$ are bonded, respectively, is a single bond, while in other compound the bond represents a double bond.

In vivo disposition test 1

The distribution and residence in brain of the compounds according to the present invention were evaluated as follows.

The aqueous solutions of the compounds prepared in Examples 3 (b), 30 (b), 29 (b) and 35 (b) were respectively administered at a dose of 5 mg/kg on the basis of Compound D of which both Boc and pivaloyl groups have been deprotected (referred to herein after as DOPA) into the femoral vein of SD rats. Blood samples were taken out from abdominal aorta after a certain period of collected. Immediately after the exsanguination, whole brain was removed. Experiments were carried out with 3 rats at each blood sampling point.

The DOPA concentration in the whole brain was determined in accordance with the method "New Biochemical Experiment Course, Vol. 11, Neurobiochemistry, p. 289–290 (edited by Biochemical Society, Japan, published by Tokyo Kagaku-Dojin, 1990)." As the controls, the Boc-eliminated Compound D and DOPA were administered in the same manner as above to determine the DOPA concentration.

Figure 2:
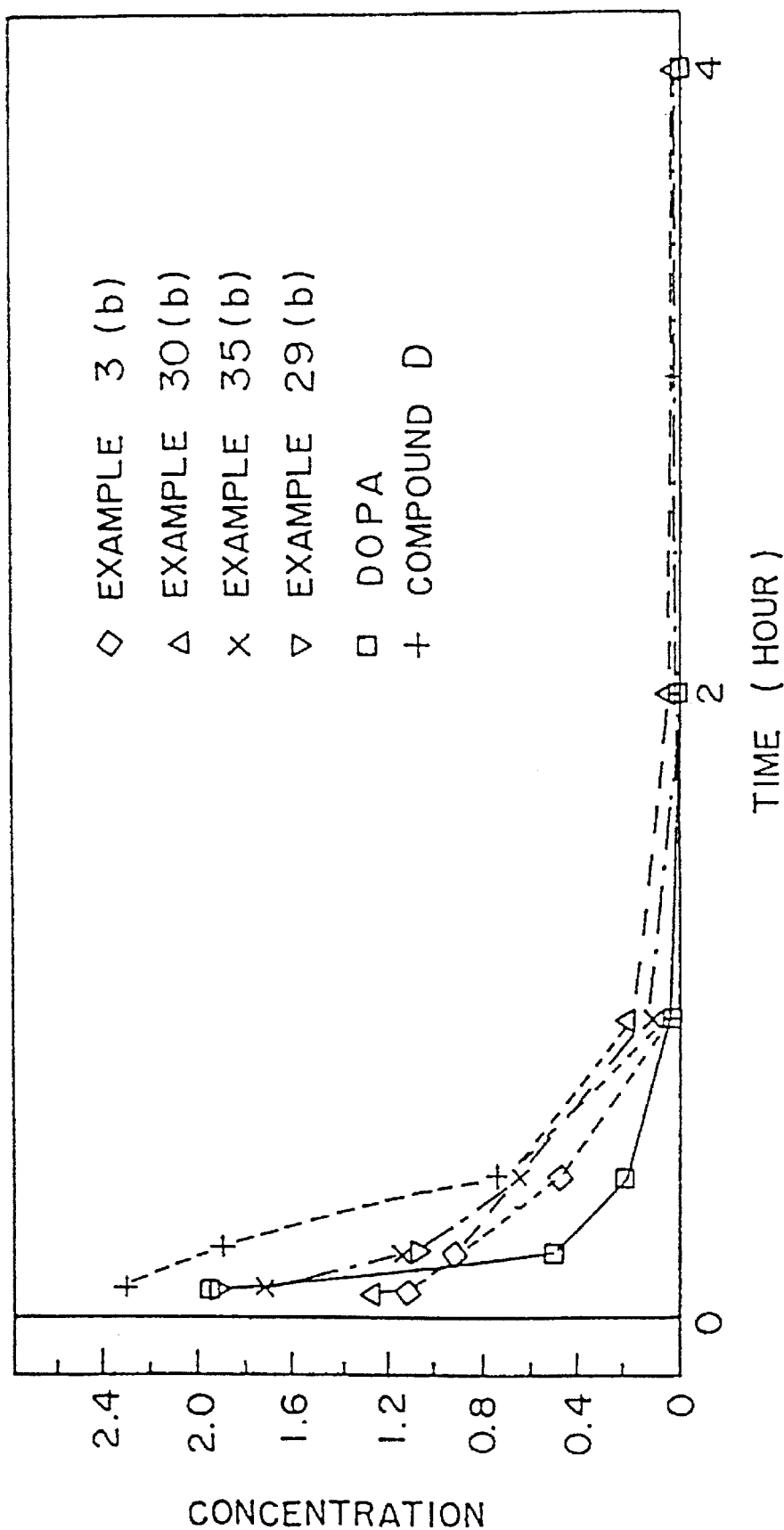

The DOPA concentrations in brain and plasma are shown in FIG. 1 and 2, respectively. It is understood from these figures that DOPA is transferred into brain and stays within brain by the compound according to the present invention.

Furthermore, the area under the concentration of DOPA in brain is shown in the following table.

| | Area under the curve of concentration (AUC) of DOPA in brain (ng · min/g) | | | | | |
|---|---|---|---|---|---|---|
| Time (hr) | Example 3 (a) | Example 30 (b) | Example 35 (b) | Example 29 (b) | DOPA | Boc-elimination of Compound D |
| 0-4 | 82476 | | 10626 | 7151 | 6035 | 3277 |
| 0-2 | | 34595 | | 6659 | 6035 | 3169 |

In vivo disposition test 2

The compounds of Examples 31 (b) and 32 (b) (both supporting Compound A), the compounds of Examples 34 (b) and 38 (b) (both supporting Compound B), and the compounds of Examples 32 (d) and 38 (c) (both supporting Compound C) were respectively dissolved in physiological saline to prepare a 30 μmol/ml (in this connection, those which were hardly soluble in only physiological saline were dissolved in physiological saline containing dimethylsulfoxide, propylene glycol or hydroxypropyl-β-cyclodextrin). These solutions which have passed through a 0.45 μm filter were used for the following experiments.

The solution was administered at a dose of 30 μmol/kg for each compound into the femoral vein of male SD rats. Blood samples were collected with a heparinized syringe from abdominal aorta after a certain period of time. Immediately after exsanguination, whole brain including cerebrum, cerebellum and brain stem was removed from skull part. Whole blood was immediately ice-cooled and centrifuged (3,000 rpm, 10 minutes), and then plasma was collected and freeze-stored at –20° C. The whole brain was rinsed with physiological saline and freeze-stored at –20° C. The administration of the solution and the dissection were conducted under anesthetization with ether.

Samples for the determination were prepared as follows.

After plasma (1 ml) was first stirred, acetonitrile (1.5 ml) and 7% (w/v) perchloric acid (0.1 ml) were added. The mixture was stirred and left standing for 30 minutes, and was subsequently centrifuged (488,000×g, 45 minutes). The supernatant was obtained as a sample for determination.

Brain after thawing was weighed and homogenized (20,000 rpm, 1 minute). After a 7% (w/v) hydrochloric acid-acetonitrile solution (the weight of the brain weighed×5/2 ml) was added, the mixture was homogenized (20,000 rpm, 1 minute), stood for 30 minutes and centrifuged (12,100×g, 45 minutes) to collect the supernatant. The supernatant was further centrifuged (488,000×g, 45 minutes), and the supernatant was obtained as a sample for determination.

In addition to the sample for determination obtained as above, the samples for determination were also prepared for Whole plasma and whole brain taken from the subject animals to which the compound according to the present invention was not administered. The internal standard solution was added in an amount of 1 ml and the weight of the brain weighed×5/2 ml, respectively.

Samples for determination obtained as above were analyzed by high-performance liquid chromatography with a fluorescence detector to isolate and quantitatively determine the fluorescent substance, that is Compound A C. The concentrations of these substances were measured with the calibration curve of the standard solution in which the internal standard solution was added.

Figure 3A:
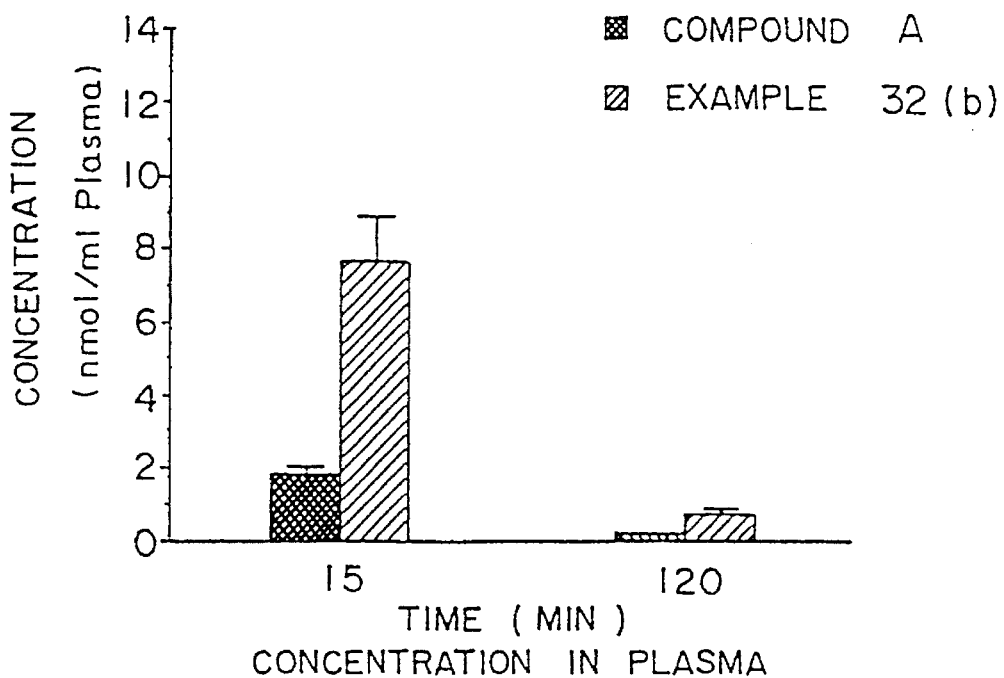
Figure 3B:
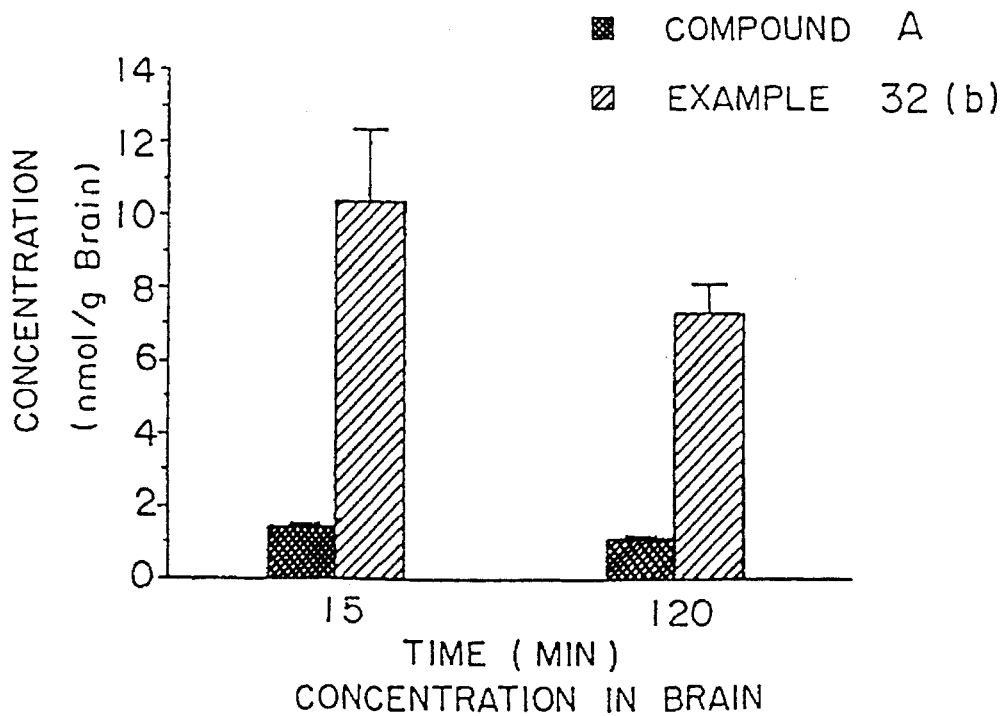
Figure 4A:
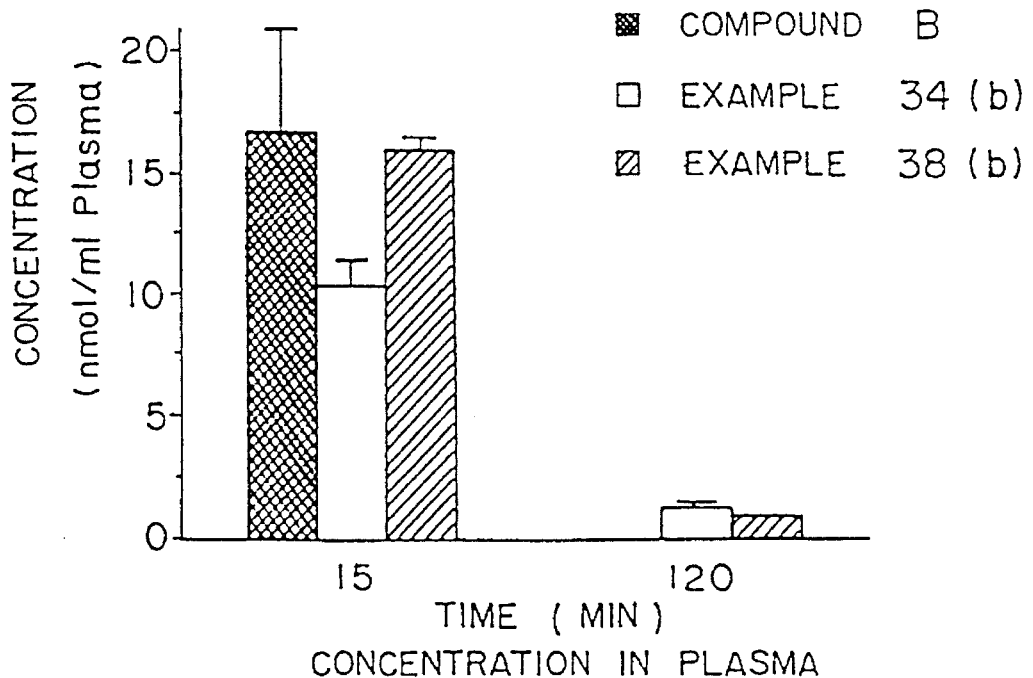
Figure 4B:
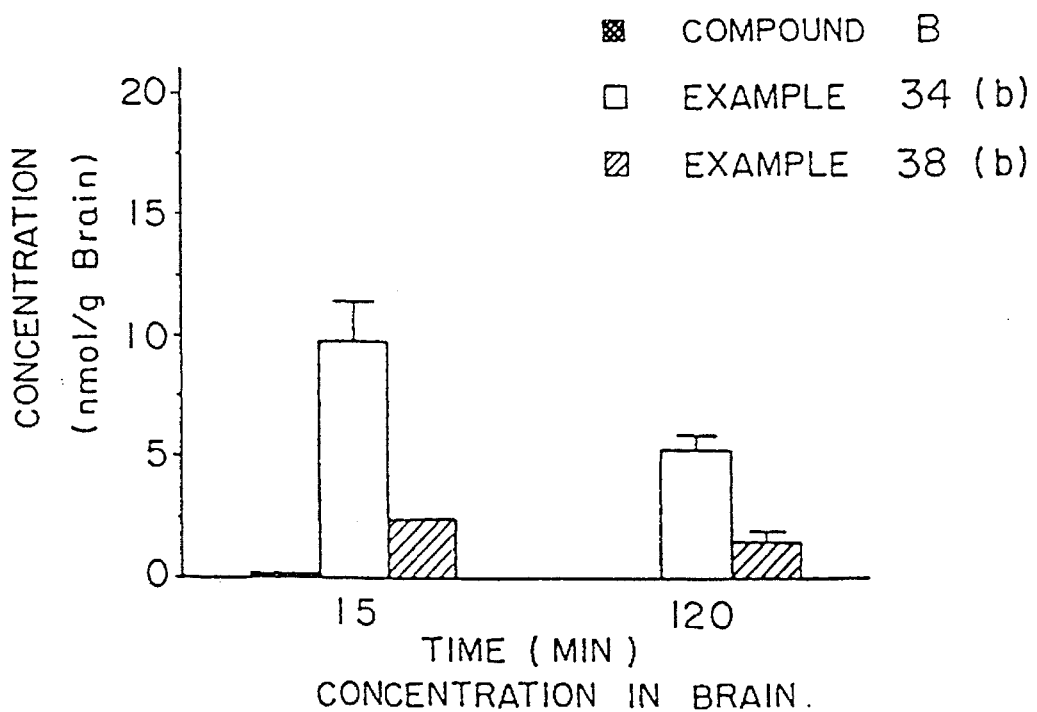
Figure 5A:
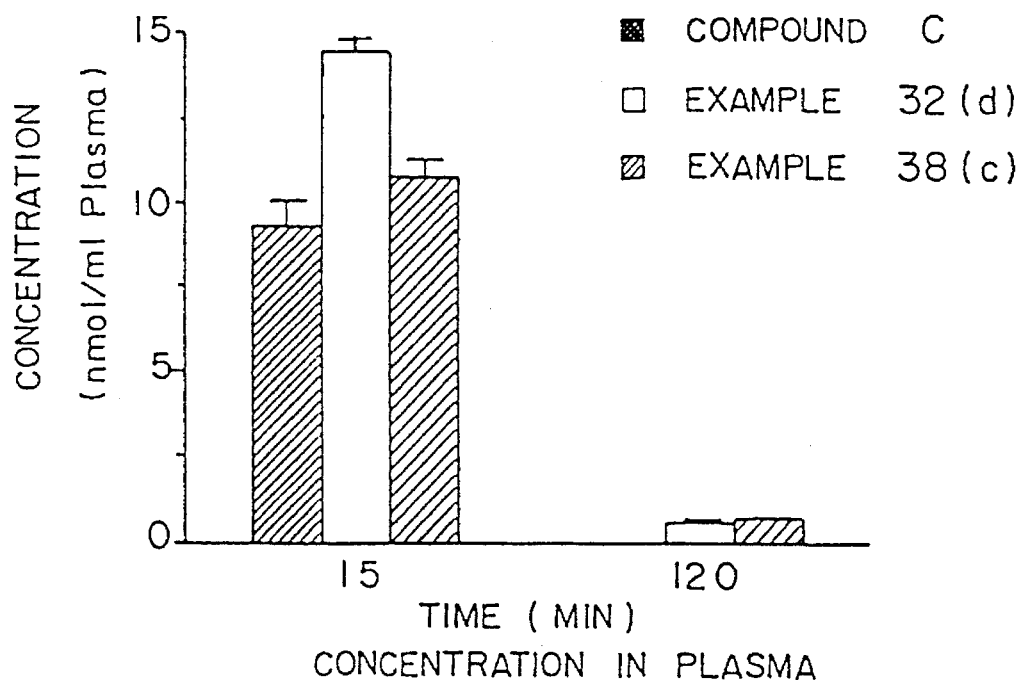
Figure 5B:
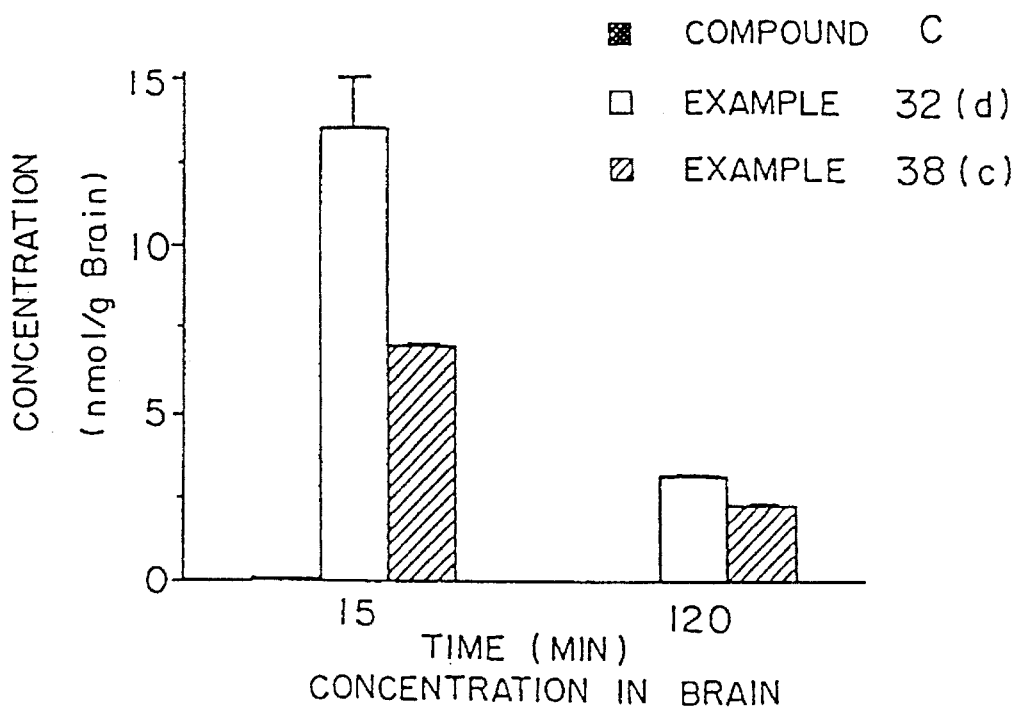

The results are shown in FIGS. 3–5. It is understood apparently from these figures that Compounds A–C are delivered and retained into brain by the compound according to the present invention.

What is claimed is:

1. A compound represented by the general formula

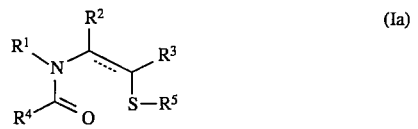

(Ia)

wherein, $R^1$ represents $C_{1-6}$ alkyl which may be substituted by a group selected from hydroxyl, carboxyl, and amino group which may be substituted by $C_{1-6}$ alkyl, $R^2$ represents hydrogen or $C_{1-6}$ alkyl, $R^3$ represents hydrogen or $C_{1-6}$ alkyl which may be substituted by hydroxyl, $R^4$ represents hydrogen or $C_{1-6}$ alkyl, $R^5$ represents an amino acid residue, or —S—$R^6$ or —CO—$R^6$ wherein R6 represents $C_{1-14}$ alkyl which may be substituted by a five- to seven-membered saturated ring; $C_{2-6}$ alkenyl; aryl; $C_{1-8}$ alkoxy; or a five- to seven-membered saturated ring, or the group represented by the general formula (IVa):

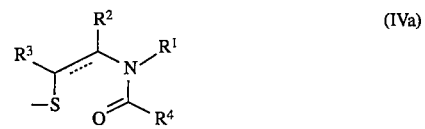

(IVa)

wherein $R^1$, $R^2$, $R^3$ and $R^4$ have the same meanings as defined above, and ......... represents a single bond or a double bond provided that at least one of $R^1$, $R^3$ and $R^5$ contains hydroxyl, carboxyl or amino, and a salt thereof.

2. A compound according to claim 1, wherein $R^1$ represents $C_{1-4}$ alkyl which may be substituted by a group selected from hydroxyl, carboxyl, and amino which may be-substituted by a $C_{1-4}$ alkyl group, $R^2$ represents hydrogen or $C_{1-4}$ alkyl, $R^3$ represents hydrogen or $C_{1-4}$ alkyl which may be substituted by hydroxyl, $R^4$ represents hydrogen or $C_{1-4}$ alkyl, $R^5$ represents an alanine residue, a proline residue or —S—$R^6$ or —CO—$R^6$ wherein $R^6$ represents $C_{1-14}$ alkyl which may be substituted by a five- to seven-membered saturated ring; $C_{2-6}$ alkenyl; phenyl; or cyclohexyl; or $R^5$ represents the group represented by the formula (IVa) defined above wherein $R^1$, $R^2$, $R^3$ and $R^4$ represent the same groups as $R^1$, $R^2$, $R^3$ and $R^4$ in the formula (Ia)).

3. A method for introducing a drug into the brain of a mammal and retaining the drugs within the brain, comprising the step of administering a compound represented by the following formula (IB):

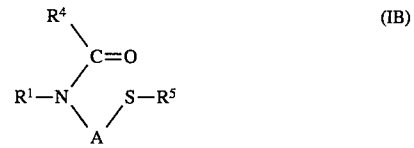

(IB)

wherein, $R^1$ represents alkyl or alkenyl, in which one or more hydrogen atoms in the alkyl group or the alkenyl group may be substituted by a member selected from the group consisting of hydroxyl which may be esterified, etherified or carbamated, carboxyl which may be esterified or amidated, and amino which may be acylated, A represents the following group:

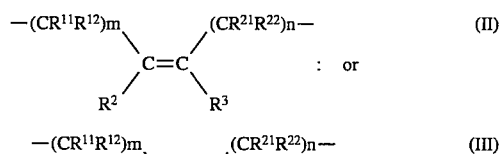

(II) : or (III)

wherein, $R^2$ and $R^3$ represent independently hydrogen, alkyl or alkenyl, in which one or more hydrogen atoms in the alkyl group or the alkenyl group may be substituted by a member selected from the group consisting of hydroxyl which may be esterified, etherified or carbamated, carboxyl which may be esterified or amidated, and amino which may be acylated, m and n are integers of 0 or 1, provided that m and n do not simultaneously represent 1, $R^{11}$, $R^{12}$, $R^{21}$ and $R^{22}$ independently represent hydrogen, alkyl or alkenyl, in which one or more hydrogen atoms in the alkyl group or the alkenyl group may be substituted by a member selected from the group consisting of hydroxyl which may be esterified, etherified or carbamated, carboxyl which may be esterified or amidated, and amino which may be acylated, $R^4$ represents hydrogen or alkyl, and $R^5$ represents an amino acid residue or a group —X—Y, in which X represents sulfur or carbonyl, and Y represents alkyl which may be substituted, alkenyl which may be substituted, or alkoxy which may be substituted, aryl, a 5- to 7-membered saturated ring, or the following group (IVA):

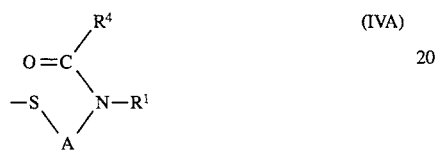

(IVA)

wherein $R^1$, $R^4$ and A have the same meanings as defined above, and a salt thereof, wherein the drug is introduced into the compound through a bond with $R^1$ to $R^5$, $R^{11}$, $R^{12}$, $R^{21}$ or $R^{22}$.

4. The method according to claim 3, wherein $R^1$, $R^2$ and $R^3$ represent independently alkyl or alkenyl where the alkyl and alkenyl group may be substituted by a member selected from the group consisting of hydroxyl; alkylcarbonyloxy which may be substituted by amino; alkoxy; an amino acid residue; carboxyl; alkyloxycarbonyl; amino; alkyloxycarbonylamino; phenyl; naphthyl; cycloalkyl and a five- or six-membered heterocyclic ring which includes up to 2 hetero atoms selected from oxygen, sulfur and nitrogen and may be fused together with another ring and may be substituted by $C_{1-6}$ alkyl and/or amino;

provided that the total number of the carbon atoms of $R^1$, $R^2$ and $R^3$ do not exceed 20, both m and n are 0, and Y represents $C_{1-8}$ alkyl; or $C_{2-8}$ alkenyl; where the alkyl and alkenyl group may be substituted by a member selected from the group consisting of amino, alkyloxycarbonylamino, a five- or six-membered saturated heterocyclic ring containing an oxygen atom or a sulfur atom and $C_{5-7}$ cycloalkyl; or phenyl; naphthyl; or a 5- or 6-membered saturated heterocyclic ring containing a nitrogen atom.

5. A method for introducing a drug into the brain of a mammal and retaining the drug within the brain, comprising the step of administering a compound represented by the following formula (Ib):

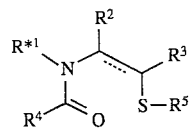

(Ib)

wherein, $R^1$ represents $C_{1-6}$ alkyl which may be substituted by a member selected from the group consisting of hydroxyl, carboxyl, and amino which may be substituted by $C_{1-6}$ alkyl, $R^2$ represents hydrogen or $C_{1-6}$ alkyl, $R^3$ represents hydrogen or $C_{1-6}$ alkyl which may be substituted by hydroxyl, $R^4$ represents hydrogen or $C_{1-6}$ alkyl, $R^5$ represents an amino acid residue, or —S—$R^6$ or —CO—$R^6$ wherein $R^6$ represents $C_{1-14}$ alkyl which may be substituted by a five- to seven-membered saturated ring; $C_{2-6}$ alkenyl; aryl; $C_{1-8}$ alkoxy; or a five- to seven-membered saturated ring, or the group represented by the general formula (IVa):

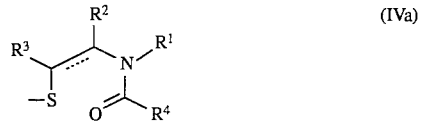

(IVa)

wherein $R^1$, $R^2$, $R^3$ and $R^4$ have the same meanings as defined above, and --------- represents a single bond or a double bond provided that at least one of $R^1$, $R^3$ and $R^5$ contains hydroxyl, carboxyl, or amino, and a salt thereof, wherein the drug is introduced into the compound through a bond with $R^1$, $R^2$, $R^3$, $R^4$ or $R^5$.

6. The method according to claim 5, wherein $R^1$ represents $C_{1-4}$ alkyl which may be substituted by a member selected from the group consisting of hydroxyl, carboxyl, and amino which may be substituted by a $C_{1-4}$ alkyl group, $R^2$ represents hydrogen or $C_{1-4}$ alkyl, $R^3$ represents hydrogen or $C_{1-4}$ alkyl which may be substituted by hydroxyl, $R^4$ represents hydrogen or $C_{1-4}$ alkyl, $R^5$ represents an alanine residue, a proline residue or —S—$R^6$ or —CO—$R^6$ wherein $R^6$ represents $C_{1-14}$ alkyl which may be substituted by a five- to seven-membered saturated ring; $C_{2-6}$ alkenyl; phenyl; or cyclohexyl; or $R^5$ represents the group represented by the formula (IVa) defined above wherein $R^1$, $R^2$, $R^3$ and $R^4$ represent the same groups as $R^1$, $R^2$, $R^3$ and $R^4$ in the formula (Ib).

\* \* \* \* \*